United States Patent [19]

Meyer et al.

[11] Patent Number: 5,288,749
[45] Date of Patent: Feb. 22, 1994

[54] TERTIARY AND SECONDARY AMINES AS ALPHA-2 ANTAGONISTS AND SEROTONIN UPTAKE INHIBITORS

[75] Inventors: Michael D. Meyer; John F. DeBernardis, both of Lindenhurst; Rajnandan Prasad, Vernon Hills; Kevin B. Sippy, Lindenhurst; Karin R. Tietje, Mundelein, all of Ill.

[73] Assignee: Abbott Laboratories, Abbott Park, Ill.

[21] Appl. No.: 811,091

[22] Filed: Dec. 20, 1991

[51] Int. Cl.$^5$ .............. A61K 31/40; C07D 209/34; C07D 209/38; C07D 209/44
[52] U.S. Cl. .................. 514/414; 514/415; 514/416; 514/417; 514/418; 514/224.2; 514/230.5; 514/249; 514/259; 514/248; 514/307; 514/311; 514/312; 514/367; 514/373; 514/375; 514/379; 514/394; 514/434; 514/443; 514/454; 514/457; 514/439; 514/463; 514/469; 514/470; 514/655; 514/361; 548/454; 548/472; 548/475; 548/481; 548/482; 548/484; 548/485; 548/486; 548/491; 548/503; 548/126; 548/164; 548/173; 548/169; 548/179; 548/207; 548/209; 548/217; 548/221; 548/241; 548/305.1; 548/361.1; 548/361.5; 544/50; 544/52; 544/90; 544/92; 544/105; 544/235; 544/237; 544/283; 544/286; 544/353; 544/354; 546/141; 546/149; 546/157; 546/176; 546/177; 549/15; 549/23; 549/32; 549/33; 549/53; 549/54; 549/58; 549/359; 549/399; 549/401; 549/407; 549/433; 549/467; 564/387

[58] Field of Search ............. 548/482, 486, 491, 484, 548/485, 475, 481, 503, 454, 472; 514/414, 415, 416, 417, 418

[56] References Cited

U.S. PATENT DOCUMENTS

| | | | |
|---|---|---|---|
| 4,564,628 | 1/1986 | Horn | 514/438 |
| 4,722,933 | 2/1988 | Horn | 514/438 |
| 4,968,679 | 11/1990 | Junge et al. | 514/222.2 |
| 5,086,074 | 2/1992 | DeBernardis et al. | 546/290 |
| 5,118,704 | 6/1992 | Minaskanian et al. | 514/416 |
| 5,140,040 | 8/1992 | DeBernardis et al. | 514/422 |

Primary Examiner—Emily Bernhardt
Attorney, Agent, or Firm—Jerry F. Janssen

[57] ABSTRACT

The present invention provides tertiary and secondary amine compounds of the formula

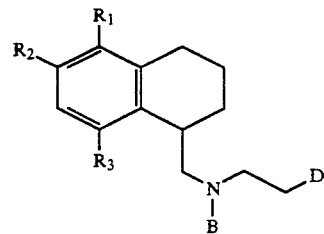

and the pharmaceutically acceptable salts thereof which are antagonists for alpha-2 adrenoreceptors and which inhibit serotonin (5-hydroxytryptamine, 5-HT) uptake.

13 Claims, No Drawings

TERTIARY AND SECONDARY AMINES AS ALPHA-2 ANTAGONISTS AND SEROTONIN UPTAKE INHIBITORS

TECHNICAL FIELD

The present invention relates to novel organic compounds and compositions which are both alpha-2 adrenoreceptor antagonists and serotonin (5-hydroxytryptamine, 5-HT) uptake inhibitors, processes for making such compounds, synthetic intermediates employed in these processes, and a method for treating diseases of the central nervous system including depression, aggression, obsessive compulsive disorders, panic attacks, memory disturbances, anxiety, hypochondriasis, and aspects of Alzheimer's disease, diseases of the vascular system including hypertension, glaucoma and migraine, metabolic disorders such as diabetes or feeding disorders, and alcoholism.

BACKGROUND OF THE INVENTION

There is evidence that the pathophysiology of depression and anxiety disorders is related to some type of serotonin dysfunction. The tricyclic antidepressant imipramine binds with high affinity to a recognition site associated with the transport of 5-HT. The site at which these trycyclic antidepressants bind is not identical to the 5-HT binding site and yet binding of compounds of this type inhibits the uptake of 5-HT (serotonin); an allosteric relationship is postulated (Charney, D. S., Krystal, J. H., Delgado, P. L., Heninger, G. R., *Annu. Rev. Med.* 1990, 41: 437). A number of compounds which demonstrate highly selective serotonin uptake inhibition have shown clinical efficacy as antidepressants (Fuller, R. W., Wong, D. T., *Ann. N.Y. Acad. Sci.*, 1990, 600: 68). It has been found that serotonin uptake inhibitors bind with less affinity to neurotransmitter receptors than the tricyclic antidepressants; this lower binding affinity is thought to be responsible for fewer chlorinergic and histaminergic side effects for these uptake inhibitors (Robertson, D. W., Fuller, R. W., *Ann. Rep. Med. Chem.*, 1991, 26: 23) relative to the tricyclic antidepressants.

Serotonin uptake inhibitors are thought to offer clinical advantages over the tricyclic antidepressants because they exhibit fewer severe adverse drug reactions, particularly as far as cardiovascular side effects and overdose potential. Serotonin uptake inhibitors have shown some indications of efficacy in the treatment of obsessive compulsive disorder (Zak, J., Miller, J., Sheehan, D., Fanous, B., *J. Clin. Psychiatry*, 1990, 49: 23), panic disorders (Balon, R., Pohl, R. I., Yergani, V., Rainey, J., Oxenkrug, G., *Acta Psychiatr. Scand.*, 1987, 75: 315), alcoholism (Gill, K., Amit, Z., Koe, K., *Alcohol*, 1988, 349), and feeding disorders (Wong, D., Fuller, R., *Int. J. Obesity*, 1987, 11: 125). Some of the emotional aspects of Alzheimer's disease were ameliorated by the use of a serotonin uptake inhibitor (Karlsson, I., *Clinical Neuropharmacol.*, 1990, 13 (Suppl 2): 99). There is some indication that the serotonin uptake inhibitor Fluoxetine is effective in the treatment of hypochondriasis (Viswanathan, R., Paradis, C., *Am. J. Psychiatr.*, 1991, 148: 1090).

The adrenergic nervous system plays a major role in the innervation of heart, blood vessel and smooth muscle tissue. Compounds capable of interacting with receptor sites within the adrenergic nervous system can initiate a variety of physiological responses, including vasoconstriction, vasodilation, and increased or decreased heart rate (chronotropic), contactility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptors types within the adrenergic nervous system in order to obtain a desired physiological response separate from other possible, and perhaps less desirable, responses of the system.

The fact that adrenergic and serotonergic nerve terminals exist in close proximity in various brain regions might indicate some kind of functional interaction between these two neurotransmitter systems. There is evidence that presynaptic alpha-2 adrenergic receptors are located on 5-HT nerve terminals where they function to inhibit the release of 5-HT (Gothert, M., Huth, H., *Naunyn-Schmiedegerg's Arch. Pharmacol.*, 1980, 313: 21 and Gothert, M., Huth, H., Schlicker, E., *Naunyn-Schmiedeberg's Arch. Pharmacol.*, 1981, 317: 199). It has been demonstrated in in vitro slice preparations that alpha-2 antagonists are capable of reversing the inhibition of 5-HT release upon electrical stimulation under quasi physiological conditions by either exogenously applied alpha-2 agonists or endogenous norepineprine (NE) (Charney, D. S., Krystal, J. H., Delgado, P. L., Heninger, G. R., *Annu. Rev. Med.* 1990, 41: 437). One might therefore conclude that an agent which combines alpha-2 antagonist activity with 5-HT uptake inhibitory activity would be more effective than either activity alone in increasing the biophase concentration of 5-HT. Compounds such as napamezole, Win 51181-2, which is a potent and selective alpha-2 adrenergic receptor antagonist and also inhibits serotonin (5-hydroxytryptamine, 5-HT) uptake, is under development by Sterling Drug as an antidepressant (*Pharma Projects*, May 1991, 12). Chromic uptake blockade will, over time, result in down-regulation of the alpha-2 receptor, and perhaps the delay in onset of antidepressant efficacy correlates with the time required for receptor down-regulation.

1-Aminomethyl-1,2,3,4-tetrahydronaphthalenes have been described by J. F. DeBernardis, R. E. Zelle and F. Z. Basha in International Patent Application Number WO 89/06645. One of their generic structures encompasses methylenedioxy and ethylenedioxy heterocyclic compounds which are excluded from the present invention. Their compounds do not possess the selective alpha-2 antagonist activity with the inhibition of serotonin uptake profile of the present compounds.

SUMMARY OF THE INVENTION

The compounds of the present invention demonstrate the ability to selectively inhibit serotonin (5-hydroxytryptamine, 5-HT) uptake and alpha-2 adrenergic receptors, i.e. are alpha-2 antagonists, which are mainly distributed on the membranes of central and peripheral adrenergic neurons and on the tissues innervated thereby. By inhibiting interaction with the alpha-adrenergic receptors in the peripheral nervous system, one can modulate the function of adrenergic neurons and hemodynamic equilibrium which is therapeutically useful in a multitude of cardiovascular indications, such as hypertension, congestive heart failure, and a variety of vascular spastic conditions. Furthermore, the alpha-adrenergic antagonists are useful in certain neurological and psychiatric disorders such as depression. Dual pharmacophores which are alpha-2 antagonists and also inhibit the uptake of serotonin would be anticipated to have a beneficial synergistic effect with enhanced efficacy over each type of activity alone, the potential for faster onset of action and/or efficacy among non-responding patients while perhaps having a desirable side effect profile.

In accordance with the principal embodiment of the present invention, there are provided alpha-2 adrenoreceptor antagonists and serotonin (5-hydroxytryptamine, 5-HT) uptake inhibiting compounds of the formula I:

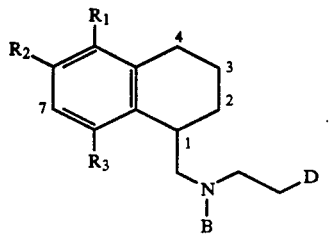

and the pharmaceutically acceptable salts thereof. In the above formula $R_1$ is alkoxy of from one to four carbon atoms, $R_2$ is hydrogen or taken together with $R_1$ is methylenedioxy or ethylenedioxy, and $R_3$ is hydrogen, fluorine, or chlorine.

The substituent B is hydrogen or alkyl of from one to three carbon atoms.

The residue D is selected from

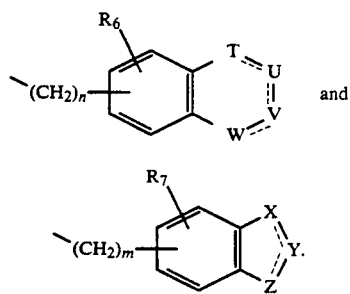

When D is

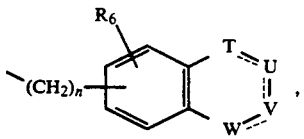

then n is 0, 1, or 2, and T, U, V, and W represent $>CH_2$, $=CH-$, $>C=O$, $>O$, $>N-R_8$ and $=N-$, and $>S$, $>S(O)$, and $>SO_2$. The dotted lines represent optional double bonds and $R_8$ is hydrogen, alkyl of from one to four atoms, or alkylsulfonyl. $R_6$ is one, two, or three substituents independently selected from hydrogen, alkyl of from one to four carbon atoms, halogen, hydroxy, alkoxy of from one to four carbon atoms, amino, and thioalkoxy of from one to four carbon atoms. The following provisos apply: (a) when there is a double bond between T and U and/or V and W, then there cannot be a double bond between U and V, (b) not more than three of T, U, V, and W are nitrogen, (c) not more than two of T, U, V, and W are oxygen, and then not in contiguous position, (d) not more than two of T, U, V, and W are sulfur, and (e) not more than two of T, U, V, and W are $>C=O$.

Alternatively, when D is

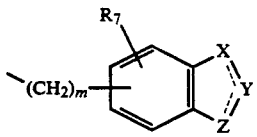

then m is 0, 1, or 2, and X, Y, and Z are independently selected from $CH_2$, $=CH-$, $>C=O$, $>O$, $>N-R_8$ and $=N-$, and $>S$, $>S(O)$, and $>SO_2$. The dotted lined represent optional double bonds, and $R_8$ is hydrogen, alkyl of from one to four atoms, or alkylsulfonyl. $R_7$ is one, two, or three substituents independently selected from the group consisting of hydrogen, alkyl of from one to four carbon atoms, halogen, hydroxy, alkoxy of from one to four carbon atoms, amino, and thioalkoxy of from one to four carbon atoms. The following provisos apply: (f) there may be only one double bond between either X and Y or between Y and Z, (g) not more than one of X, Y, and Z is oxygen, (h) not more than two of X, Y, and Z are sulfur, and (i) not more than two of X, Y, and Z are $>C=O$.

The pharmaceutically acceptable salts and individual stereoisomers of compounds of structural formula I above, as well as mixtures thereof, are also contemplated as falling within the scope of the present invention.

In another aspect, the present invention also relates to a method for antagonizing alpha-2 adrenoreceptor activity and inhibiting 5-hydroxytryptamine uptake in a mammal in need of such treatment, comprising administering to the mammal a therapeutically effective amount of a compound of claim 1.

In yet another aspect, the present invention also relates to processes for making such compounds and the synthetic intermediates employed in these processes.

The invention further relates to alpha-2 adrenoreceptor antagonist and 5-hydroxytryptamine uptake inhibiting compositions comprising a pharmaceutical carrier and a therapeutically effective amount of a compound of claim 1.

In yet another aspect of the present invention, there is provided a method of treating diseases of the central nervous system including depression, aggression, obsessive compulsive disorders, panic attacks, hypochondriasis, memory disturbances, and anxiety, diseases of the vascular system including hypertension, glaucoma and migraine, metabolic disorders such as diabetes or feeding disorders, and alcoholism by administering to a host mammal in need of such treatment a therapeutically effective amount of a compound of claim 1.

DETAILED DESCRIPTION OF THE INVENTION

In one embodiment of the present invention, compounds are represented by Formula Ia:

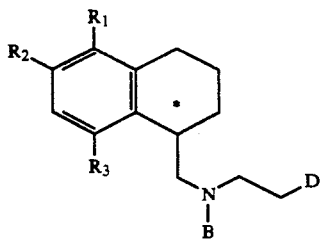

wherein B, R₁, R₂, R₃, and D are as defined above and the stereochemistry at the asymmetric center (*) is of the R configuration.

In another embodiment, B and R₇ are as defined above and D is selected from

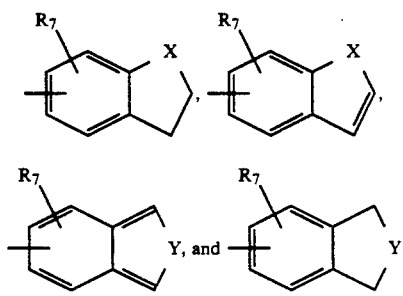

wherein X and Y are independently selected from >CH₂, >O, >S, >SO, >SO₂, and N—R₈ where R₈ is selected from hydrogen, lower alkyl, and alkylsulfonyl.

In another embodiment, B and R₆ are as defined above and D is selected from

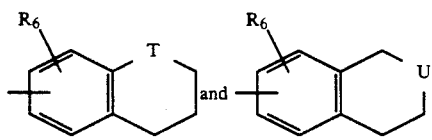

wherein T and U are independently selected from >CH₂, >O, >S, >SO, >SO₂, and >N—R₈ where R₈ is selected from hydrogen, lower alkyl, and alkylsulfonyl.

In another embodiment, B and R₆ are as defined above and D is selected from

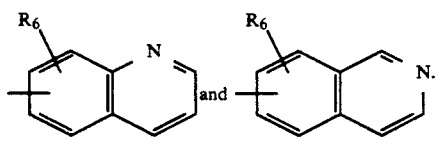

In another embodiment, B and R₇ are as defined above and D is selected from

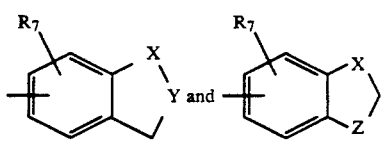

where X, Y and Z are independently selected from >O, >S, >SO, >SO₂, and >N—R₈ where R₈ is selected from hydrogen, lower alkyl, and alkylsulfonyl wherein not both X and Z are oxygen.

In another embodiment, B and R₇ are as defined above and D is selected from

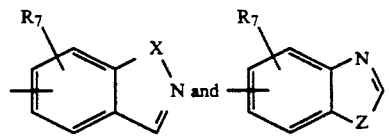

wherein X and Z are independently selected from >O, >S, >SO, >SO₂, and >N—R₈ where R₈ is selected from hydrogen, lower alkyl, and alkylsulfonyl.

In another embodiment, B and R₆ are as defined above and D is selected from

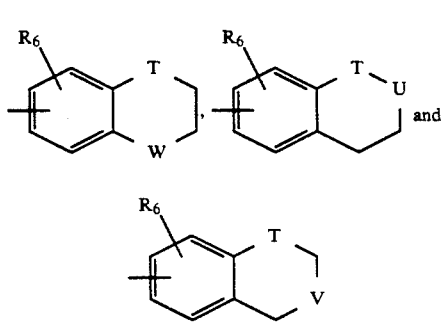

wherein T, U, V, and W are independently selected from >O, >S, >SO, >SO₂, and >N—R₈ where R₈ is selected from hydrogen, lower alkyl, and alkylsulfonyl with the provisos that 1) T and U cannot both be oxygen and 2) T and W cannot both be oxygen.

In another embodiment, B and R₆ are as defined above and D is selected from

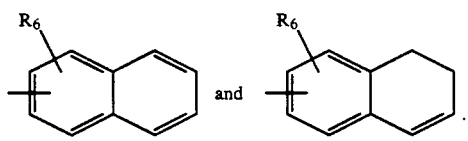

In another embodiment, B and R₆ are as defined above and D is selected from

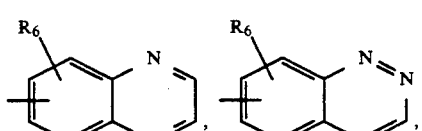

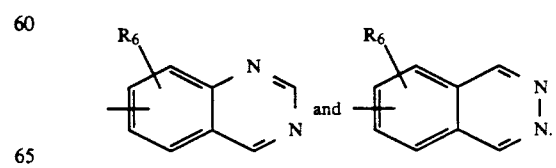

In another embodiment, B and R₇ are as defined above and D is selected from the group consisting of

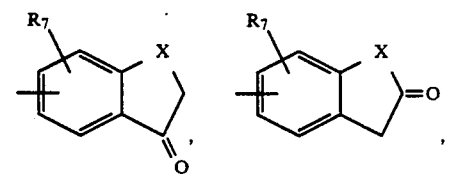

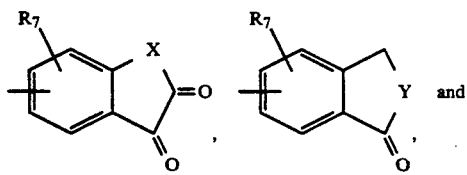

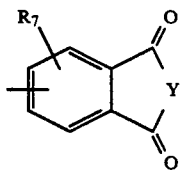

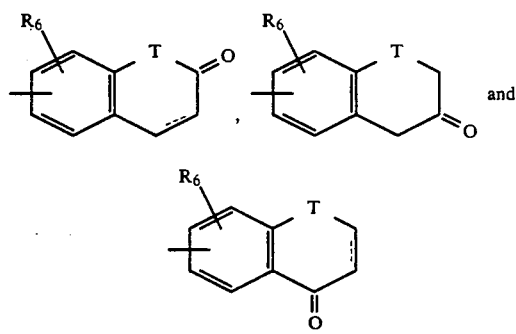

wherein X and Y are independently selected from >O, >S, >SO, >SO$_2$, and >N—R$_8$ where R$_8$ is selected from hydrogen, lower alkyl, and alkylsulfonyl.

In another embodiment, B and R$_6$ are as defined above and D is selected from

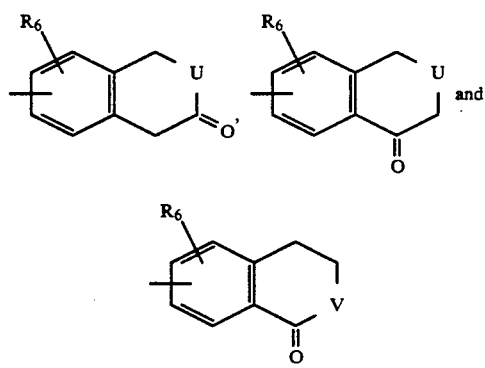

wherein T is independently selected from >O, >S, >SO, >SO$_2$, and >N—R$_8$ where R$_8$ is selected from hydrogen, lower alkyl, and alkylsulfonyl with optional double bonds as indicated by the dotted lines.

In another embodiment, B and R$_6$ are as defined above and D is selected from

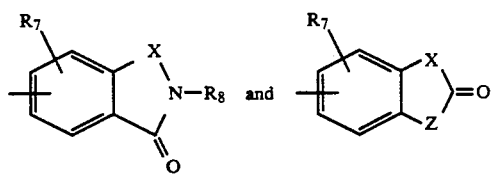

wherein U and Y are independently selected from >O, >S, >SO, >SO$_2$, and >N—R$_8$ where R$_8$ is selected from hydrogen, lower alkyl, and alkylsulfonyl.

In another embodiment, B and R$_7$ are as defined above and D is selected from

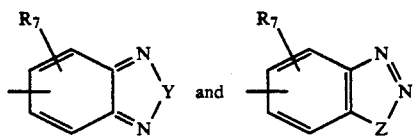

wherein X and Z are independently selected from >O, >S, >SO, >SO$_2$, and >N—R$_8$ where R$_8$ is selected from hydrogen, lower alkyl, and alkylsulfonyl.

In another embodiment, B and R$_7$ are as defined above and D is selected from

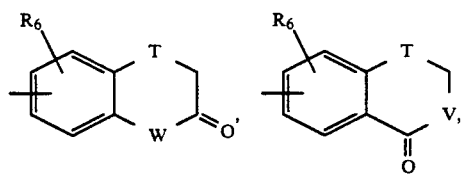

wherein Y and Z are independently selected from >C=O, >O, >S, >SO, >SO$_2$, and >N—R$_8$ where R$_8$ is selected from hydrogen, lower alkyl, and alkylsulfonyl.

In another embodiment, B and R$_6$ are as defined above and D is selected from the group consisting of

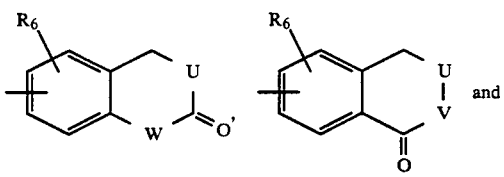

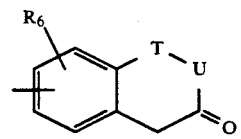

wherein T, U, V, and W are independently selected from >C=O, >O, >S, >SO, >SO$_2$, and >N—R$_8$ where R$_8$ is selected from hydrogen, lower alkyl, and alkylsulfonyl with the provisos that only one of T, U, V, and W is >C=O and only nitrogen heteroatoms may be adjacent to each other.

In another embodiment, B and R$_6$ are as defined above and D is selected from the group consisting of

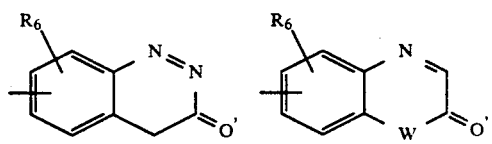

-continued

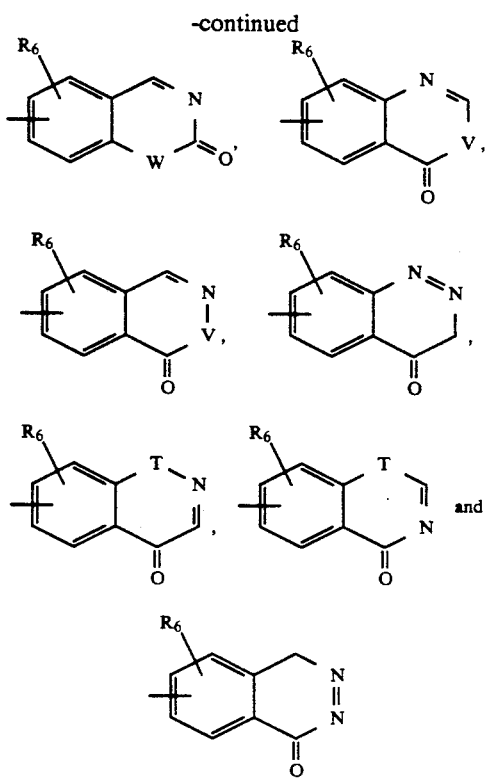

wherein T, U, V, and W are independently selected from >C=O, >O, >S, >SO, >SO$_2$, and >N—R$_8$ where R$_8$ is selected from hydrogen, lower alkyl, and alkylsulfonyl with the provisos that only one of T, U, V, and W is >C=O and only nitrogen heteroatoms may be adjacent to each other.

Examples of compounds falling within the scope of the present invention include, but are not limited to, the following:

N-[2-(2,3-Dihydro-benzo[b]thiophen-6-yl)-ethyl]-N-(5-methoxy-1,2,3,4-tetrahydro-naphthalen-1-ylmethyl)-N-methylamine;

N-[2-(3H-Inden-5-yl)-ethyl]-N-(5-methoxy-1,2,3,4-tetrahydro-naphthalen-1-ylmethyl)-N-methylamine;

N-[2-(1H-Indol-5-yl)-ethyl]-N-(5-methoxy-1,2,3,4-tetrahydro-naphthalen-1-ylmethyl)-N-methylamine;

N-(2-Benzo[b]thiophen-5-yl-ethyl)-N-(5-methoxy-1,2,3,4-tetrahydro-naphthalen-1-ylmethyl)-N-methylamine;

N-[2-(2H-Isoindol-5-yl)-ethyl]-N-(5-methoxy-1,2,3,4-tetrahydro-naphthalen-1-ylmethyl)-N-methylamine;

N-(2-Isobenzofuran-5-yl)-ethyl)-N-(5-methoxy-1,2,3,4-tetrahydro-naphthalen-1-ylmethyl)-N-methylamine;

N-[2-(1,3-Dihydro-benzo[c]thiophen-5-yl)-ethyl]-N-(5-methoxy-1,2,3,4-tetrahydro-naphthalen-1-ylmethyl)-N-methylamine;

N-[2-(1,2,3,4-Tetrahydro-quinolin-7-yl)-ethyl]-N-(5-methoxy-1,2,3,4-tetrahydro-naphthalen-1-ylmethyl)-N-methylamine;

N-[2-(1,2,3,4-Tetrahydro-quinolin-6-yl)-ethyl]-N-(5-methoxy-1,2,3,4-tetrahydro-naphthalen-1-ylmethyl)-N-methylamine;

N-(2-Chroman-7-yl-ethyl)-N-(5-methoxy-1,2,3,4-tetrahydro-naphthalen-1-ylmethyl)-N-methylamine;

N-(2-Chroman-6-yl-ethyl)-N-(5-methoxy-1,2,3,4-tetrahydro-naphthalen-1-ylmethyl)-N-methylamine;

N-(2-Thiochroman-7-yl-ethyl)-N-(5-methoxy-1,2,3,4-tetrahydro-naphthalen-1-ylmethyl)-N-methylamine;

N-(2-Thiochoman-6-yl-ethyl)-N-(5-methoxy-1,2,3,4-tetrahydro-naphthalen-1-ylmethyl)-N-methylamine;

N-[2-(1,2,3,4-Tetrahydro-isoquinolin-7-yl-ethyl)-N-(5-methoxy-1,2,3,4-tetrahydro-naphthalen-1-ylmethyl)-N-methylamine;

N-[2-(1,2,3,4-Tetrahydro-isoquinolin-6-yl-ethyl)-N-(5-methoxy-1,2,3,4-tetrahydro-naphthalen-1-ylmethyl)-N-methylamine;

N-(2-Isochroman-7-yl-ethyl)-N-(5-methoxy-1,2,3,4-tetrahydro-naphthalen-1-ylmethyl)-N-methylamine;

N-(2-Isochroman-6-yl-ethyl)-N-(5-methoxy-1,2,3,4-tetrahydro-naphthalen-1-ylmethyl)-N-methylamine;

N-(2-Isothiochroman-7-yl-ethyl)-N-(5-methoxy-1,2,3,4-tetrahydro-naphthalen-1-ylmethyl)-N-methylamine;

N-(2-Isothiochroman-6-yl-ethyl)-N-(5-methoxy-1,2,3,4-tetrahydro-naphthalen-1-ylmethyl)-N-methylamine;

N-[2-(3H-Indol-5-yl)-ethyl)-N-(5-methoxy-1,2,3,4-tetrahydro-naphthalen-1-ylmethyl)-N-methylamine;

N-[2-(3H-Indol-6-yl)-ethyl)-N-(5-methoxy-1,2,3,4-tetrahydro-naphthalen-1-ylmethyl)-N-methylamine;

N-[2-(3H-Isoindol-5-yl-ethyl)-N-(5-methoxy-1,2,3,4-tetrahydro-naphthalen-1-ylmethyl)-N-methylamine;

N-[2-(3H-Isoindol-6-yl-ethyl)-N-(5-methoxy-1,2,3,4-tetrahydro-naphthalen-1-ylmethyl)-N-methylamine;

N-[2-(1H-Indazol-5-yl-ethyl)-N-(5-methoxy-1,2,3,4-tetrahydro-naphthalen-1-ylmethyl)-N-methylamine;

N-[2-(1H-Indazol-6-yl-ethyl)-N-(5-methoxy-1,2,3,4-tetrahydro-naphthalen-1-ylmethyl)-N-methylamine;

N-[2-(2,3-Dihydro-1H-benzoimidazol-5-yl-ethyl)-N-(5-methoxy-1,2,3,4-tetrahydronaphthalen-1-ylmethyl)-N-methylamine;

N-[2-(2,3-Dihydro-benzothiazol-5-yl-ethyl)-N-(5-methoxy-1,2,3,4-tetrahydronaphthalen-1-ylmethyl)-N-methylamine;

N-[2-(2,3-Dihydro-benzoxazol-5-yl-ethyl)-N-(5-methoxy-1,2,3,4-tetrahydronaphthalen-1-ylmethyl)-N-methylamine;

N-[2-(1,3-Dihydro-benzo[c]isothiazol-5-yl-ethyl)-N-(5-methoxy-1,2,3,4-tetrahydronaphthalen-1-ylmethyl)-N-methylamine;

N-[2-(3H-Benzo[d][1,2]oxathiol-5-yl-ethyl)-N-(5-methoxy-1,2,3,4-tetrahydronaphthalen-1-ylmethyl)-N-methylamine;

N-[2-(1,3-Dihydro-benzo[c]isoxazol-5-yl-ethyl)-N-(5-methoxy-1,2,3,4-tetrahydronaphthalen-1-ylmethyl)-N-methylamine;

N-[2-(2,3-Dihydro-benzo[d]isothiazol-5-yl-ethyl)-N-(5-methoxy-1,2,3,4-tetrahydronaphthalen-1-ylmethyl)-N-methylamine;

N-[2-(2,3-Dihydro-benzo[d]isoxazol-5-yl-ethyl)-N-(5-methoxy-1,2,3,4-tetrahydronaphthalen-1-ylmethyl)-N-methylamine;

N-[2-(2,3-Dihydro-1H-indazol-5-yl-ethyl)-N-(5-methoxy-1,2,3,4-tetrahydronaphthalen-1-ylmethyl)-N-methylamine;

N-(2-Benzo[d]isoxazol-6-yl-ethyl)-N-(5-methoxy-1,2,3,4-tetrahydro-naphthalen-1-ylmethyl)-N-methylamine;

N-(2-Benzo[d]isothiazol-6-yl-ethyl)-N-(5-methoxy-1,2,3,4-tetrahydro-naphthalen-1-ylmethyl)-N-methylamine;

N-(2-Benzo[1,3]dithiol-5-yl-ethyl)-N-(5-methoxy-1,2,3,4-tetrahydro-naphthalen-1-ylmethyl)-N-methylamine;

N-(2-Benzo[1,3]oxathiol-6-yl-ethyl)-N-(5-methoxy-1,2,3,4-tetrahydro-naphthalen-1-ylmethyl)-N-methylamine;

N-[2-(1,2,3,4-Tetrahydro-quinozalin-6-yl-ethyl)-N-(5-methoxy-1,2,3,4-tetrahydro-naphthalen-1-ylmethyl)-N-methylamine;

N-[2-(1,4-Benzodioxan-6-yl-ethyl)-N-(5-methoxy-1,2,3,4-tetrahydro-naphthalen-1-ylmethyl)-N-methylamine;

N-[2-(1,4-Benzodithian-6-yl-ethyl)-N-(5-methoxy-1,2,3,4-tetrahydro-naphthalen-1-ylmethyl)-N-methylamine;

N-[2-(3,4-Dihydro-2H-benzo[1,4]oxazin-6-yl-ethyl)-N-(5-methoxy-1,2,3,4-tetrahydro-naphthalen-1-ylmethyl)-N-methylamine;

N-[2-(3,4-Dihydro-2H-benzo[1,4]oxazin-7-yl-ethyl)-N-(5-methoxy-1,2,3,4-tetrahydro-naphthalen-1-ylmethyl)-N-methylamine;

N-[2-(3,4-Dihydro-2H-benzo[1,4]thiazin-6-yl-ethyl)-N-(5-methoxy-1,2,3,4-tetrahydro-naphthalen-1-ylmethyl)-N-methylamine;

N-[2-(3,4-Dihydro-2H-benzo[1,4]thiazin-7-yl-ethyl)-N-(5-methoxy-1,2,3,4-tetrahydro-naphthalen-1-ylmethyl)-N-methylamine;

N-[2-(2,3-Dihydro-benzo[1,4]oxathiin-6-yl-ethyl)-N-(5-methoxy-1,2,3,4-tetrahydro-naphthalen-1-ylmethyl)-N-methylamine;

N-[2-(3,4-Dihydro-2H-benzo[1,4]oxathiin-7-yl-ethyl)-N-(5-methoxy-1,2,3,4-tetrahydro-naphthalen-1-ylmethyl)-N-methylamine;

N-[2-(1,2,3,4-Tetrahydro-cinnolin-7-yl-ethyl)-N-(5-methoxy-1,2,3,4-tetrahydro-naphthalen-1-ylmethyl)-N-methylamine;

N-[2-(1,2,3,4-Tetrahydro-cinnolin-6-yl-ethyl)-N-(5-methoxy-1,2,3,4-tetrahydro-naphthalen-1-ylmethyl)-N-methylamine;

N-[2-(3,4-Dihydro-benzo[c][1,2]dithiin-6-yl-ethyl)-N-(5-methoxy-1,2,3,4-tetrahydro-naphthalen-1-ylmethyl)-N-methylamine;

N-[2-(3,4-Dihydro-benzo[c][1,2]dithiin-7-yl-ethyl)-N-(5-methoxy-1,2,3,4-tetrahydro-naphthalen-1-ylmethyl)-N-methylamine;

N-[2-(1,2,3,4-Tetrahydro-quinazolin-7-yl-ethyl)-N-(5-methoxy-1,2,3,4-tetrahydro-naphthalen-1-ylmethyl)-N-methylamine;

N-[2-(1,2,3,4-Tetrahydro-quinazolin-6-yl-ethyl)-N-(5-methoxy-1,2,3,4-tetrahydro-naphthalen-1-ylmethyl)-N-methylamine;

N-[2-(1,3-Benzodioxan-7-yl-ethyl)-N-(5-methoxy-1,2,3,4-tetrahydro-naphthalen-1-ylmethyl)-N-methylamine;

N-[2-(1,3-Benzodioxan-6-yl-ethyl)-N-(5-methoxy-1,2,3,4-tetrahydro-naphthalen-1-ylmethyl)-N-methylamine;

N-[2-(1,3-Benzodithian-7-yl-ethyl)-N-(5-methoxy-1,2,3,4-tetrahydro-naphthalen-1-ylmethyl)-N-methylamine;

N-[2-(1,3-Benzodithian-6-yl-ethyl)-N-(5-methoxy-1,2,3,4-tetrahydro-naphthalen-1-ylmethyl)-N-methylamine;

N-[2-(4H-Benzo[d][1,3]oxathiin-7-yl-ethyl)-N-(5-methoxy-1,2,3,4-tetrahydro-naphthalen-1-ylmethyl)-N-methylamine;

N-[2-(4H-Benzo[d][1,3]oxathiin-6-yl-ethyl)-N-(5-methoxy-1,2,3,4-tetrahydro-naphthalen-1-ylmethyl)-N-methylamine;

N-[2-(1,4-Dihydro-2H-benzo[d][1,3]thiazin-7-yl-ethyl)-N-(5-methoxy-1,2,3,4-tetrahydro-naphthalen-1-ylmethyl)-N-methylamine;

N-[2-(1,4-Dihydro-2H-benzo[d][1,3]thiazin-6-yl-ethyl)-N-(5-methoxy-1,2,3,4-tetrahydro-naphthalen-1-ylmethyl)-N-methylamine;

N-[2-(1,4-Dihydro-2H-benzo[d][1,3]oxazin-7-yl-ethyl)-N-(5-methoxy-1,2,3,4-tetrahydro-naphthalen-1-ylmethyl)-N-methylamine;

N-[2-(1,4-Dihydro-2H-benzo[d][1,3]oxazin-6-yl-ethyl)-N-(5-methoxy-1,2,3,4-tetrahydro-naphthalen-1-ylmethyl)-N-methylamine;

N-[2-(3,4-Dihydro-2H-benzo[e][1,3oxazin-7-yl-ethyl)-N-(5-methoxy-1,2,3,4-tetrahydro-naphthalen-1-ylmethyl)-N-methylamine;

N-[2-(3,4-Dihydro-2H-benzo[e][1,3]oxazin-6-yl-ethyl)-N-(5-methoxy-1,2,3,4-tetrahydro-naphthalen-1-ylmethyl)-N-methylamine;

N-(2-Cinnolin-7-yl-ethyl)-N-(5-methoxy-1,2,3,4-tetrahydronaphthalen-1-ylmethyl)-N-methylamine;

N-(2-Cinnolin-6-yl-ethyl)-N-(5-methoxy-1,2,3,4-tetrahydronaphthalen-1-ylmethyl)-N-methylamine;

N-(2-Quinazolin-7-yl-ethyl)-N-(5-methoxy-1,2,3,4-tetrahydronaphthalen-1-ylmethyl)-N-methylamine;

N-(2-Quinazolin-6-yl-ethyl)-N-(5-methoxy-1,2,3,4-tetrahydronaphthalen-1-ylmethyl)-N-methylamine;

N-(2-Phthalazin-6-yl-ethyl)-N-(5-methoxy-1,2,3,4-tetrahydronaphthalen-1-ylmethyl)-N-methylamine;

6-{2-[(5-Methoxy-1,2,3,4-tetrahydro-naphthalen-1-ylmethyl)methyl-amino]-ethyl}-benzofuranon-3-one;

6-{2-[(5-Methoxy-1,2,3,4-tetrahydro-naphthalen-1-ylmethyl)methyl-amino]-ethyl}-1,2-dihydro-indol-3-one;

6-{2-[(5-Methoxy-1,2,3,4-tetrahydro-naphthalen-1-ylmethyl)methyl-amino]-ethyl}-benzo[b]thiophen-3-one;

6-{2-[(5-Methoxy-1,2,3,4-tetrahydro-naphthalen-1-ylmethyl)methyl-amino]-ethyl}-indan-1-one;

6-{2-[(5-Methoxy-1,2,3,4-tetrahydro-naphthalen-1-ylmethyl)methyl-amino]-ethyl}-indan-2-one;

6-{2-[(5-Methoxy-1,2,3,4-tetrahydro-naphthalen-1-ylmethyl)methyl-amino]-ethyl}-1,3-dihydro-indol-2-one;

6-{2-[(5-Methoxy-1,2,3,4-tetrahydro-naphthalen-1-ylmethyl)methyl-amino]-ethyl}-3H-benzofuran-2-one;

6-{2-[5-Methoxy-1,2,3,4-tetrahydro-naphthalen-1-ylmethyl)methyl-amino]-ethyl}-3H-benzo[b]thiophen-2-one;

6-{2-[(5-Methoxy-1,2,3,4-tetrahydro-naphthalen-1-ylmethyl)methyl-amino]-ethyl}-benzo[b]thiophen-2,3-dione;

6-{2-[(5-Methoxy-1,2,3,4-tetrahydro-naphthalen-1-ylmethyl)methyl-amino]-ethyl}-benzofuran-2,3-dione;

6-{2-[(5-Methoxy-1,2,3,4-tetrahydro-naphthalen-1-ylmethyl)methyl-amino]-ethyl}-1H-indole-2,3-dione;

5-{2-[(5-Methoxy-1,2,3,4-tetrahydro-naphthalen-1-ylmethyl)methyl-amino]-ethyl}-indan-1,2-dione;

5-{2-[(5-Methoxy-1,2,3,4-tetrahydro-naphthalen-1-ylmethyl)methyl-amino]-ethyl}-2,3-dihydro-isoindol-1-one;

5-{2-[(5-Methoxy-1,2,3,4-tetrahydro-naphthalen-1-ylmethyl)methyl-amino]-ethyl}-3H-isobenzofuran-1-one;

5-{2-[(5-Methoxy-1,2,3,4-tetrahydro-naphthalen-1-ylmethyl)methyl-amino]-ethyl}-3H-benzo[b]thiophen-1-one;

6-{2-[(5-Methoxy-1,2,3,4-tetrahydro-naphthalen-1-ylmethyl)methyl-amino]-ethyl}-benzo[c]thiophen-1,3-one;
7-{2-[(5-Methoxy-1,2,3,4-tetrahydro-naphthalen-1-ylmethyl)methyl-amino]-ethyl}-3,4-dihydro-1H-naphthalen-2one;
6-{2-[(5-Methoxy-1,2,3,4-tetrahydro-naphthalen-1-ylmethyl)methyl-amino]-ethyl}-3,4-dihydro-1H-naphthalen-2-one;
7-{2-[(5-Methoxy-1,2,3,4-tetrahydro-naphthalen-1-ylmethyl)methyl-amino]-ethyl}-3,4-dihydro-1H-quinolin-2-one;
6-{2-[(5-Methoxy-1,2,3,4-tetrahydro-naphthalen-1-ylmethyl)methyl-amino]-ethyl}-3,4-dihydro-1H-quinolin-2-one;
7-{2-[(5-Methoxy-1,2,3,4-tetrahydro-naphthalen-1-ylmethyl)methyl-amino]-ethyl}-chroman-2-one;
6-{2-[(5-Methoxy-1,2,3,4-tetrahydro-naphthalen-1-ylmethyl)methyl-amino]-ethyl}-chroman-2-one;
7-{2-[(5-Methoxy-1,2,3,4-tetrahydro-naphthalen-1-ylmethyl)methyl-amino]-ethyl}-thiochroman-2-one;
6-{2-[(5-Methoxy-1,2,3,4-tetrahydro-naphthalen-1-ylmethyl)methyl-amino]-ethyl}-thiochroman-2-one;
7-{2-[(5-Methoxy-1,2,3,4-tetrahydro-naphthalen-1-ylmethyl)methyl-amino]-ethyl}-1H-quinolin-2one;
6-{2-[(5-Methoxy-1,2,3,4-tetrahydro-naphthalen-1-ylmethyl)methyl-amino]-ethyl}-1H-quinolin-2-one;
7-{2-[(5-Methoxy-1,2,3,4-tetrahydro-naphthalen-1-ylmethyl)methyl-amino]-ethyl}-chromene-2-one;
6-{2-[(5-Methoxy-1,2,3,4-tetrahydro-naphthalen-1-ylmethyl)methyl-amino]-ethyl}-chromene-2-one;
7-{2-[(5-Methoxy-1,2,3,4-tetrahydro-naphthalen-1-ylmethyl)methyl-amino]-ethyl}-thiochromene-2-one;
5-{2-[(5-Methoxy-1,2,3,4-tetrahydro-naphthalen-1-ylmethyl)methyl-amino]-ethyl}-benzo[1,3]dioxol-2-one;
5-{2-[(5-Methoxy-1,2,3,4-tetrahydro-naphthalen-1-ylmethyl)methyl-amino]-ethyl}-3H-benzoxazol-2-one;
5-{2-[(5-Methoxy-1,2,3,4-tetrahydro-naphthalen-1-ylmethyl)methyl-amino]-ethyl}-benzo[1,3]oxathiol-2one;
5-{2-[(5-Methoxy-1,2,3,4-tetrahydro-naphthalen-1-ylmethyl)methyl-amino]-ethyl}-3H-benzothiazol-2one;
5-{2-[(5-Methoxy-1,2,3,4-tetrahydro-naphthalen-1-ylmethyl)methyl-amino]-ethyl}-benzo[1,3]dithiol-2-one;
5-{2-[(5-Methoxy-1,2,3,4-tetrahydro-naphthalen-1-ylmethyl)methyl-amino]-ethyl}-1,3-dihydro-benzimidazol-2one;
N-[2-(2H-Benzotriazol-5-yl)-ethyl]-N-(5-methoxy-1,2,3,4-tetrahydro-naphthalen-1-ylmethyl)-N-methylamine;
N-{2-(Benzo[1,2,5]oxadiazol-5-yl)-ethyl}-B-(5-methoxy-1,2,3,4-tetrahydro-naphthalen-1-ylmethyl)-N-methylamine;
N-{2-(Benzo[1,2,5]thiadiazol-5-yl)-ethyl]-N-(5-methoxy-1,2,3,4-tetrahydro-naphthalen-1-ylmethyl)-N-methylamine;
N-{2-(Benzo[1,2,3]thiadiazol-5-yl)-ethyl]-N-(5-methoxy-1,2,3,4-tetrahydro-naphthalen-1-ylmethyl)-N-methylamine;
N-{2-(Benzo[1,2,3]oxadiazol-5-yl)-ethyl]-N-(5-methoxy-1,2,3,4-tetrahydro-naphthalen-1-ylmethyl)-N-methylamine;
N-{2-(1H-Benzotriazol-5-yl)-ethyl]-N-(5-methoxy-1,2,3,4-tetrahydro-naphthalen-1-ylmethyl)-N-methylamine;
6-{2-[(5-Methoxy-1,2,3,4-tetrahydro-naphthalen-1-ylmethyl)methyl-amino]-ethyl}-thiochromene-2-one;
7-{2-[(5-Methoxy-1,2,3,4-tetrahydro-naphthalen-1-ylmethyl)methyl-amino]-ethyl}-1,4-dihydro-2H-quinolin-3one;
6-{2-[(5-Methoxy-1,2,3,4-tetrahydro-naphthalen-1-ylmethyl)methyl-amino]-ethyl}-1,4-dihydro-2H-quinolin-3one;
7-{2-[(5-Methoxy-1,2,3,4-tetrahydro-naphthalen-1-ylmethyl)methyl-amino]-ethyl}-chroman-3-one;
6-{2-[(5-Methoxy-1,2,3,4-tetrahydro-naphthalen-1-ylmethyl)methyl-amino]-ethyl}-chroman-3-one;
7-{2-[(5-Methoxy-1,2,3,4-tetrahydro-naphthalen-1-ylmethyl)methyl-amino]-ethyl}-thiochroman-3-one;
6-{2-[(5-Methoxy-1,2,3,4-tetrahydro-naphthalen-1-ylmethyl)methyl-amino]-ethyl}-thiochroman-3-one;
7-{2-[(5-Methoxy-1,2,3,4-tetrahydro-naphthalen-1-ylmethyl)methyl-amino]-ethyl}-3,4-dihydro-2H-naphthalen-1-one;
6-{2-[(5-Methoxy-1,2,3,4-tetrahydro-naphthalen-1-ylmethyl)methyl-amino]-ethyl}-3,4-dihydro-2H-naphthalen-1-one;
7-{2-[(5-Methoxy-1,2,3,4-tetrahydro-naphthalen-1-ylmethyl)methyl-amino]-ethyl}-2,3-dihydro-1H-quinolin-4-one;
6-{2-[(5-Methoxy-1,2,3,4-tetrahydro-naphthalen-1-ylmethyl)methyl-amino]-ethyl}-2,3-dihydro-1H-quinolin-4-one;
7-{2-[(5-Methoxy-1,2,3,4-tetrahydro-naphthalen-1-ylmethyl)methyl-amino]-ethyl}-chroman-4-one;
6-{2-[(5-Methoxy-1,2,3,4-tetrahydro-naphthalen-1-ylmethyl)methyl-amino]-ethyl}-chroman-4-one;
7-{2-[(5-Methoxy-1,2,3,4-tetrahydro-naphthalen-1-ylmethyl)methyl-amino]-ethyl}-thiochoman-4-one;
6-{2-[(5-Methoxy-1,2,3,4-tetrahydro-naphthalen-1-ylmethyl)methyl-amino]-ethyl}-thiochroman-4-one;
7-{2-[(5-Methoxy-1,2,3,4-tetrahydro-naphthalen-1-ylmethyl)methyl-amino]-ethyl}-1H-quinolin-4-one;
6-{2-[(5-Methoxy-1,2,3,4-tetrahydro-naphthalen-1-ylmethyl)methyl-amino]-ethyl}-1H-quinolin-4-one;
7-{2-[(5-Methoxy-1,2,3,4-tetrahydro-naphthalen-1-ylmethyl)methyl-amino]-ethyl}-chromen-4-one;
6-{2-[(5-Methoxy-1,2,3,4-tetrahydro-naphthalen-1-ylmethyl)methyl-amino]-ethyl}-chromen-4-one;
7-{2-[(5-Methoxy-1,2,3,4-tetrahydro-naphthalen-1-ylmethyl)methyl-amino]-ethyl}-thiochromen-4-one;
6-{2-[(5-Methoxy-1,2,3,4-tetrahydro-naphthalen-1-ylmethyl)methyl-amino]-ethyl}-thiochromen-4-one;
7-{2-[(5-Methoxy-1,2,3,4-tetrahydro-naphthalen-1-ylmethyl)methyl-amino]-ethyl}-1,4-dihydro-2H-isoquinolin-3-one;
7-{2-[(5-Methoxy-1,2,3,4-tetrahydro-naphthalen-1-ylmethyl)methyl-amino]-ethyl}-isochroman-3-one;
7-{2-[(5-Methoxy-1,2,3,4-tetrahydro-naphthalen-1-ylmethyl)methyl-amino]-ethyl}-isothiochroman-3-one;
7-{2-[(5-Methoxy-1,2,3,4-tetrahydro-naphthalen-1-ylmethyl)methyl-amino]-ethyl}-isochroman-4-one;
6-{2-[(5-Methoxy-1,2,3,4-tetrahydro-naphthalen-1-ylmethyl)methyl-amino]-ethyl}-isochroman-4-one;
7-{2-[(5-Methoxy-1,2,3,4-tetrahydro-naphthalen-1-ylmethyl)methyl-amino]-ethyl}-2,3-dihydro-1H-isoquinolin-4-one;

6-{2-[(5-Methoxy-1,2,3,4-tetrahydro-naphthalen-1-ylmethyl)methyl-amino]-ethyl}-2,3-dihydro-1H-isoquinolin-4-one;

6-{2-[(5-Methoxy-1,2,3,4-tetrahydro-naphthalen-1-ylmethyl)methyl-amino]-ethyl}-3,4-dihydro-2H-isoquinolin-1-one;

6-{2-[(5-Methoxy-1,2,3,4-tetrahydro-naphthalen-1-ylmethyl)methyl-amino]-ethyl}-3,4-dihydro-2H-isochroman-1-one;

6-{2-[(5-Methoxy-1,2,3,4-tetrahydro-naphthalen-1-ylmethyl)methyl-amino]-ethyl}-3,4-dihydro-2H-isothiochroman-1-one;

6-{2-[(5-Methoxy-1,2,3,4-tetrahydro-naphthalen-1-ylmethyl)methyl-amino]-ethyl}-3,4-dihydro-2-isothiochromen-1-one;

6-{2-[(5-Methoxy-1,2,3,4-tetrahydro-naphthalen-1-ylmethyl)methyl-amino]-ethyl}-isochromen-1-one;

6-{2-[(5-Methoxy-1,2,3,4-tetrahydro-naphthalen-1-ylmethyl)methyl-amino]-ethyl}-2H-isoquinolin-1-one;

6-{2-[(5-Methoxy-1,2,3,4-tetrahydro-naphthalen-1-ylmethyl)methyl-amino]-ethyl}-4H-isoquinolin-3-one;

6-{2-[(5-Methoxy-1,2,3,4-tetrahydro-naphthalen-1-ylmethyl)methyl-amino]-ethyl}-3,4-dihydro-2H-phthalazin-1one;

7-{2-[(5-Methoxy-1,2,3,4-tetrahydro-naphthalen-1-ylmethyl)methyl-amino]-ethyl}-1H-benzo[d][1,2]oxazin-4-one;

7-{2-[(5-Methoxy-1,2,3,4-tetrahydro-naphthalen-1-ylmethyl)methyl-amino]-ethyl}-1H-benzo[d][1,2]-thiazin-4-one;

6-{2-[(5-Methoxy-1,2,3,4-tetrahydro-naphthalen-1-ylmethyl)methyl-amino]-ethyl}-4H-benzo[d][1,2]oxathiin-1-one;

6-{2-[(5-Methoxy-1,2,3,4-tetrahydro-naphthalen-1-ylmethyl)methyl-amino]-ethyl}-3,4-dihydro-benzo[d][1,2]oxazin-1-one;

7-{2-[(5-Methoxy-1,2,3,4-tetrahydro-naphthalen-1-ylmethyl)methyl-amino]-ethyl}-benzo[1,3]dioxin-4-one;

7-{2-[(5-Methoxy-1,2,3,4-tetrahydro-naphthalen-1-ylmethyl)methyl-amino]-ethyl}-1,2-dihydro-benzo[d][1,3]oxazin-4-one;

7-{2-[(5-Methoxy-1,2,3,4-tetrahydro-naphthalen-1-ylmethyl)methyl-amino]-ethyl}-benzo[d][1,3]oxazinin-4-one;

7-{2-[(5-Methoxy-1,2,3,4-tetrahydro-naphthalen-1-ylmethyl)methyl-amino]-ethyl}-benzo[d][1,3]oxathiin-4-one;

6-{2-[(5-Methoxy-1,2,3,4-tetrahydro-naphthalen-1-ylmethyl)methyl-amino]-ethyl}-benzo[d][1,3]oxathiin-4-one;

7-{2-[(5-Methoxy-1,2,3,4-tetrahydro-naphthalen-1-ylmethyl)methyl-amino]-ethyl}-2,3-dihydro-benzo[e][1,3]thiazin-4-one;

7-{2-[(5-Methoxy-1,2,3,4-tetrahydro-naphthalen-1-ylmethyl)methyl-amino]-ethyl}-benzo[e][1,3]thiazin-4-one;

7-{2-[(5-Methoxy-1,2,3,4-tetrahydro-naphthalen-1-ylmethyl)methyl-amino]-ethyl}-2,3-dihydro-1H-quinazolin-4-one;

7-{2-[(5-Methoxy-1,2,3,4-tetrahydro-naphthalen-1-ylmethyl)methyl-amino]-ethyl}-3H-quinazolin-4-one;

7-{2-[(5-Methoxy-1,2,3,4-tetrahydro-naphthalen-1-ylmethyl)methyl-amino]-ethyl}-benzo[d][1,3]thiazin-4-one;

7-{2-[(5-Methoxy-1,2,3,4-tetrahydro-naphthalen-1-ylmethyl)methyl-amino]-ethyl}-1,2-dihydro-benzo[d][1,3]thiazin-4-one;

7-{2-[(5-Methoxy-1,2,3,4-tetrahydro-naphthalen-1-ylmethyl)methyl-amino]-ethyl}-benzo[d][1,3]oxathiin-4-one;

7-{2-[(5-Methoxy-1,2,3,4-tetrahydro-naphthalen-1-ylmethyl)methyl-amino]-ethyl}-benzo[1,3]dithiin-4-one;

6-{2-[(5-Methoxy-1,2,3,4-tetrahydro-naphthalen-1-ylmethyl)methyl-amino]-ethyl}-benzo[1,4]dithiin-2-one;

6-{2-[(5-Methoxy-1,2,3,4-tetrahydro-naphthalen-1-ylmethyl)methyl-amino]-ethyl}-benzo[1,4]oxathiin-2-one;

6-{2-[(5-Methoxy-1,2,3,4-tetrahydro-naphthalen-1-ylmethyl)methyl-amino]-ethyl}-4H-benzo[1,4]thiazin-3-one;

6-{2-[(5-Methoxy-1,2,3,4-tetrahydro-naphthalen-1-ylmethyl)methyl-amino]-ethyl}-3,4-dihydro-1H-quinoxalin-2-one;

6-{2-[(5-Methoxy-1,2,3,4-tetrahydro-naphthalen-1-ylmethyl)methyl-amino]-ethyl}-3,4-dihydro-benzo[1,4]oxazin-2-one;

6-{2-[(5-Methoxy-1,2,3,4-tetrahydro-naphthalen-1-ylmethyl)methyl-amino]-ethyl}-3,4-dihydro-benzo[1,4]thiazin-2-one;

6-{2-[(5-Methoxy-1,2,3,4-tetrahydro-naphthalen-1-ylmethyl)methyl-amino]-ethyl}-benzo[1,4]thiazin-2-one;

6-{2-[(5-Methoxy-1,2,3,4-tetrahydro-naphthalen-1-ylmethyl)methyl-amino]-ethyl}-benzo[1,4]oxazin-2-one;

6-{2-[(5-Methoxy-1,2,3,4-tetrahydro-naphthalen-1-ylmethyl)methyl-amino]-ethyl}-1H-quinoxalin-2-one;

6-{2-[(5-Methoxy-1,2,3,4-tetrahydro-naphthalen-1-ylmethyl)methyl-amino]-ethyl}-4H-benzo[1,4]oxazin-3-one;

7-{2-[(5-Methoxy-1,2,3,4-tetrahydro-naphthalen-1-ylmethyl)methyl-amino]-ethyl}-benzo[1,4]oxathiin-3-one;

6-{2-[(5-Methoxy-1,2,3,4-tetrahydro-naphthalen-1-ylmethyl)methyl-amino]-ethyl}-4H-benzo[1,3]dithiin-2-one;

6-{2-[(5-Methoxy-1,2,3,4-tetrahydro-naphthalen-1-ylmethyl)methyl-amino]-ethyl}-4H-benzo[d][1,3]oxathiin-2-one;

6-{2-[(5-Methoxy-1,2,3,4-tetrahydro-naphthalen-1-ylmethyl)methyl-amino]-ethyl}-3,4-dihydro-benzo[e][1,3]thiazin-2-one;

6-{2-[(5-Methoxy-1,2,3,4-tetrahydro-naphthalen-1-ylmethyl)methyl-amino]-ethyl}-benzo[e]1,3]thiazin-2-one;

6-{2-[(5-Methoxy-1,2,3,4-tetrahydro-naphthalen-1-ylmethyl)methyl-amino]-ethyl}-1H-quinazolin-2-one;

6-{2-[(5-Methoxy-1,2,3,4-tetrahydro-naphthalen-1-ylmethyl)methyl-amino]-ethyl}-benzo[e][1,3]oxazin-2-one;

6-{2-[(5-Methoxy-1,2,3,4-tetrahydro-naphthalen-1-ylmethyl)methyl-amino]-ethyl}-3,4-dihydro-1H-quinazolin-2-one;

6-{2-[(5-Methoxy-1,2,3,4-tetrahydro-naphthalen-1-ylmethyl)methyl-amino]-ethyl}-3,4-dihydro-benzo[e][1,3]oxazin-2-one;

6-{2-[(5-Methoxy-1,2,3,4-tetrahydro-naphthalen-1-ylmethyl)methyl-amino]-ethyl}-4H-benzo[1,3]dioxin-2-one;

6-{2-[(5-Methoxy-1,2,3,4-tetrahydro-naphthalen-1-ylmethyl)methyl-amino]-ethyl}-4H-benzo[d][1,3]oxathiin-2-one;

7-{2-[(5-Methoxy-1,2,3,4-tetrahydro-naphthalen-1-ylmethyl)methyl-amino]-ethyl}-1,4-dihydro-benzo[c][1,2]thiazin-3-one;

7-{2-[(5-Methoxy-1,2,3,4-tetrahydro-naphthalen-1-ylmethyl)methyl-amino]-ethyl}-1,4-dihydro-benzo[c][1,2]oxazin-3-one;

7-{2-[(5-Methoxy-1,2,3,4-tetrahydro-naphthalen-1-ylmethyl)methyl-amino]-ethyl}-1,4-dihydro-2H-cinnolin-3-one;

7-{2-[(5-Methoxy-1,2,3,4-tetrahydro-naphthalen-1-ylmethyl)methyl-amino]-ethyl}-4H-benzo[e][1,2]oxazin-3-one;

6-{2-[(5-Methoxy-1,2,3,4-tetrahydro-naphthalen-1-ylmethyl)methyl-amino]-ethyl}-4H-benzo[e][1,2]oxazin-3-one;

7-{2-[(5-Methoxy-1,2,3,4-tetrahydro-naphthalen-1-ylmethyl)methyl-amino]-ethyl}-1H-isoquinoline-4-one;

7-{2-[(5-Methoxy-1,2,3,4-tetrahydro-naphthalen-1-ylmethyl)methyl-amino]-ethyl}-benzo[d][1,2]oxazin-1-one;

6-{2-[(5-Methoxy-1,2,3,4-tetrahydro-naphthalen-1-ylmethyl)methyl-amino]-ethyl}-2H-phthalazin-1-one;

6-{2-[(5-Methoxy-1,2,3,4-tetrahydro-naphthalen-1-ylmethyl)methyl-amino]-ethyl}-benzo[d][1,2]thiazin-1-one;

7-{2-[(5-Methoxy-1,2,3,4-tetrahydro-naphthalen-1-ylmethyl)methyl-amino]-ethyl}-benzo[d][1,3]thiazin-4-one;

7-{2-[(5-Methoxy-1,2,3,4-tetrahydro-naphthalen-1-ylmethyl)methyl-amino]-ethyl}-benzo[d][1,3]oxazin-4-one;

7-{2-[(5-Methoxy-1,2,3,4-tetrahydro-naphthalen-1-ylmethyl)methyl-amino]-ethyl}-3H-quinazolin-4-one;

7-{2-[(5-Methoxy-1,2,3,4-tetrahydro-naphthalen-1-ylmethyl)methyl-amino]-ethyl}-3H-quinolin-4-one;

7-{2-[(5-Methoxy-1,2,3,4-tetrahydro-naphthalen-1-ylmethyl)methyl-amino]-ethyl}-3H-cinnolin-4-one;

6-{2-[(5-Methoxy-1,2,3,4-tetrahydro-naphthalen-1-ylmethyl)methyl-amino]-ethyl}-benzo[e][1,2]thiazin-2-one;

6-{2-[(5-Methoxy-1,2,3,4-tetrahydro-naphthalen-1-ylmethyl)methyl-amino]-ethyl}-benzo[e][1,3]oxazin-2-one;

7-{2-[(5-Methoxy-1,2,3,4-tetrahydro-naphthalen-1-ylmethyl)methyl-amino]-ethyl}-1H-quinazolin-2-one;

6-{2-[(5-Methoxy-1,2,3,4-tetrahydro-naphthalen-1-ylmethyl)methyl-amino]-ethyl}-1H-quinoxalin-2-one;

6-{2-[(5-Methoxy-1,2,3,4-tetrahydro-naphthalen-1-ylmethyl)methyl-amino]-ethyl}-benzo[1,4]thiazin-2-one;

6-{2-[(5-Methoxy-1,2,3,4-tetrahydro-naphthalen-1-ylmethyl)methyl-amino]-ethyl}-benzo[1,4]oxazin-2-one;

7-{2-[(5-Methoxy-1,2,3,4-tetrahydro-naphthalen-1-ylmethyl)methyl-amino]-ethyl}-4H-cinnolin-3-one;

7-{2-[(5-Methoxy-1,2,3,4-tetrahydro-naphthalen-1-ylmethyl)methyl-amino]-ethyl}-4H-benzo[e][1,2]thiazin-3-one;

6-{2-[(5-Methoxy-1,2,3,4-tetrahydro-naphthalen-1-ylmethyl)methyl-amino]-ethyl}-4H-phthalazin-1-one;

7-{2-[(5-Methoxy-1,2,3,4-tetrahydro-naphthalen-1-ylmethyl)methyl-amino]-ethyl}-1H-cinnolin-4-one;

7-{2-[(5-Methoxy-1,2,3,4-tetrahydro-naphthalen-1-ylmethyl)methyl-amino]-ethyl}-benzo[e][1,2]oxazin-4-one;

7-{2-[(5-Methoxy-1,2,3,4-tetrahydro-naphthalen-1-ylmethyl)methyl-amino]-ethyl}-benzo[e][1,2]thiazin-4-one;

7-{2-[(5-Methoxy-1,2,3,4-tetrahydro-naphthalen-1-ylmethyl)methyl-amino]-ethyl}-benzo[e][1,3thiazin-4-one;

7-{2-[(5-Methoxy-1,2,3,4-tetrahydro-naphthalen-1-ylmethyl)methyl-amino]-ethyl}-benzo[e][1,3]oxazin-4-one; and 7-{2-[(5-Methoxy-1,2,3,4-tetrahydro-naphthalen-1-ylmethyl)methyl-amino]-ethyl}-1H-quinazolin-4-one.

Preferred compounds of the present invention include, but are not limited to, the following:

N-[2-(2,3-Dihydrobenzofuran-5-yl)ethyl]-N-[(R)-(+)-5-methoxy-1,2,3,4-tetrahydronaphthalen-1-ylmethyl]-N-methylamine;

N-[2-(Benzofuran-5-yl)ethyl]-N-[5-methoxy-1,2,3,4-tetrahydronaphthalen-1-ylmethyl]-N-methylamine;

N-[2-(2,3-Dihydrobenzofuran-5-yl)ethyl]-N-[(R)-(+)-5-methoxy-8-fluoro-1,2,3,4-tetrahydronaphthalen-1-ymethyl]-N-methylamine;

N-[2-(Benzofuran-6-yl)ethyl]-N-[(R)-(+)-5-methoxy-1,2,3,4-tetrahydronaphthalen-1-ylmethyl]-N-methylamine;

N-[2-(2,3-Dihydrobenzofuran-5-yl)ethyl]-N-[(R)-(+-5-ethoxy-1,2,3,4-tetrahydronaphthalen-1-ylmethyl]-N-methylamine;

N-[2-(2,3-Dihydrobenzofuran-6-yl)ethyl]-N-[(R)-(+)-5-methoxy-1,2,3,4-tetrahydronaphthalen-1-ylmethyl]-N-methylamine hydrochloride;

N-[2-(2,3-Dihydrobenzofuran-5-yl)ethyl]-N-[(R)-(+)-5,6-methylenedioxy-1,2,3,4-tetrahydronaphthalen-1-ylmethyl]-N-methylamine;

N-[2-(2,3-Dihydrobenzo[b]thien-5-yl)ethyl]-N-[(R)-(+)-5-methoxy-1,2,3,4-tetrahydronaphthalen-1-ylmethyl]-N-methylamine;

N-[2-(Benzimidazol-5-yl)ethyl]-N-[(r)-(+)-5-methoxy-1,2,3,4-tetrahydronaphthalen-1-ylmethyl]-N-methylamine;

N-[2-(Benzoxazol-6-yl)ethyl]-N-[(R)-(+)-5-methoxy-1,2,3,4-tetrahydronaphthalen-1-ylmethyl]-N-methylamine;

N-[2-(Benzoxazol-5-yl)ethyl]-N-[(R)-(+)-5-methoxy-1,2,3,4-tetrahydronaphthalen-1-ylmethyl]-N-methylamine;

N-[2-(Benzoxazol-6-yl)ethyl]-N-[(R)-(+)-8-fluoro-5-methoxy-1,2,3,4-tetrahydronaphthalen-1-ylmethyl]-N-methylamine;

N-[2-(Benzoxazol-5-yl)ethyl]-N-[(R)-(+)-8-fluoro-6-methoxy-1,2,3,4-tetrahydronaphthalen-1-ylmethyl]-N-methylamine;

N-[2-([4H]-2,3-Dihydrobenzopyran-6-yl)ethyl]-N-[(R)-(+)-5-methoxy-1,2,3,4-tetrahydronaphthalen-1-ylmethyl]-N-methylamine;

N-[2-(Indan-5-yl)ethyl]-N-[(R)-(+)-5-methoxy-1,2,3,4-tetrahydronaphthalen-1-ylmethyl]-N-methylamine;

N-[2-(N-Methanesulfonamido-2,3-dihydroindol-5-yl)ethyl]-N-[(R)-(+)-5-methoxy-1,2,3,4-tetrahydronaphthalen-1-ylmethyl]-N-methylamine;

N-[2-(Benzimidazol-5-yl)ethyl]-N-[(R)-(+)-8-fluoro-5-methoxy-1,2,3,4-tetrahydronaphthalen-1-ylmethyl]-N-methylamine;

N-[2,3-Dihydroindol-5-yl)ethyl]-N-[(R)-(+)-5-methoxy-1,2,3,4-tetrahydronaphthalen-1-ylmethyl]-N-methylamine;

N-[2-(2-Chlorobenzothiazol-6-yl)ethyl]-N-[(R)-(+)-5-methoxy-1,2,3,4-tetrahydronaphthalen-1-ylmethyl]-N-methylamine;

N-[2-(Quinoxalin-6-yl)ethyl]-N-[(R)-(+)-5-methoxy-1,2,3,4-tetrahydronaphthalen-1-ylmethyl]-N-methylamine;

N-[2-(Quinolin-6-yl)ethyl]-N-[(R)-(+)-5-methoxy-1,2,3,4-tetrahydronaphthalen-1-ylmethyl]-N-methylamine;

N-[2-(Quinolin-7-yl)ethyl]-N-[(R)-(+)-5-methoxy-1,2,3,4-tetrahydronaphthalen-1-ylmethyl]-N-methylamine;

N-[2-(isoquinolin-6-yl)ethyl]-N-[(R)-(+)-5-methoxy-1,2,3,4-tetrahydronaphthalen-1-ylmethyl]-N-methylamine;

N-[2-(Isoquinolin-7-yl)ethyl]-N-[(R)-(+)-5-methoxy-1,2,3,4-tetrahydronaphthalen-1-ylmethyl]-N-methylamine;

N-[2-(N-Methanesulfonamido-2,3-dihydroindol-6-yl)ethyl]-N-[(R)-(+)-5-methoxy-1,2,3,4-tetrahydronaphthalen-1-ylmethyl]-N-methylamine;

N-[2-(N-Propanesulfonamido-2,3-dihydroindol-6-yl)ethyl]-N-[(R)-(+)-5-methoxy-1,2,3,4-tetrahydronaphthalen-1-ylmethyl]-N-methylamine;

N-[2-(N-Isobutanesulfonamido-2,3-dihydroindol-6-yl)ethyl]-N-[(R)-(+)-5-methoxy-1,2,3,4-tetrahydronaphthalen-1-ylmethyl]-N-methylamine;

N-[2-(N-Methyl-2,3-dihydroindol-5-yl)ethyl]-N-[(R)-(+)-5-methoxy-1,2,3,4-tetrahydronaphthalen-1-ylmethyl]-N-methylamine;

N-[2-(N-Methyl-2,3-dihydroindol-6-yl)ethyl]-N-[(R)-(+)-5-methoxy-1,2,3,4-tetrahydronaphthalen-1-ylmethyl]-N-methylamine;

N-[2-(2,3-Dihydroindol-6-yl)ethyl]-N-[(R)-(+)-5-methoxy-1,2,3,4-tetrahydronaphthalen-1-ylmethyl]-N-methylamine;

N-[2-(2,3-Dihydroindol-5-yl)ethyl]-N-[(R)-(+)-5-methoxy-1,2,3,4-tetrahydronaphthalen-1-ylmethyl]-N-methylamine;

N-[2-(Indol-6-yl)ethyl]-N-[(R)-(+)-5-methoxy-1,2,3,4-tetrahydronaphthalen-1-ylmethyl]-N-methylamine;

N-[2-(N-Methanesulfondamido-1,3-dihydroisoindol-5-yl)ethyl]-N-[(R)-(+)-5-methoxy-1,2,3,4-tetrahydronaphthalen-1-ylmethyl]-N-methylamine;

N-[2-(N-Methyl-1,3-dihydroisoindol-5-yl)ethyl]-N-[(R)-(+)-5-methoxy-1,2,3,4-tetrahydronaphthalen-1-ylmethyl]-N-methylamine;

N-[2-(1,3-Dihydroisoindol-5-yl)ethyl]-N-[(R)-(+)-5-methoxy-1,2,3,4-tetrahydronaphthalen-1-ylmethyl]-N-methylamine;

N-[2-(Benzothiazol-6-yl)ethyl]-N-[(R)-(+)-5-methoxy-1,2,3,4-tetrahydronaphthalen-1-ylmethyl]-N-methylamine;

N-[2-(2-Chlorobenzothiazol-5-yl)ethyl]-N-[(R)-(+)-5-methoxy-1,2,3,4-tetrahydronaphthalen-1-ylmethyl]-N-methylamine;

N-[2-(Benzothiazol-5-yl)ethyl]-N-[(R)-(+)-5-methoxy-1,2,3,4-tetrahydronaphthalen-1-ylmethyl]-N-methylamine;

N-[2-(Benzothiophen-5-yl)ethyl]-N-[(R)-(+)-5-methoxy-1,2,3,4-tetrahydronaphthalen-1-ylmethyl]-N-methylamine;

N-[2-(2,3-Dihydro-benzothiazol-6-yl)ethyl]-N-[(R)-(+)-5-methoxy-1,2,3,4-tetrahydronaphthalen-1-ylmethyl]-N-methylamine;

N-[2-(Benzothiophen-6-yl)ethyl]-N-[(R)-(+)-5-methoxy-1,2,3,4-tetrahydronaphthalen-1-ylmethyl]-N-methylamine;

N-[2-(1-Oxo-2,3-dihydrobenzothiophen-5-yl)ethyl]-N-[(R)-(+)-5-methoxy-1,2,3,4-tetrahydronaphthalen-1-ylmethyl]-N-methylamine;

N-[2-(1,1-Dioxo-2,3-dihydrobenzothiophen-5-yl)ethyl]-N-[(R)-(+)-5-methoxy-1,2,3,4-tetrahydronaphthalen-1-ylmethyl]-N-methylamine;

N-[2-(1-Oxo-2,3-dihydrobenzothiophen-6-yl)ethyl]-N-[(R)-(+)-5-methoxy-1,2,3,4-tetrahydronaphthalen-1-ylmethyl]-N-methylamine;

N-[2-(1,1-Dioxo-2,3-dihydrobenzothiophen-6-yl)ethyl]-N-[(R)-(+)-5-methoxy-1,2,3,4-tetrahydronaphthalen-1-ylmethyl]-N-methylamine;

N-[2-(1,3-Dihydro-isobenzofuran-5-yl)-ethyl]-N-[(R)-(+)-5-methoxy-1,2,3,4-tetrahydronaphthalen-1-ylmethyl]-N-methylamine;

N-[2-(Benzo[1,3]oxathiol-5-yl)-ethyl]-N-[(R)-(+)-5-methoxy-1,2,3,4-tetrahydronaphthalen-1-ylmethyl]-N-methylamine;

N-[2-(2-Amino-benzothiazol-5-yl)-ethyl]-N-[(R)-(+)-5-methoxy-1,2,3,4-tetrahydronaphthalen-1-ylmethyl]-N-methylamine;

N-[(2-Benzofuran-5-yl)-ethyl]-N-{(R)-(+)-5-methoxy-1,2,3,4-tetrahydronaphthalen-1-ylmethyl]-N-methylamine;

N-[2-(N-Methyl-2,3-dihydro-1H-indol-5-yl)-ethyl]-N-[(R)-(+)-5-methoxy-1,2,3,4-tetrahydronaphthalen-1-ylmethyl]-N-methylamine; and 5-{2-[((R)-(+)-5-Methoxy-1,2,3,4-tetrahydro-naphthalen-1-ylmethyl)methyl-amino]-ethyl}-1,3-dihydro-indol-2-one.

As used throughout this specification and the appended claims, the following terms have the meanings ascribed to them:

The term "lower alkyl" as used herein refers to straight or branched chain saturated hydrocarbon radicals having from one to six carbon atoms. Representative examples of lower alkyl groups include methyl, ethyl, n-propyl, iso-propyl, n-butyl, sec-butyl, iso-butyl, tert-butyl, and the like.

The term "lower alkoxy" as used herein refers to a lower alkyl group, as defined herein, which is bonded to the parent molecular moiety through an oxygen atom. Representative examples of lower alkoxy groups include methoxy, ethoxy, tert-butoxy, and the like.

The term "thioalkyloxy" as used herein refers to a lower alkyl group, as defined herein, which is bonded to the parent molecular moiety through a sulfur atom. Representative examples of thioalkyloxy groups include methylthio, ethylthio, isopropylthio, and the like.

The term "alkylamino" as used herein refers to one or two lower alkyl groups, as defined herein, which are bonded to the parent molecular moiety through a nitrogen atom. Representative examples of alkylamino groups include methylamino, dimethylamino, ethylamino, diethylamino, isopropylamino, and the like.

The term "alkylsulfonyl" as used herein refers to a lower alkyl group bonded to the parent molecular moiety through a sulfonyl ($-SO_2-$) group. Representative examples of alkylsulfonyl groups include methanesulfonyl, ethanesulfonyl, isopropylsulfonyl, and the like.

The term "alkylsulfonylamino" as used herein refers to a lower alkyl group bonded to the parent molecular moiety through a sulfonylamino ($-SO_2NR-$) group in which R can be hydrogen or lower alkyl. Representative examples of alkylsulfonylamino groups include methanesulfonamido, ethanesulfonamido, N-methylmethanesulfonamido, and the like.

The term "halo" or "halogen" as used herein means fluorine, iodine, bromine, or chlorine.

The term "methylenedioxy" or "ethylenedioxy" as used herein refers to either a methylene group, —CH$_2$—, or an ethylene group, —CH$_2$CH$_2$—, attached to the parent molecular moiety through oxygen atoms to form either five or six membered rings.

The term "substituted phenyl" as used herein refers to a phenyl ring with one, two, or three substituents independently selected from lower alkyl, halo, hydroxy, lower alkoxy, amino, and thioalkyloxy.

The term "pharmaceutically acceptable salts" refers to the pharmaceutically acceptable, relatively nontoxic, inorganic or organic acid addition salts of the compounds of the present invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, methanesulfonate, stearate, laurate, borate, benzoate, lactate, phosphate, tolsylate, citrate, maleate, fumarate, succinate, tartrate, napsylate, and the like. Those compounds having more than one basic site can be isolated as bis-salts, for example, dihydrochloride, bis0methanesulfonate, and the like.

The standard chirality descriptors "R" and "S" are used to indicate an isomerically pure center, "RS" to indicate a mixture, and "R/S" to indicate a single pure isomer of undetermined configuration. The assignment of "R" and "S" depends on the priority ranking of atoms or groups attached to the asymmetric center as determined by the Cahn-Ingold-Prelog Sequence Rule (International Union of Pure and Applied Chemistry, "Nomenclature of Organic Chemistry, Sections, A, B, C, D, E, F, and H", Pergamon Press, Oxford, 1979; Cahn, R.S., Ingold, C.K., Prelog, V., *Agnew. Chem., Int. Ed. Engl.* 1966, 5: 385; and Prelog, V., Helmchen, G., *Agnew. Chem., Int. Ed. Engl.* 1982, 21: 567).

BIOLOGICAL ASSAY METHODS

The compounds were assessed for alpha-adrenergic receptor subtype selectivity by use of radioligand binding tecniques as described previously (DeBernardis et al., *J. Med. Chem.*, 1985, 28: 1398). Affinity for the alpha-1 receptor was assessed using rat liver homogenates and the radioligand [$^3$H]-prazosin; whereas for the aslpha-2 receptor, rat cerebral cortices and the radioligand [$^3$H]-rauwolscine were utilized. Results obtained from the binding studies are shown in Table 1 for a representative sample of compounds disclosed herein, showing clearly the excellent affinity for the alpha-2 receptor, as well as the high degree of selectivity relative to the alpha-1 adrenorecptor.

The primary method of evaluation of biogenic amine uptake activity has been the in vitro determination of the inhibition of radioactive amine uptake by synaptosome preparations of brain tissue. Basic procedures used are those described by Snyder and Coyle (Snyder, S.H. and J.T. Coyle, Regional Differences in $^3$H-Norepinephrine and $^3$H-Dopamine Uptake into Rat Brain Homogenates, *Journal of Pharmacology and Experimental Therapeutics* 1969, 165: 78–86) and Wong et al. (Wong, D.T., J.S. Horng and R.W. Fuller, Kinetics of Serotonin Accumulation into Synaptosomes of Rate Brain—Effects of Amphetamine and Chloroamphetamines, *Biochemical Pharmacology* 1973, 22: 311–322).

Briefly, male Sprague-Dawley rats were decapitated and regions of their brains dissected according to the procedures of Glowinski and Iversen (Glowinski, J. and L.L. Iversen, Regional Studies of Catecholamines in the Rat Brain—I: The Disposition of [$^3$H]-Norepinephrine, [$^3$H]-Dopamine and [$^3$H]-DOPA in Various Regions of the Brain, *Journal of Neurochemistry* 1966, 13: 655–669). Hypothalamus (norepinephrine-), cortex (serotonin-) and striatum (dopamine-uptake) were homogenized in 10, 5 and 20 volumes, respectively, of 0.32 M sucrose using a Teflon/glass Potter-Elvehjem tisse grinder. Samples were centrifuges at 1000×G for 10 minutes and the supernatants harvested and used in the assay. Aliquots of tissue (100 μL) were added to 750 μL of Kreb's solution (composition in mM; sodium chloride 118, potassium chloride 4.0, calcium chloride 1.13, potassium dihydrogen phosphate 1.12, magnesium sulfate 1.20, sodium bicarbonate 2.4, D-glucose 5.0, disodium ethylenediaminetetraacetic acid 1.5, ascorbic acid 1.0, and Pargyline, 12.5 μM, pH=7.4, areated with 95% oxygen, 5% carbon dioxide), 50 μL of test compound diluted in 0.3 mM ascorbic acid, and 100 μL [$^3$H]-amine, final concentration approximately 100 nM. Tissues were incubated for 4 minuts at 37° C., followed by rapid vacuum filtration over Whatman GF/B filters and washed with 50 mM Tris-HCl (pH=7.4). Nonspecific uptake was estimated in duplicate samples incubated at 0° C. Data were analyzed as described previously (J.F. DeBernardis, D.J. Kerkman, D.L. Arendsen, S.A. Buckner, J.J. Kyncl, and A.A. Hancock, Conformationally Defined Adrenergic Agents. 5. Resolution, Absolute Configuration, and Pharmacological Characterization of the Enantiomers of 2-[5,6-Dihyroxy-1,2,3,4-tetrahydro-1-1-naphthyl]imidazoline: A Potent Agonist at α-Adrenoceptors, *Journal of Medicinal Chemistry* 1987, 30: 1011–1017).

TABLE 1

| Example | α-1 (nM) | α-2 (nM) | NE (μM) | 5-HT (μM) | DA (μM) |
|---|---|---|---|---|---|
| 19 | 24 | 1.8 | 0.906 | 0.015 | 4.911 |
| 20 | 80 | 7.8 | 0.727 | 0.041 | 5.556 |
| 21 | 26 | 1.0 | 1.392 | 0.073 | 6.678 |
| 22 | 109 | 1.7 | 0.395 | 0.014 | 7.796 |
| 23 | 134 | 2.0 | 3.334 | 0.094 | 7.554 |
| 24 | 111 | 2.6 | 2.022 | 0.008 | 9.648 |
| 25 | 118 | 3.4 | 4.397 | 0.052 | 3.188 |
| 26 | 30 | 1.3 | 2.078 | 0.014 | 7.007 |
| 27 | 31 | 7.7 | 0.860 | 0.011 | 7.759 |
| 28 | 26 | 1.6 | 1.066 | 0.005 | 3.948 |
| 29 | 48 | 1.6 | 1.485 | 0.017 | 4.736 |
| 30 | 31 | 0.38 | 3.900 | 0.133 | 5.694 |
| 31 | 21 | 0.50 | 1.146 | 0.122 | 17.267 |
| 32 | 56 | 6.2 | 0.342 | 0.127 | 4.965 |
| 33 | 125 | 10 | 1.252 | 0.070 | 3.806 |
| 34 | 30 | 5 | 1.108 | 0.076 | 5.310 |
| 35 | 21 | 1.6 | 1.306 | 0.129 | 6.572 |
| 36 | 41 | 4 | 0.677 | 0.043 | 8.066 |
| 37 | 100 | 1.5 | 4.072 | 0.017 | 4.314 |
| 38 | 26 | 1.4 | 3.868 | 0.063 | 4.001 |
| 39 | 31 | 4 | 1.514 | 0.002 | 10.719 |
| 47 | 94 | 10 | 1.149 | 0.017 | 6.452 |
| 48 | 52 | 5 | 2.699 | 0.003 | 20.622 |
| 51 | 13 | 2.0 | 0.745 | 0.009 | 2.528 |
| 58 | 18 | 2 | 21.696 | 0.248 | 24.500 |
| 61 | 20 | 5 | 0.224 | 0.017 | 0.760 |
| 62 | 54 | 2 | 1.163 | 0.017 | 9.567 |
| 63 | 54 | 15 | 1.203 | 0.028 | 15.655 |
| 64 | 4.5 | 5 | 4.681 | 0.022 | 13.182 |
| Rauwolscine | 450 | 2.8 | >100 | >100 | >100 |
| Fluoxetine | >1000 | >1000 | 1.307 | 0.300 | 15.193 |

The compounds of the invention can be administered in any effective pharmaceutically acceptable form to warm blooded animals, e.g., in oral, parenteral or infusable dosage forms, or as a buccal or nasal spray. Suitable routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilzed, for example, by filtration through a bateria-retaining filter, or by incorporating sterilizing agents into the compositions. They can alsobe manufactured in the form of sterile solid compositions which can be dissolved in sterile water, or other sterile injectable medium, immediately before use.

Solid dosage forms for oral admistration include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular compound and method of administration. The selected dosage level therefore depends upon the activity of the particular compound, the desired therapeutic effect, the route of administration, the desired duration of treatment, the severity of the condition being treated, the condition and prior medical history of the patient being treated and other factors. however, it is within the skill of the art to start doeses of the compound at levels lower than reqiured to achieve the desired therapeutic effect and to gradually increase the dosage until the desired effect is achieved.

Generally, dosage levels of about 0.1 to 200 mg, more preferably about 0.5 to 150 mg and most preferably about 1 to 125 mg of active ingredient per kg of body weight per day are administered orally to a mammalian patient suffering from depression. If desired, the daily does may be divided into multiple doses for administration, e.g., two to four separate doses per day.

In general, the compounds of the present invention can be prepared as illustrated in Scheme 1. For illustration purposes a 5-membered ring heterocycle is used; the analogous reactions can be carried out on 6-membered ring heterocycles as well. Accoring to this reaction scheme, the appropriate heterocyclic acetic acid 1 is reacted with oxalyl chloride or other appropriate chlorinating agent in methylene chloride containing dimethylformamide to give acid chloride 2. The appropriately substituted aminomethyl tetrahydronaphthalene 3, prepared by the procedure described in U.S. Pat. No. 5,128,362 issued Jul. 7, 1992, is reacted withthe acid chloride using triethylamine in methylene chloride or other appropriate coupling conditions. The carboxamide 4 is reduced with diborane or other appropriate reducing agent and acidified to give the secondary amine salt 5. This salt can be reductively alkylated using formaldehyde and an appropriate reducing agent such as sodium borohydride or other alkylation procedures to give the tertiary amine 6.

Those heterocylcic acetic acids 1 which are not commercially available are obtained by synthesis. Some general methods for preparing these intermediates are shown in Scheme 2. One general method is described in Scheme 2A, where Z can be $>O$, $>S$, or $>NH$. Friedel Crafts acylation of 7 yields the acylated intermediate 8. Rearrangement of 8 to the phenylacetic acid side chain 1a can be effected by one of a variety of methods including Willgerodt-Kindler reaction or thallium-mediated oxidative rearrangement (Ref.: *J. Amer. Chem. Soc.* 1971, 93, 4919). The acid fragment 1a can be further elaborated by the procedures described in Scheme 1. Alternatively, the side chain acid portion may be dehydrogenated to hield yet another heterocyclic fragment 1b for coupling and reduction to yield another final product.

The corresponding 6-yl compounds can be prepared as described in Scheme 2B, where X can be $>O$ or $>S$. Alkylation of commercially available 9 with bromoacetaldehyde diethyl acetal affords 10. Dehydrative cyclization of 10 affords a heterocyclic intermediate 1c which can either be further elaborated by the procedures described in Scheme 1 or be hydrogenated or otherwise reduced to yield yet another heterocyclic fragment 1d for coupling and reduction.

Yet another heterocylcic substitution pattern is available by the method described in Scheme 2C. Allylic bis-halogenation of the commercially available 3,4-dimethyl intermediate 11, followed by displacement by an oxygen, sulfur, or nitrogen nucleophile yields either the cyclized intermediate 13 (when $X=RNH_2$ or $NH_3$), or a bis-substituted intermediate which can subsequently be cyclized (when $X=>O$, $>S$). The benzoic acid fragment 13 is readily elaborated via standard methods to the acetic acid side chain fragment 1e.

In cases where a methyl substituted heterocyclic fragment 14 is more readily accessible, elaboration is possible as shown in Scheme 2D. Allylic halogenation to give 15, followed by cyanide ion displacement to give 16 and then hydrolysis produces the desired heterocycle 1f.

Variously substituted quinoline containing side chains are prepared by standard literature methods; reaction of the appropriately substituted aniline derivative 17 with glycerol under acidic conditions gives 1g as shown in Scheme 2E. Catalytic hydrogenation of 1g affords the tetrahydroquinoline.

Approaches to the preparation of other six-membered nitrogen containing heterocycles are shown in Scheme 2F. Condensation of the appropriately substituted 1,2-dianiline 18 with 2,3-dihydroxy-1,4-dioxane yields the desired heterocycle 1h.

Appropriately substituted anilines 19 can serve as starting materials for the preparation of variously substituted benzothiazole derivatives as shown in Scheme 2G. Reaction of the aniline 19 with ammonium thiocyanate and bromine yields the 2-amino-benzothiazole 20, which can then be converted into a variety of 2-substituted benzothiazoles 1i (X=Cl, Br, CN, I, H, etc.).

In certain cases functional groups present on the heterocyclic portion of the molecule are incompatible with amine to acid coupling and/or amide reduction reaction conditions. An alternative approach for certain of these cases is shown in Scheme 2H. The requisite alkyl halides 23 (X= >O or >NH) are prepared via Friedel-Crafts acylation of 21 with chloroacetyl chloride to give chloroketone 22, followed by triethyl silane reduction. The further elaboration of compound 23 is shown in Scheme 3.

Appropriately substituted hydroxy phenylacetic acid esters 24 can serve as starting materials for the preparation of variously substituted isoxazoles, coumarins, dihydrocoumarins, and chromanones, as outlined in Scheme 2I. Formylation of the phenol by any of a variety of reagents (for example, hexamethylenetetramine and TFA, POCl$_3$ and DMF, Zn(CN)$_2$, etc.) provides a useful intermediate 25 for conversion into isoxazoles 26 using hydroxylamine-O-sulfonic acid and coumarins 27 using malonic acid condensation. The coumarin may be reduced using catalytic hydrogenation with a palladium catalyst to give the dihydro coumarin 28. Alternatively, the phenol 24 can be reacted with 3-bromopropanoic acid to give 29 and subsequently cyclized under acid catalysis to yield various 4-chromanones 30. The esters 26, 27, 28 and 30 can be hydrolyzed to give the carboxylic acids 1.

In yet another modification, appropriately substituted hydroxy phenylacetic acid esters 24 can serve as starting materials for the preparation of addition oxygen containing five membered ring heterocycles. Scheme 2J outlines the preparation of various benzofuranaones. The appropriate phenol 24 can be treated with chloroacetyl chloride in the presence of a Lewis acid to give the chloroacetyl derivative 31 followed by intramolecular cyclization in the presence of base to yield various benzofuran-3-ones 32. Alternatively, the phenol can be esterified with chloroacetic anhydride to give the chloroacetyoxy derivative 33 followed by intramolecular Friedel Crafts alkylation to yield variously substituted benzofuran-2-ones 34. Esters 32 and 34 can be hydrolyzed to give the carboxylic acids 1.

Alternatively, appropriately substituted hydroxy phenylacetic acid esters 24 can serve as starting materials for the preparation of substituted oxathioles, as outlined in Scheme 2K. Reaction of 24 with thiocyanogen choride followed by base promoted cyclization yields the oxathiolone 35, which can also be converted to the oxathiole 36 via aqueous hydrochloric acid hydrolysis followed by treatment with dibromomethane in the presence of base. Esters 35 and 36 can be hydrolyzed to give the carboxylic acids 1.

Scheme 2L illustrates the preparation of variously substituted isoquinolines and tetrahydroisoquinolines. Isoquinolines 38 can be prepared by a variety of standard methods (such as Pomeranz-Fritsch reaction or various newer modifications, i.e. Hendrickson and Rodriqwuez, *J. Org. Chem.*, 48, 3344 (1983)) from the methyl benzaldehyde 37. The methyl substituted isoquinoline 38 can be oxidized to the carboxylic acid 39, and then homologated via Arndt-Eistert synthesis to the desired isoquinoline-acetic acid 1j. These isoquinolines can be further elaborated to give tetahydroisoquinolines 1k by catalytic hydrogenation.

Scheme 2M illustrates the preparation of variously substituted quinazolines 11. These compounds can be prepared from appropriately substituted anthranilic acids 40. Condensation with formamide yields the hydroxyquinazoline 41, which can then converted to the chloroquinazoline 42 using phosphorous oxychloride, which then is dechlorinated under a variety of conditions, including hydrogenolysis, to give 43. Further elaboration under standard conditions, for example, Arndt-Eistert reaction, yields the acetic acid side chain derivative 11.

The known 5-nitro-isoindol-1,3-dione 44a (X=CO) and 5-nitrosaccharin 44b (X=SO$_2$) serve as starting materials for the preparation of various substituted phthalimide and saccharin side chains (Scheme 2N). Hydrogenation to give the amine, followed by diazotization and treatment with CuCN yields the desired cyano derivative 45. Hydrolysis affords the carboxylic acid 46 and then Arndt-Eistert homologation yields the desired phthalimido- and saccharin-acetic acid derivates 1m. these derivatives can then be alkylated to yield various 2-alkyl phthalimide and saccharin derivates 1n.

The heterocylcic chloroethyl side chain 23, described in Scheme 2H, is attached to the amine portion of themolecule 3 via an alkylation reaction as shown in Scheme 3, as opposed to the acetylation reaction shown in Scheme 1. Alkylation of the secondary amine 5 affords the tertiary amine 6b.

When the desired heterocyclic ring is not stable to the conditions required for coupling to the amine portion of the final product and/or reduction of the resultant carboxamide, it is expedient to synthesize the appended heterocyclic ring as the last step in the preparation of said compounds. Scheme 4 illustratesa generalized method, where X can be >O or >NH. The appropriately substituted nitro phenyl acetic acid 47 is coupled the N-alkylated amine portion of the molecule to give amide 48. Reduction of the carbonyl and nitro groups using catalytic hydrogenation followed by diborane reduction affords compound 49. Reaction of the aminophenol (X= >O) or diamine (X= >NH) with various carboxylic acid ortho esters (such as triethyl orthoformate or triethyl orthoacetate) yields the desired benzoxazole (X= >O) or benzimidazole (X= >NH) final products 6c.

The preparation of the R-diastereomer of the 1,2,3,4-tetrahydronaphthalene is shown in Scheme 5. The commercially available 5-methoxy tetralone 50 is reacted with diethylcyanophosphonate (DECNP) in the presence of catalytic amounts of lithium cyanide. The intermediate addition product is treated with p-toluenesulfonic acid in toluene and then reduced with sodium borohydride in ethanol. Hydrolysis with potassium hydroxide in ethylene glycol gives the racemic carboxylic acid 51. Treatment of 51 with oxalyl chloride followed by dimethylethylamine affords the intermediate ketene 52 which when reacted with (R)-(−)-pantolactone in toluene at −70° C. affords the chiral ester 53. Reduction of 53 with lithium aluminum hydride in tetrahydrofuran affords the (R)-alcohol 54. Treatment of 54 with methanesulfonyl chloride affords the methanesulfonate 55. Treatment with sodium azide in dimethylformamide affords azide 56. Reduction of the axide with lithium aluminum hydride affords the (R)-primary amine 57. Reductive alkylation using ethyl formate followed by borane reduction affords the (R)-N-methyl compound 58.
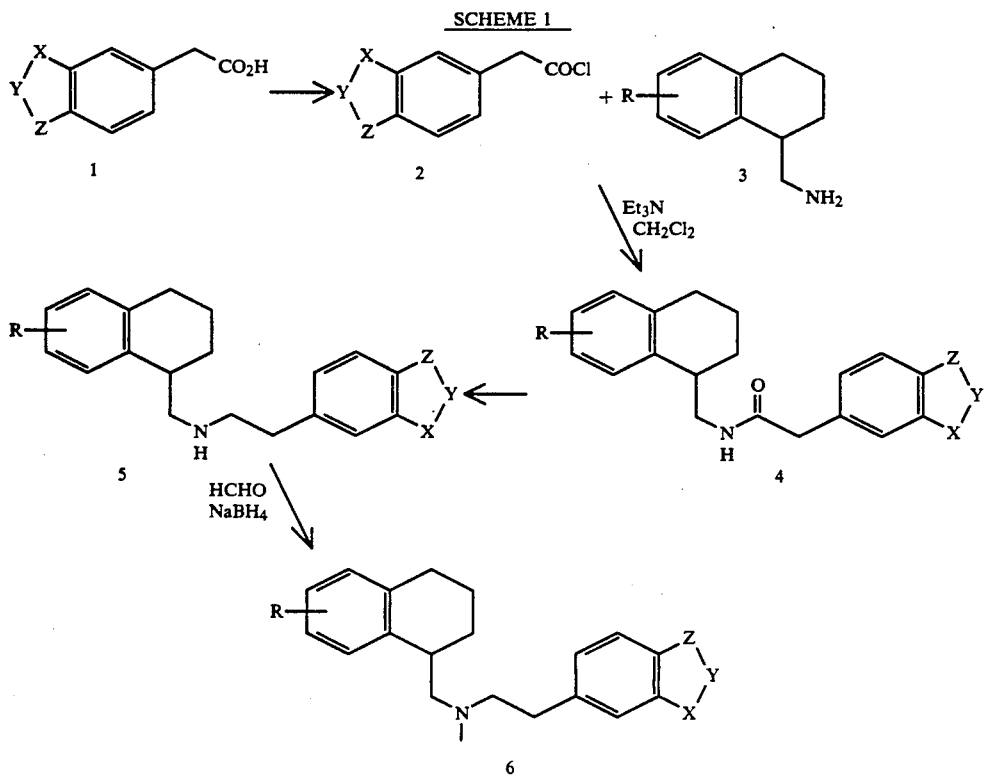
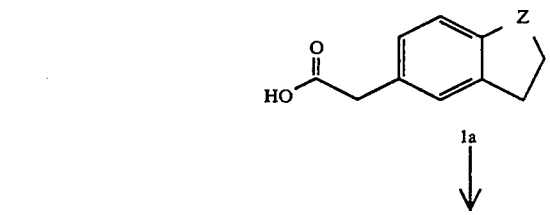

5,288,749
SCHEME 2C
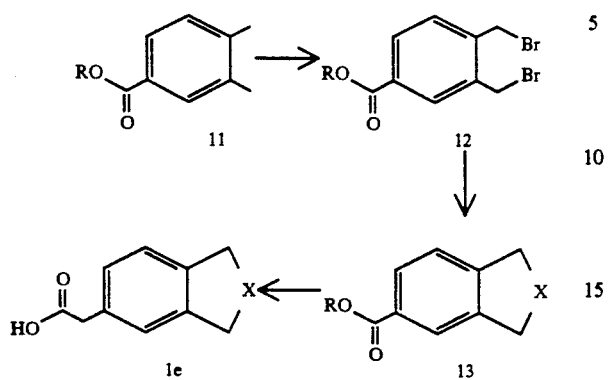
SCHEME 2D
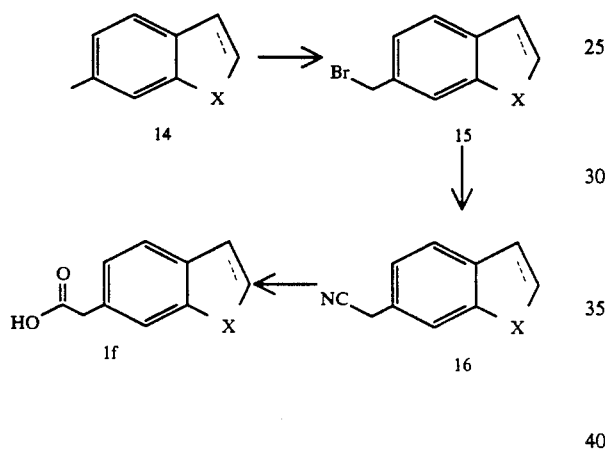
SCHEME 2E
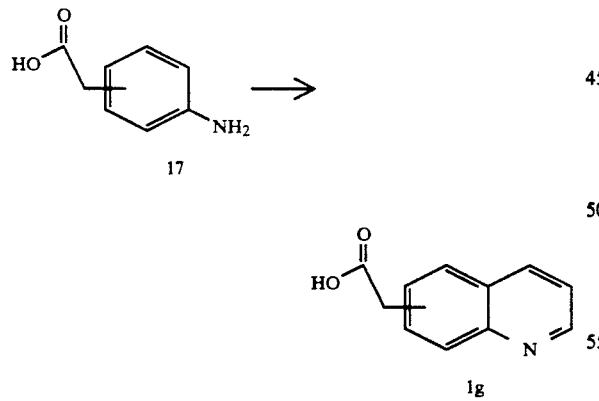
SCHEME 2F
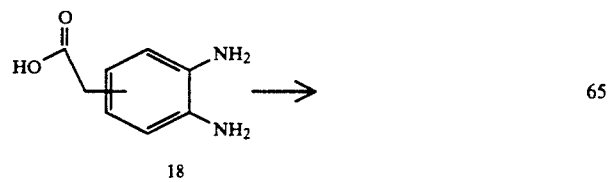
-continued
SCHEME 2F
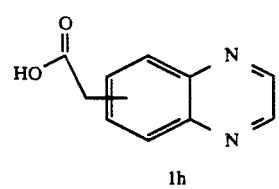
SCHEME 2G
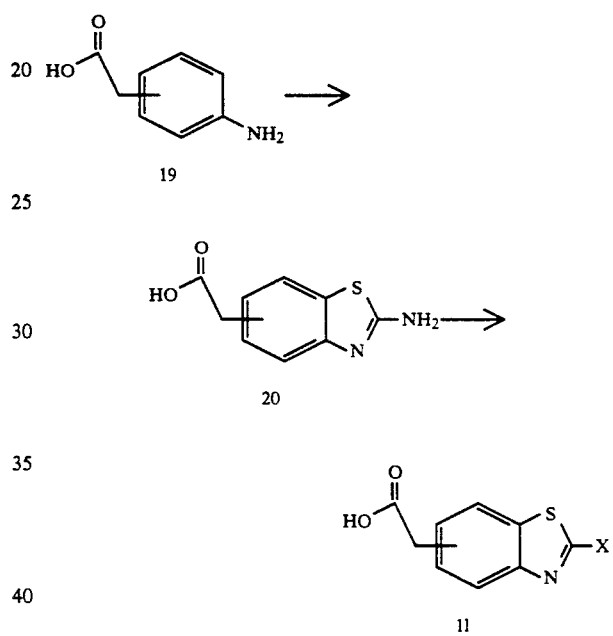
SCHEME 2H
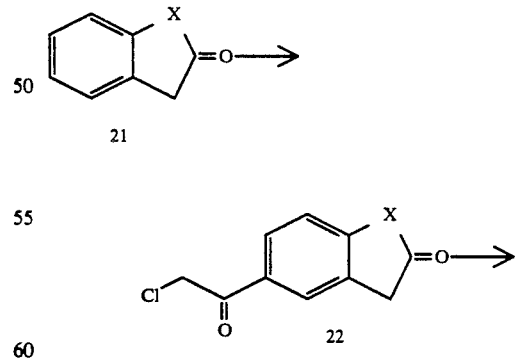

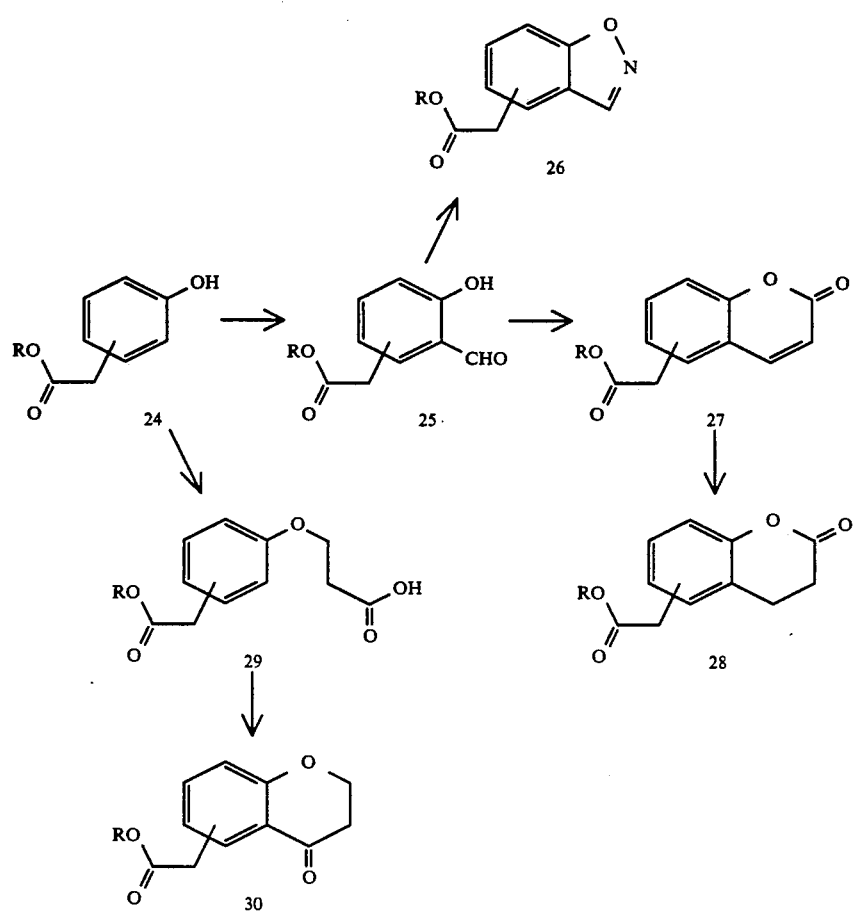
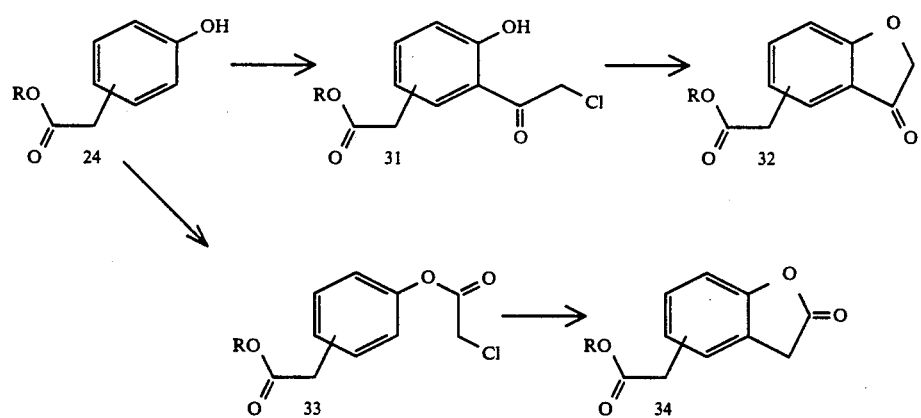
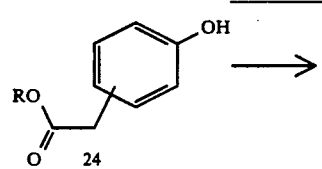
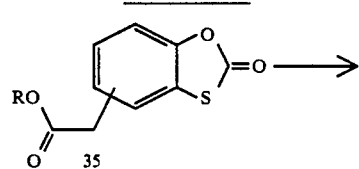

5,288,749
33
-continued
SCHEME 2K
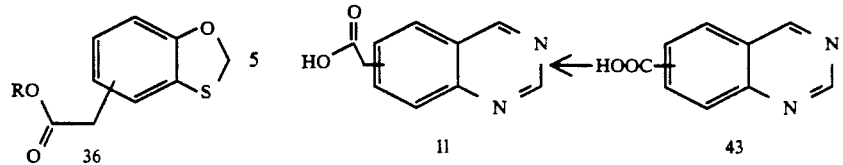
34
-continued
SCHEME 2M
SCHEME 2N
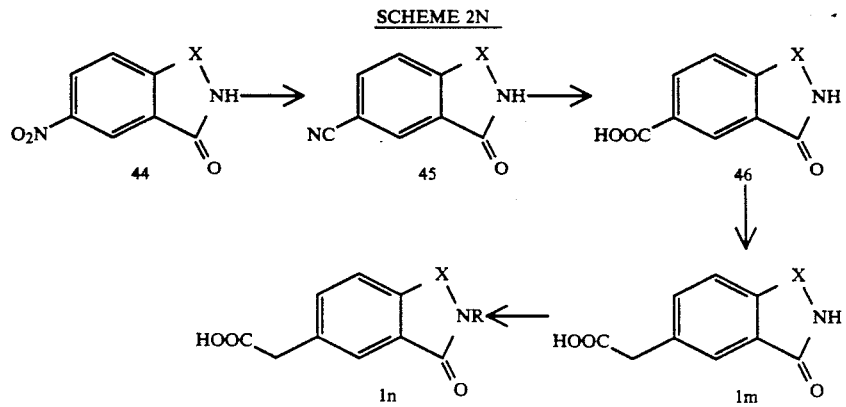
SCHEME 2L
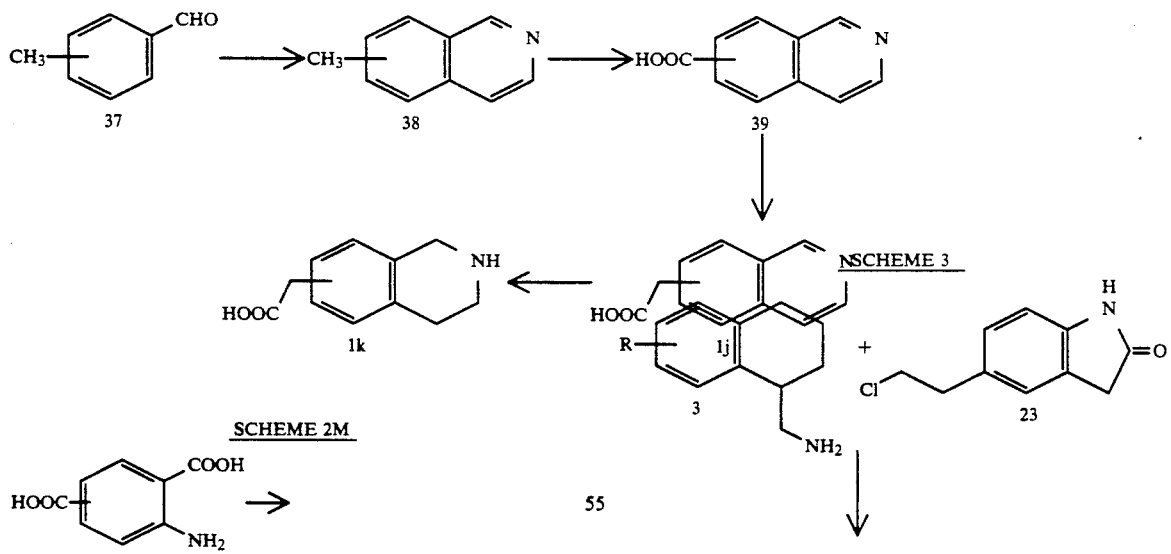
SCHEME 2M
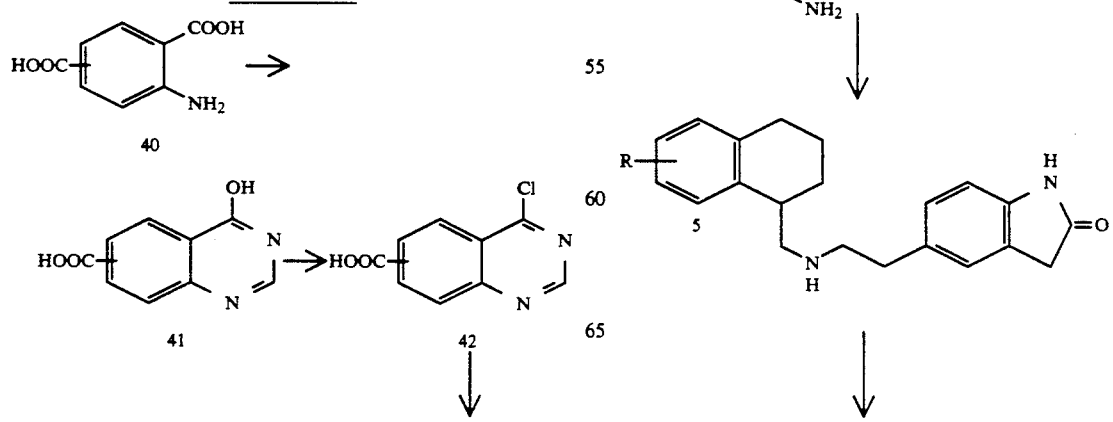

SCHEME 4
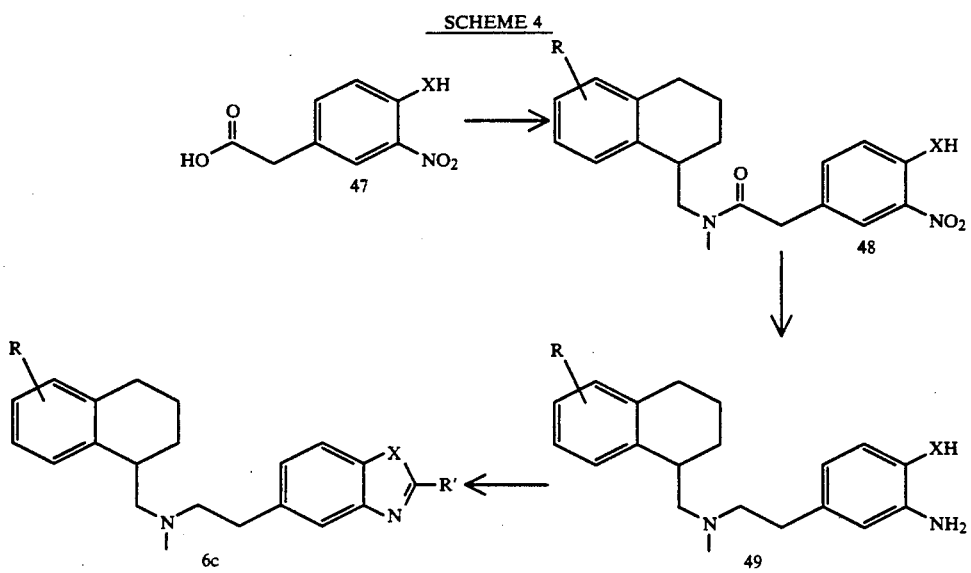
SCHEME 5
-continued
SCHEME 3
The following examples are provided for illustration and are not to be viewed as limiting the scope of the invention, and will serve to further illustrate preparation of the novel compounds of the invention. The following abbreviations are used: $CDCl_3$ for deuterochloroform, DMSO-d₆ for deuterodimethylsulfoxide, TMEDA for N,N,N',N'-tetramethylethylenediamine.

EXAMPLE 1

(1R) and (1S)-5-Methoxy-1,2,3,4-tetrahydronaphthalene-1-carboxylic-(R)-(−)-phenylglycinol amide To 5-methoxy-1,23,4-tetrahydronaphthalene-1-carboxylic acid, prepared by the procedure described in International Patent Application Number WO 89/06645, (1.03 g, 5.00 mmol) dissolved in methylene chloride (50 mL) was added oxalyl chloride (0.65 mL) and dimethylformamide (2 drops). After 1 hour at reflux, the solvent and excess reagent were evaporated. The resulting acid chloride was added to a solution of (R)-(−)-2-phenylglycinol (0.823 g, 6.00 mmol) and 1.4 mL triethylamine in methylene chloride (50 mL). After 1 hour, the reaction was quenched with dilute aqueous hydrochloric acid and extracted with methylene chloride. The combined organic extracts dried over magnesium sulfate and evaporated to dryness. The resulting solid was purified by chromatography on silica gel to yield 0.70 g of (1R)-5-methoxy-1,2,3,4-tetrahydronaphthalene-1-carboxylic-(R)-(−)-phenylglycinol amid. m.p. 179°–180° C. $^1$H NMR (CDCl$_3$, 300 MHz) δ1.75–2.0 (m, 3H), 2.3 (m, 1H), 2.39 (dd, 1H), 2.6 (m, 1H), 2.80 (dt, 1H), 3.70 (t, 1H), 3.79 (m, 2H), 3.4 (s, 3H), 5.1 (m, 1H), 6.05 (m, 1H), 6.75 (d, 1H), 6.77 (d, 1H), 7.13 (m, 3H), 7.3 (m, 3H). Further elution yielded 0.65 g of (1S)-5-methoxy-1,2,3,4-tetrahydronaphthalene-1-carboxylic-(R)-(−)-phenylglycinol amide. m.p. 181°–183° C.; $^1$H NMR (CDCl$_3$, 300 MHz) δ1.6–2.0 (m, 3H), 2.3 (m, 1H), 2.57 (t, 1H), 2.6 (m, 1H), 2.76 (dt, 1H), 3.73 (t, 1H), 3.7 (m, 2H), 3.83 (s, 3H), 5.07 (m, 1H), 6.08 (m, 1H), 6.76 (d, 1H), 6.81 (d, 1H), 7.13 (m, 3H), 7.3 (m, 3H).

EXAMPLE 2

(1R)-1-{N-[2-[(2R)-1-Hydroxy-2-phenyl]ethyl]aminomethyl}-5-methoxy-1,2,3,4-tetrahydronaphthalene hydrochloride The (R,R) product from Example 1 (7.18 g, 22 mmol) was dissolved in 100 mL etetrahydrofuran and 110 mL 1.0 M borane tetrahydrofurancomplex and refluxed for 3.5 hours. The reaction was quenched by the addition of ethanol (50 mL) and the solvent evaporated. The residue obtained was dissolved in methanol (50 mL), and hydrogen chloride saturated isopropanol (25 mL) and refluxed for 30 minutes. The solvent was evaporated to yield 5.96 g of the desired product as a white solid. m.p. 157°–158° C. $^1$H NMR (CDCl$_3$, 300 MHz) δ1.4 (m, 1H), 1.76 (m, 1H), 2.39 (dd, 1H), 2.6 (m, 1H), 2.25 (m, 1H), 2.4 (m, 1H), 2.62 (m, 1H), 2.97 (m, 1H), 3.1 (m, 1H), 3.52 (m, 1H), 3.75 (s, 3H), 4.08 (m, 1H), 4.5 (m, 2H), 5.62 (m, 1H), 6.62 (d, 1H), 6.73 (d, 1H), 7.03 (t, 1H), 7.43 (m, 3H), 7.7 (m, 2H), 9.5 (bs, 1H), 9.7 (bs, 1H). Anal calcd for C$_{20}$H$_{26}$ClNO$_2$: C, 69.05; H, 7.53; N, 4.03. Found: C, 68.66; H, 7.66; N, 4.02.

EXAMPLE 3

(1S)-1-{N-[2-[(2R)-1-Hydroxy-2-phenyl]ethyl]aminomethyl}-5-methoxy-1,2,3,4-tetrahydronaphthalene hydrochloride The (S,R) product from Example 1 (4.6 g, 14 mmol) was treated by the procedure described in Example 2 to yield 4.0 g of the desired product as a white solid. m.p. 190°–191° C. $^1$H NMR (CDCl$_3$, 300 MHz) δ1.6–2.0 (m, 3H), 2.25 (m, 1H), 2.43 (m, 1H), 2.7 (m, 1H), 3.07 (m, 1H), 3.5 (m, 1H), 3.77 (s, 3H), 4.02 (m, 1H), 4.4 (m, 2H), 5.5 (m, 1H), 6.62 (d, 1H), 6.63 (d, 1H), 7.03 (t, 1H), 7.43 (m, 3H), 7.68 (m, 2H), 9.1 (m, 1H), 10.1 (m, 1H). Anal calcd for C$_{20}$H$_{26}$ClNO$_2$: C, 69.05; H, 7.53; N, 4.03. Found: C, 69.16; H, 7.56; N, 3.95.

EXAMPLE 4

(R)-(+)-1-Aminomethyl-5-methoxy-1,2,3,4-tetrahydronaphthalene hydrochloride

The product from Example 2 (3.22 g, 9.3 mmol) was dissolved in methanol (100 mL) and treated with hyrogen in the presence of palladium on carbon at 25° C. for 24 hours to yield 1.65 g of the desired product as a white solid.

The (R,R) product from Example 1 (7.18 g, 22 mmol) was dissolved in 100 mL etetrahydrofuran and 110 mL 1.0 M borane tetrahydrofurancomplex and refluxed for 3.5 hours. The reaction was quenched by the addition of ethanol (50 mL) and the solvent evaporated. The residue obtained was dissolved in methanol (50 mL), and hydrogen chloride saturated isopropanol (25 mL) and refluxed for 30 minutes. The solvent was evaporated to yield 5.96 g of the desired product as a white solid. m.p. 266°–267° C. $^1$H NMR (DMSO-d$_6$, 300 MHz) δ1.6–1.9 (m, 4H), 2.45 (m, 1H), 2.62 (dt, 1H), 2.92 (dd, 1H), 3.04 (m, 2H), 3.77 (s, 3H), 6.80 (d, 1H), 6.86 (d, 1H), 7.13 (t, 1H), 8.07 (bs, 3H). Anal calcd for C$_{12}$H$_{18}$ClNO: C, 63.29; H, 7.97; N, 6.15. Found: C, 63.64; H, 8.09; N, 6.17.

EXAMPLE 5

(S)-(−)-1-Aminomethyl-5-methoxy-1,2,3,4-tetrahydronaphthalene hydrochloride

The product from Example 3 (3.89 g, 11.2 mmol) was dissolved in methanol (100 mL) and treated with hdyrogen in the presence of palladium on carbon at 25° C. for 24 hours to yield 2.39 g of the desired product as a white solid. m.p. 267°–269° C. $^1$H NMR (DMSO-d$_6$, 300 MHz) δ1.6–1.9 (m, 4H), 2.45 (m, 1H), 2.62 (dt, 1H), 2.92 (dd, 1H), 3.04 (m, 2H), 3.77 (s, 3H), 6.80 (d, 1H), 6.86 (d, 1H), 7.13 (t, 1H), 8.07 (bs, 3H). Anal calcd for C$_{12}$H$_{18}$ClNO: C, 63.29; H, 7.97; N, 6.15. Found: C, 63.56; H, 8.07; N, 6.16.

EXAMPLE 6

(1R) and (1S)-5-Methoxy-8-fluoro-1,2,3,4-tetrahydronaphthalene-1-carboxylic-(R)-(−)-phenylglycinol amide

EXAMPLE 6A

8-Fluoro-5-methoxy-3,4-dihydro-2H-1-naphthalenone

4-Fluoro-anisole (25 g, 198 mmol) and 48.8 g of ethyl succinyl chloride (298 mmol) were dissolved in 400 mL methylene chlorie and cooled to 0° C. to the reaction mixture was added 66 g of aluminum chloride over 15 minutes, and the reaction was then allowed to warn to 25° C. After 18 hours, the reaction was quenched by pouring onto ice and the product isolated by extraction. The intermediate keto-ester was hydrogenated over a palladium catalyst in ethanol (200 mL) containing concentrated hydrochloric acid (10 mL) until the theoretical amount of hydrogen was consumed. After the catalyst was removed by filtration and the filtrate concentrated under reduced pressure, the intermediate ester was treated with aqueous potassium hydroxide solution (200 mL). Upon acidification, the intermediate acid was obtained. The acid was converted to its acid chloride by treatment with oxalyl chloride (17 mL) in methylene chloride catalyzed by 5 drops of dimethylformamide. The solvent was removed under reduced pressure and the acid chloride was redissolved in methylene chloride. Aluminum chloride (90 g) was added, and the reaction was stirred at 25° C. for 18 hours. The reaction was quenched by pouring onto ice and the product extracted with ethyl acetate. The combined organic extracts were washed with water, dried over magnesium sulfate, and concentrated in vacuo. The residue obtained was recrystallized from hexane/ethyl acetate to yield 18.1 g of the title compound. m.p. $^1$H NMR (CDCl$_3$, 300 MHz) δ2.1 (m, 2H), 2.62 (t, 2H), 2.89 (t, 2H), 3.83 (s, 3H), 6.95 (m, 2H).

EXAMPLE 6B

8-Fluoro-5-methoxy-3,4-dihydro-naphthalenone-1-carbonitrile

The tetralone resulting from Example 6A (5.4 g, 28 mmol) and diethylcyanophosphonate (6.8 g, 42 mmol) were dissolved in 40 mL tetrahydrofuran. To the reaction was added 100 mg lithium cyanide. After 1 hour, the reaction was quenched by pouring into water and extracted with several portions of ethyl acetate. The combined organic extracts were dried and concentrated under reduced pressure. The crude product was dissolved in 100 mL of toluene and 2 g p-toluenesulfonic acid was added. The reaction was refluxed for 30 minutes and then quenched in 5% sodium bicarbonate solution. After extraction with ethyl acetate, the combined organic extracts were dried and concentrated under reduced pressure to yield 6.1 g. Recrystallization from hexane/ethyl acetate gave 5.65 g of the title compound. $^1$H NMR (CDCl$_3$, 300 MHz) δ2.43 (m,2H), 2.80 (t, 2H), 3.81 (s, 3H), 6.81 (dd, 1H), 6.93 (dd, 1H), 7.0 (t, 1H).

EXAMPLE 6C (1R) and
(1S)-5-Methoxy-8-fluoro-1,2,3,4-tetrahydronaphthalene-1-carboxylic-(R)-(−)-phenylglycinol amide The compound resulting from Example 6B (4.3 g) was treated with sodium borohydride in refluxing ethanol, followed by potassium hydroxide hydrolysis in refluxing ethylene glycol to yield the 1-carboxylic acid intermediate. This compound was then coupled with (R)-(−)-phenylglycinol according to the procedure outlined in Example 1 to yield 4.46 g of a mixture of diastereomeric amides.

EXAMPLE 7

(1R) and
(1S)-1-{N-[2-[(2R)-1-Hydroxy-2-phenyl]ethyl]aminomethyl}-5-methoxy-8-fluoro-1,2,3,4-tetrahydronaphthalene hydrochloride The diastereomeric mixture of amides from Example 6 (4.46 g) was treated by the procedure described in Example 2 to yield, after chromatographic separation, 1.4 g of the 1R isomer. m.p. 185°-186° C. $^1$H NMR (CDCl$_3$, 300 MHz) of the free base δ1.5–1.8 (m, 4H), 1.9 (bs, 1H), 2.12 (m, 1H), 2.43 (m, 1H), 2.2 (m, 3H), 3.2 (m, 1H), 3.54 (dd, 1H), 3.71 (dd, 1H), 3.74 (s, 3H), 3.85 (dd, 1H), 6.57 (dd, 1H), 6.76 (t, 1H), 7.3 (m, 5H). Also obtained was 1.3 g of the 1S isomer. m.p. 189°-190° C. $^1$H NMR (CDCl$_3$, 300 MHz) of the free base δ1.5–2.0 (m, 5H), 2.13 (m, 1H), 2.35–2.9 (m, 5H), 3.08 (m, 1H), 3.53 (dd, 1H), 3.7–3.8 (m, 2H), 3.76 (s, 3H), 6.56 (dd, 1H), 6.57 (t, 1H), 7.3 (m, 5H).

EXAMPLE 8

(R)-(+)-1-Aminomethyl-5-methoxy-8-fluoro-1,2,3,4-tetrahydronaphthalene hydrochloride The 1R isomer from Example 7 (1.3 g, 3.5 mmol) was treated by the procedure described in Example 4 to yield 0.76 g of the desired product as a white solid. m.p. 262°-264° C. $^1$H NMR (DMSO-d$_6$, 300 MHz) δ1.5–1.8 (m, 4H), 2.0 (d, 1H), 2.38 (m, 1H), 3.2 (m, 1H), 3.3 (m, 2H), 3.72 (s, 3H), 6.81 (dd, 1H), 6.96 (t, 1H), 8.0 (bs, 3H). $[\alpha]_D^{25°} = +50.0°$ (acetic acid).

EXAMPLE 9

(S)-(−)-1-Aminomethyl-5-methoxy-8-fluoro-1,2,3,4-tetrahydronaphthalene hydrochloride The 1S isomer from Example 7 (1.22 g, 3.3 mmol) was treated by the procedure described in Example 4 to yield 0.69 g of the desired product as a white solid. m.p. 262°-263° C. $^1$H NMR (DMSO-d$_6$, 300 MHz) δ1.5–1.8 (m, 4H), 2.0 (d, 1H), 2.38 (m, 1H), 3.2 (m, 1H), 3.3 (m, 2H), 3.72 (s, 3H), 6.81 (dd, 1H), 6.96 (t, 1H), 8.0 (bs, 3H). $[\alpha]_D^{25°} = -49.7°$ (acetic acid).

EXAMPLE 10

(R)-5-Methoxy-1,2,3,4-tetrahydronapthalene-1-carboxylic acid
(R)-dihydro-3-hydroxy-4,4-dimethyl-2(3H)-furanone ester Racemic 5-methoxy-1,2,3,4-tetrahydronaphthalene-1-carboxylic acid (46.31 g, 224.6 mmol) was dissolved in toluene 1 L). To the solution was added oxalyl chloride (21.6 mL, 247 mmol) and dimethylformamide (0.5 mL). After 1.5 hours at 50° C., the solution was cooled to 10° C. and dimethylethyl amine (73 mL, 674 mmol) was added. The reaction was stirred at ambient temperature for 3 hours, and then cooled to −70° C. (R)-Dihydro-3-hydroxy-4,4-dimethyl-2(3H)-furanone (35.1 g, 269.5 mmol) was added and the reaction was stirred for 2 hours, warming slowly to −30° C. The reaction was then poured into water and extracted with ether. The combined organic extracts were washed with 5% sodium bicarbonate and brine, dried over magnesium sulfate and evaporated to dryness under reduced pressure. Trituration with 1:1 ether/hexane yielded 61.68 g (86%) of the desired product as a white solid. m.p. 74°-77° C. $^1$H NMR (CDCl$_3$, 300 MHz) δ0.97 (s, 3H), 1.17 (s, 3H), 1.7–2.2 (m, 4H), 2.7 (m, 2H), 3.80 (s, 3H), 3.98 (t, 1H), 4.01 (s, 2H), 4.40 (s, 1H), 6.72 (d, 1H), 6.83 (d, 1H), 7.12 (t, 1H).

EXAMPLE 11

(R)-5-Methoxy-1,2,3,4-tetrahydronapthalene-1-methanol

To lithium aluminum hydride (14.7 g, 387.2 mmol) suspended in tetrahydrofuran (400 mL) was added 61.65 g (196.6 mmol) of the product from Example 10 dissolved in tetrahydrofuran (200 mL) over 30 minutes. After an additional 1 hour, the reaction was quenched using the Fieser workup conditions, filtered through Celite, and evaporated to dryness to yield 36.98 g, (98%) of the desired product as a colorless oil. $^1$H NMR (CDCl$_3$, 300 MHz) δ1.54 (bs, 1H), 1.7–2.0 (m, 4H), 2.5–2.7 (m, 2H), 2.97 (m, 1H), 3.80 (d, 2H), 3.81 (s, 3H), 6.70 (d, 1H), 6.86 (d, 1H), 7.12 (t, 1H).

EXAMPLE 12

(R)-5-Methoxy-1,2,3,4-tetrahydronapthalene-1-methanol-methanesulfonate ester The product from Example 11 (36.98 g, 192.3 mmol) was dissolved in methylene chloride (600 mL) and triethylamine (53.6 mL, 385 mmol). The solution was cooled to 0° C., and methanesulfonyl chloride (17.85 mL, 230.7 mmol) was added over 15 minutes. After 1 hour at 0° C., the reaction was poured into water and extracted with methylene chloride. The combined organic extracts were washed with 5% sodium bicarbonate and brine, dried over magnesium sulfate, and evaporated to dryness to yield 4.05 g (94%) of the desired product as a light yellow solid. m.p. 55°–56° C. $^1$H NMR (CDCl$_3$, 300 MHz) δ1.7–2.0 (m, 4H), 2.56 (m, 1H), 2.75 (dt, 1H), 2.98 (s, 3H), 3.22 (m, 1H), 3.81 (s, 3H), 4.28 (t, 1H), 4.40 (dd, 1H), 6.71 (d, 1H), 6.81 (d, 1H), 7.12 (t, 1H).

EXAMPLE 13

(R)-5-Methoxy-1-azidomethyl-1,2,3,4-tetrahydronapthalene

The product from Example 12 (49.05 g, 181.5 mmol) was dissolved in dimethylformamide (250 mL). To the solution was added sodium azide (27.4 g, 421.5 mmol) and the solution was stirred at 60° C. for 18 hours. The reaction compound was quenched with water and extracted with ether. The combined organic extracts were washed with water and brine, dried over magnesium sulfate and evaporated to dryness to yield 35.46 g (90%) of the desired product as a light yellow solid. m.p. 65°–66° C. $^1$H NMR (CDCl$_3$, 300 MHz) δ1.7–2.0 (m, 4H), 2.58 (m, 1H), 2.71 (dt, 1H), 3.03 (m, 1H), 3.41 (dd, 1H), 3.59 (dd, 1H), 3.80 (t, 3H), 6.70 (d, 1H), 6.80 (d, 1H), 7.12 (t, 1H).

EXAMPLE 14

(R)-(+)-1-Aminomethyl-5-methoxy-1,2,3,4-tetrahydronaphthalene hydrochloride

The product from Example 13 (35.46 g, 163.2 mmol) was dissolved in tetrahydrofuran (150 mL) and added to a suspension of lithium aluminum hydride (12.4 g, 326 mmol) in tetrahydrofuran (400 mL). After 1 hour, the reaction was quenched by the addition of water, filtered, and evaporated to dryness. Conversion to the hydrochloric acid salt and recrystallization from ethanol yielded 32.11 g (86%) of the desired product as a white solid. m.p. 266°–267° C. $^1$H NMR (DMSO-d$_6$, 300 MHz) δ1.6–1.9 (m, 4H), 2.45 (m, 1H), 2.62 (dt, 1H), 2.92 (dd, 1H), 3.04 (m, 2H), 3.77 (s, 3H), 6.80 (d, 1H), 6.86 (d, 1H), 7.13 (t, 1H), 8.07 (bs, 3H). [α]$_D^{25°}$ = +26.1° (acetic acid).

EXAMPLE 15

N-[(R)-(+)-5-Methoxy-1,2,3,4-tetraydronaphthalen-1-ylmethyl]-N-methylamine hydrochloride The product from Example 14 (32.1 g, 141 mmol) was converted to its free base and refluxed in toluene (250 mL) and ethyl formate (250 mL) for 18 hours. The solvent was evaporated under reduced pressure and the product dissolved in tetrahydrofuran (250 mL). Borane (1.0 M in tetrahydrofuran, 564 mL) was added and the reaction was refluxed for 5 hours. After cooling to ambient temperature, methanol (50 mL) was added and solvent was evaporated under reduced pressure. To the product was added methanol (200 mL) and isopropanol saturated with anhydrous hydrogen chloride (100 mL). After refluxing for 2 hours, the solvent was evaporated to yield 29.5 g of the desired product. m.p. 214°–215° C. $^1$H NMR (DMSO-d$_6$, 300 MHz) δ1.65–1.9 (m, 4H), 2.4–2.7 (m, 2H), 2.59 (s, 3H), 3.0–3.3 (m, 3H), 3.76 (s, 3H), 6.81 (d, 1H), 6.87 (d, 1H), 7.14 (t, 1H), 8.7 (bs, 2H).

EXAMPLE 16

N-[(R)-(+)-5-Methoxy-8-fluoro-1,2,3,4-tetraydronaphthalen-1-ylmethyl]-N-methylamine hydrochloride The title compound was prepared from 5-methoxy-8-flouro-1,2,3,4-tetrahydronaphthalene-1-carboxylic acid, the compound resulting from the first step in Example 6C, by the procedures described in Examples 10 through 15 to yield the product as a white solid. m.p. 248°–250° C. $^1$H NMR (DMSO-d$_6$, 300 MHz) δ1.5–1.8 (m, 4H), 2.1 (m, 1H), 2.4 (m, 1H), 2.6 (t, 3H), 2.7 (m, 1H), 2.93 (m, 1H), 3.12 (m, 1H), 3.76 (s, 3H), 6.84 (dd, 1H), 7.0 (t, 1H), 8.9 (bs, 2H).

EXAMPLE 17

N-[(R)-(+)-5-Methoxy-1,2,3,4-tetraydronaphthalen-1-ylmethyl]-N-methylamine hydrochloride 5-Ethoxy-1-tetralone was prepared from the commercially available 5-methoxy-1-tetralone by treatment with AlCl$_3$ in benzene followed by alkylation of the resulting phenol with ethyl iodide in acetone in the presence of potassium carbonate. The resulting tetralone was then treated by the procedures described in International Patent Application Number WO 89/06645 for the preparation of 5-methoxy 1,2,3,4-tetrahydronaphthalene-1-carboxylic acid to yield 5-ethoxy-1,2,3,4-tetrahydronaphthalene-1-carboxylic acid. The title compound was prepared from 5-ethoxy-1,2,3,4-tetrahydronaphthalene-1-carboxylic acid by the procedures described in Example 10 through 15 to yield the product as a white solid. m.p. 219°–221° C. $^1$H NMR (DMSO-b$_6$, 300 MHz) δ1.32 (t, 3H), 1.65–1.9 (m, 4H), 2.4–2.7 (m, 2H), 2.59 (s, 3H), 3.0–3.3 (m, 3H), 4.0 (m, 2H), 6.78 (d, 1H), 6.84 (d, 1H), 7.12 (t, 1H), 8.6 (bs, 2H).

EXAMPLE 18

N-[(R)-(+)-5,6-Methylenedioxy-1,2,3,4-tetraydronaphthalen-1-ylmethyl]-N-methylamine hydrochloride 5,6-Methylenedioxy-1,2,3,4-tetrahydronaphthalene-1-carboxylic acid was prepared by the procedure described in International Patent Application Number WO 89/06645, and treated as described in Examples 10 through 15 to yield the product as a white solid. m.p. 225°–257° C. $^1$H NMR (DMSO-b$_6$, 300 MHz) δ1.6–1.9 (m, 4H), 2.5–2.7 (m, 2H), 2.58 (s, 3H), 3.06 (m, 2H), 3.16 (m, 1H), 5.97 (d, 2H), 6.77 (d, 1H), 6.79 (D, 1H), 8.8 (bs, 2H).

EXAMPLE 19

N-[2-(2,3-Dihydrobenzofuran-5-yl)ethyl]-N-[(R)-(+)-5-methoxy-1,2,3,4-tetrahydronaphthalen-1-ylmethyl]-N-methylamine methanesulfonate 2,3-Dihydrobenzofuran-5-acetic acid (0.98 g, 5.5 mmol) and the product from Example 15 (1.21 g, 5.0 mmol) were combined with 1-(3-dmethylaminopropyl)-3-ethyl carbodiimide hydrochloride (1.15 g, 6.0 mmol), 1-hydroxybenzotriazole (1.01 g, 67.5 mmol) and triethylamine (5.5 mmol), 0.7 mL) in tetrahydrofuran (50 mL) and the reaction was stirred for 18 hours at 25° C. The product was isolated and treated with 1.0 M borane in tetrahydrofuran (20 mL) at reflux for 4 hours. After isolation of the desired product, treatment with 1.1 equivalents of methanesulfonic acid and recrystallization from ethyl acetate yielded 1.29 g of the desired product as a white solid. m.p. 161°–163° C. $^1$H NMR (CDCl$_3$, 300 MHz) δ1.7–2.2 (m, 4H), 2.5–3.7 (m, 9H), 2.86 (s, 3H), 3.00 (d, 3H), 3.18 (t, 2H), 3.81 (s, 3H), 4.55 (t, 2H), 6.71 (m, 3H), 6.94 (dd, 1H), 7.15 (m, 2H), 10.8 (bs, 1H). Anal calcd for C$_{24}$H$_{33}$NO$_5$S: C, 64.40; H, 7.43; N, 3.13. Found: C, 64.33; H, 7.36; N, 3.06.

EXAMPLE 20

N-[2-(Benzofuran-5-yl)ethyl]-N-[5-methoxy-1,2,3,4-tetrahydronaphthalen-1-ylmethyl]-N-methylamine methanesulfonate Benzofuran-5-acetic acid (0.54 g) and the product from Example 15 (0.57 g) were treated as described in Example 19 to yield 0.52 g of the desired product as a white solid. m.p. 156°–157° C. $^1$H NMR (CDCl$_3$, 300 MHz) of the free base δ1.6–1.8 (m, 3H), 1.95 (m, 1H), 2.40 (s, 3H), 2.4–3.0 (m, 9H), 3.81 (s, 3H), 6.66 (d, 1H), 6.70 (d, 1H), 6.81 (d, 1H), 7.08 (t, 1H), 7.12 (dd, 1H), 7.4 (d, 1H), 7.41 (s, 1H), 7.59 (d, 1H). Anal calcd for C$_{24}$H$_{31}$NO$_6$S: C, 64.69; H, 7.01; N, 3.14. Found: C, 64.51; H, 6.88; N, 3.13.

EXAMPLE 21

N-[2-(2,3-Dihydrobenzofuran-5-yl)ethyl]-N-[(R)-(+)-5-methoxy-8-fluoro-1,2,3,4-tetrahydronaphthalen-1-ylmethyl]-N-methylamine methanesulfonate 2,3-Dihydrobenzofuran-5-acetic acid (0.62 g) and the product from Example 16 (0.75 g) were treated by the procedure described in Example 19 to yield 0.805 g of the desired product as a white solid. m.p. 130°–132° C. $^1$H NMR (CDCl$_3$, 300 MHz) of the free base δ1.7–2.1 (m, 4H), 2.4–2.5 (m, 2H), 2.8–3.6 (m, 7H), 2.85 (s, 3H), 3.02 (d, 3H), 3.18 (t, 2H), 3.80 (s, 3H), 4.56 (t, 2H), 6.6–7.0 (m, 4H), 7.13 (d, 1H), 10.9 (bs, 1H). Anal calcd for C$_{24}$H$_{32}$FNO$_5$S: C, 61.92; H, 6.93; N, 3.01. Found: C, 62.15; H, 6.95; N, 3.00.

EXAMPLE 22

N-[2-(Benzofuran-6-yl)ethyl]-N-[(R)-(+)-5-methoxy-1,2,3,4-tetrahydronaphthalen-1-ylmethyl]-N-methylamine methanesulfonate Benzofuran-6-acetic acid (0.63 g) and the product from Example 15 (0.61 g) were treated by the procedure described in Example 19 to yield 0.23 g of the desired product as a white solid. m.p. 191°–193° C. $^1$H NMR (CDCl$_3$, 300 MHz) of the free base δ1.6–2.0 (m, 4H), 2.4 (s, 3H), 2.3–3.0 (m, 9H), 3.81 (s, 3H), 6.67 (d, 1H), 6.72 (dd, 1H), 6.80 (d, 1H), 7.09 (m, 2H), 7.36 (s, 1H), 7.49 (d, 1H), 7.57 (d, 1H). Anal calcd for C$_{24}$H$_{31}$NO$_5$S: C, 64.69; H, 7.01; N, 3.14. Found: C, 65.32; H, 7.09; N, 3.12.

EXAMPLE 23

N-[2-(2,3-Dihydrobenzofuran-5-yl)ethyl]-N-[(R)-(+)-5-ethoxy-1,2,3,4-tetrahydronaphthalen-1-ylmethyl]-N-methylamine methanesulfonate 2,3-Dihydrobenzofuran-5-acetic acid (0.43 g) and the product from Example 17 (0.50 g) were treated by the procedure described in Example 19 to yield 0.49 g of the desired product as a white solid. m.p. 152°–153° C. $^1$H NMR (CDCl$_3$, 300 MHz) δ1.32 (t, 3H), 1.7–2.2 (m, 4H), 2.5–3.5 (m, 9H), 2.86 (s, 3H), 3.00 (d, 3H), 3.18 (t, 2H), 4.0 (m, 2H), 4.55 (t, 2H), 6.71 (m, 3H), 6.94 (dd, 1H), 7.15 (m, 2H), 10.8 (bs, 1H). Anal calcd for C$_{25}$H$_{35}$NO$_5$S: C, 65.05; H, 7.64; N, 3.03. Found: C, 65.04; H, 7.60; N, 3.01.

EXAMPLE 25

N-[2-(2,3-Dihydrobenzofuran-6-yl)ethyl]-N-[(R)-(+)-5-methoxy-1,2,3,4-tetrahydronaphthalen-1-ylmethyl]-N-methylamine hydrochloride 2,3-Dihydrobenzofuran-6-acetic acid (0.31 g) and the product from Example 15 (0.50 g) were treated by the procedure described in Example 19, converting instead to the hydrochloride salt, to yield 0.31 g of the desired product as a white solid. m.p. 227°–229° C. $^1$H NMR (CDCl$_3$, 300 MHz) of the free base δ1.6–2.0 (m, 4H), 2.38 (s, 3H), 2.4–3.0 (m, 9H), 3.17 (t, 2H), 3.81 (s, 3H), 4.54 (t, 2H), 6.68 (m, 3H), 6.80 (d, 1H), 7.10 (m, 2H). Anal calcd for C$_{23}$H$_{30}$NO$_2$Cl: C, 71.21; H, 7.79; N, 3.61. Found: C, 71.68; H, 7.87; N, 3.54.

EXAMPLE 25

N-[2-(2,3-Dihydrobenzofuran-5-yl)ethyl]-N-[(R)-(+)-5,6-methylethenedioxy-1,2,3,4-tetrahydronaphthalen-1-ylmethyl]-N-methylamine methanesulfonate 2,3-Dihydrobenzofuran-5-acetic acid (0.68 g) and the product from Example 18 (0.80 g) were treated by the procedure described in Example 19 to yield 1.08 g of the desired product as a white solid. m.p. 175°–176° C. $^1$H NMR (DMSO-d$_6$, 300 MHz) δ1.7–1.9 (m, 4H), 2.3 (s, 3H), 2.4–3.5 (m, 9H), 2.93 (d, 3H), 3.17 (t, 2H), 4.54 (t, 2H), 5.95 (s, 2H), 6.7–7.0 (m, 5H), 9.1 (bs, 1H). Anal calcd for C$_{24}$H$_{31}$NO$_6$S: C, 62.45; H, 6.77; N, 3.04. Found: C, 62.79; H, 6.81; N, 3.01.

EXAMPLE 26

N-[2-(2,3-Dihydrobenzo[b]thien-5-yl)ethyl]-N-[(R)-(+)-5-methoxy-1,2,3,4-tetrahydronaphthalen-1-ylmethyl]-N-methylamine methanesulfonate 2,3-Dihydrobenzothiophene-5-acetic acid (0.80 g) and the product from Example 15 (0.72 g) were treated by the procedure described in Example 19 to yield 0.33 g of the desired product as a white solid. m.p. 158°–159° C. $^1$H NMR (CDCl$_3$, 300 MHz) of the free base δ1.6–1.8 (m, 3H), 1.94 (m, 1H), 2.38 (s, 3H), 2.3–3.0 (m, 9H), 3.2–3.4 (m, 4H), 3.82 (s, 3H), 6.67 (d, 1H), 6.80 (d, 1H), 6.94 (dd, 1H), 7.1 (m, 3H). Anal calcd for C$_{24}$H$_{33}$NO$_5$S$_2$: C, 62.17; H, 7.17; N, 3.02. Found: C, 63.77; H, 7.62; N, 3.05.

EXAMPLE 27

N-[2-(Benzimidazol-5-yl)ethyl]-N-[(R)-(+)-5-methoxy-1,2,3,4-tetrahydronaphthalen-6-ylmethyl]-N-methylamine bis-methanesulfonate 4-Amino-3-nitrophenylacetic acid (0.97 g) and the product from Example 15 (1.0 g) were treated by the procedure described in Example 19. The intermediate product was hydrogenated using a palladium catalyst in ethanol to yield the intermediate dianiline. Refluxing of this intermediate with formic acid (1.2 equivalents) in 10% aqueous hydrochloric acid for 1 hour, followed by isolation and conversion to the bis-methanesulfonate salt yielded 0.61 g of the desired product as a white solid. m.p. 162°–164° C. $^1$H NMR (CDCl$_3$, 300 MHz) of the free base δ1.6–1.8 (m, 3H), 1.94 (m, 1H), 2.39 (s, 3H), 2.4–3.0 (m, 9H), 3.80 (s, 3H), 6.67 (d, 1H), 6.81 (d, 1H), 7.08 (t, 1H), 7.13 (dd, 1H), 7.47 (bs, 1H), 7.59 (bs, 1H), 8.01 (s, 1H), 9.5 (bs, 1H). Anal calcd for $C_{24}H_{35}N_3O_7S_2$: C, 53.30; H, 6.30; N, 7.80. Found: C, 52.93; H, 6.60; N, 7.62.

EXAMPLE 28

N-[2-(Benzoxazol-6-yl)ethyl]-N-[(R)-(+)-5-methoxy-1,2,3,4-tetrahydronaphthalen-1-ylmethyl]-N-methylamine methanesulfonate 4-Nitro-3-hydroxyphenylacetic acid (0.711 g) and the product from Example 15 (0.725 g) were treated by the procedure described in Example 19. The intermediate product was hydrogenated using a palladium catalyst in ethanol to yield the intermediate amino-phenol. Treatment of this intermediate with triethylorthoformate at reflux for 18 hours, followed by isolation and conversion to the methanesulfonate salt yielded 0.54 g of the desired product as a white solid. m.p. 139°–141° C. $^1$H NMR (CDCl$_3$, 300 MHz) δ1.7–2.3 (m, 5H), 2.5–3.6 (m, 8H), 2.89 (s, 3H), 3.06 (d, 3H), 3.82 (s, 3H), 6.7 (m, 2H), 7.13 (t, 1H), 7.27 (dd, 1H), 7.55 (bs, 1H), 7.72 (d, 1H), 8.09 (s, 1H), 11.0 (bs, 1H). Anal calcd for $C_{23}H_{30}N_2O_5S$: C, 61.86; H, 6.77; N, 6.27. Found: C, 61.60; H, 6.40; N, 6.19.

EXAMPLE 29

N-[2-(Benzoxazol5-yl)ethyl]-N-[(R)-(+)-5-methoxy-1,2,3,4-tetrahydronaphthalen-1-ylmethyl]-N-methylamine methanesulfonate 3-Nitro-4-hydroxyphenylacetic acid and the product from Example 15 were treated by the procedure described in Example 19. The intermediate product was hydrogenated using a palladium catalyst in ethanol to yield the intermediate amino-phenol. Treatment of this intermediate with triethyl orthoformate at reflux for 1 hour, followed by isolation and conversion to the methanesulfonate salt yielded the desired product as a white solid. m.p. 175°–177° C. $^1$H NMR (CDCl$_3$, 300 MHz) of the free base δ1.6–1.8 (m, 3H), 1.93 (m, 1H), 2.39 (s, 3H), 2.4–3.0 (m, 9H), 3.81 (s, 3H), 6.67 (d, 1H), 6.80 (d, 1H), 7.09 (t, 1H), 7.22 (dd, 1H), 7.47 (d, 1H), 7.62 (d, 1H), 8.08 (s, 1H). Anal calcd for $C_{23}H_{30}N_2O_5S$: C, 61.86; H, 6.77; N, 6.27. Found: C, 61.98; H, 6.82; N, 6.28.

EXAMPLE 30

N-[2-(Benzoxazol-6-yl)ethyl]-N-[(R)-(+)-8-fluoro-5-methoxy-1,2,3,4-tetrahydronaphthalen-1-ylmethyl]-N-methylamine methanesulfonate 4-Nitro-3-hydroxyphenylacetic acid (0.91 g) and the product from Example 16 (1.0 g) were treated by the procedure described in Example 19. The intermediate product was hydrogenated using a palladium catalyst in ethanol to yield the intermediate aminophenol. Treatment of this intermediate with triethylorthoformate at reflux for 18 hours, followed by isolation and conversion to the methanesulfonate salt yielded 0.84 g of the desired product as a white solid. m.p. 180°–181° C. $^1$H NMR (DMSO-d$_6$, 300 MHz) δ1.55–1.85 (m, 3H), 2.05 (m, 1H), 2.31 (s, 3H), 2.3–3.6 (m, 9H), 3.0 (d, 3H), 3.78 (s, 3H), 6.87 (dd, 1H), 7.02 (t, 1H), 7.38 (dd, 1H), 7.25 (dd, 1H), 7.32 (d, 1H), 8.75 (s, 1H), 9.3 (bs, 1H). Anal calcd for $C_{23}H_{29}FN_2O_5S$: C, 59.47; H, 6.29; N, 6.03. Found: C, 59.41; H, 6.40; N, 5.92.

EXAMPLE 31

N-[2-(Benzoxazol-5-yl)ethyl]-N-[(R)-(+)-8-fluoro-5-methoxy-1,2,3,4-tetrahydronaphthalen-1-ylmethyl]-N-methylamine methanesulfonate 3-Nitro-4-hydroxyphenylacetic acid (0.80 g) and the product from Example 16 (0.88 g) were treated by the procedure described in Example 19. The intermediate product was hydrogenated using a palladium catalyst in ethanol to yield the intermediate aminophenol. Treatment of this intermediate with triethylorthoformate at reflux for 18 hours, followed by isolation and conversion to the methanesulfonate salt yielded 0.29 g of the desired product as a white solid. m.p. 166°–167° C. $^1$H NMR (DMSO-d$_6$, 300 MHz) δ1.55–1.85 (m, 3H), 2.05 (m, 1H), 2.31 (s, 3H), 2.3–3.6 (m, 9H), 3.0 (d, 3H), 3.78 (s, 3H), 6.87 (dd, 1H), 7.03 (t, 1H), 7.4 (dd, 1H, 7.25 (dd, 1H), 7.30 (d, 1H), 8.75 (s, 1H), 9.3 (bs, 1H), Anal calcd for $C_{23}H_{29}FN_2O_5S$: C, 59.47; H, 6.29; H, 6.03. Found: C, 59.52; H, 6.31; N, 5.92.

EXAMPLE 32

N-[2-([4H]-2,3-Dihydrobenzopyran-6-yl)ethyl]-N-[(R)-(+)-5-methoxy-1,2,3,4-tetrahydronaphthalen-1-ylmethyl]-N-methylamine methanesulfonate

[4H]-2,3-Dihydrobenzopyran-6-acetic acid (0.50 g) and the product from Example 15 (0.48 g) were treated by the procedure described in Example 19 to yield 0.10 g of the desired product as a white solid. m.p. 171°–172° C. $^1$H NMR (DMSO-d$_6$, 300 MHz) δ1.7–2.0 (m, 6H), 2.3 (s, 3H), 2.4–3.5 (m, 11H), 2.95 (d, 3H), 3.77 (s, 3H), 6.6–7.2 (m, 6H), 9.1 (bs, 1H). anal calcd for $C_{25}H_{35}NO_5S$: C, 65.05; H, 7.64; N, 3.03. Found: C, 65.07; H, 7.66; N, 2.96.

EXAMPLE 33

N-[2-(Indan-5-yl)ethyl]-N-[(R)-(+)-5-methoxy-1,2,3,4-tetrahydronaphthalen-1-ylmethyl]-N-methylamine methanesulfonate Indan-5-acetic acid (1.0 g) and the product from Example 15 (0.96 g) were treated by the procedure described in Example 19 to yield 1.18 g of the desired product as a white solid. m.p. 170°–172° C. $^1$H NMR (DMSO-d$_6$, 300 MHz) δ1.7–2.1 (m, 6H), 2.31 (s, 3H), 2.4–3.5 (m, 13H), 2.96 (d, 3H), 3.77 (s, 3H), 6.82 (d, 1H), 6.87 (d, 1H), 7.0–7.3 (m, 4H), 9.1 (bs, 1H). Anal calcd for $C_{25}H_{35}NO_4S$: C, 67.38; H, 7.92; N, 3.14. Found: C, 67.87; H, 7.85; N, 3.14.

EXAMPLE 34

N-[2-(N-Methanesulfonamido-2,3-dihydroindol-5-yl)ethyl]-N-[(R)-(+)-5-methoxy-1,2,3,4-tetrahydronaphthalen-1-ylmethyl]-N-methylamine methanesulfonate M-Methanesulfonamide-2,3-dihydroindole-5-acetic acid (1.14 g) and the product from Example 15 (0.90 g) were treated by the procedure described in Example 19 to yield 0.98 g of the desired product as a white solid. m.p. 202°–203° C. $^1$H NMR (DMSO-d$_6$, 300 MHz) δ1.7–1.9 (m, 4H), 2.7 (s, 3H), 2.4–2.6 (m, 2H), 2.93 (d, 3H), 2.95 (s, 3H), 2.9–3.6 (m, 9H), 3.78 (s, 3H), 3.92 (m, 2H), 6.81 (d, 1H), 6.87 (d, 1H), 7.07–7.3 (m, 4H), 9.1 (bs, 1H). Anal calcd for $C_{25}H_{36}N_2O_6S_2$: C, 57.23; H, 6.92; N, 5.34. Found: C, 57.25; H, 6.88; N, 5.30.

EXAMPLE 35

N-[2-(Benzimidazol-5-yl)ethyl]-N-[(R)-(+)-8-fluoro-5-methoxy-1,2,3,4-tetrahydronaphthalen-1-ylmethyl]-N-methylamine bis methanesulfonate monohydrate 4-Amino-3-nitrophenylacetic acid (0.82 g) and the product from Example 16 (0.91 g) were treated by the procedure described in Example 19. The intermediate product was hydrogenated using a palladium catalyst in ethanol to yield the intermediate dianiline. Treatment of this intermediate with formic acid (1.2 equivalents) in 10% aqueous hydrochloric acid at reflux for 1 hour, followed by isolation and conversion to the bis-methanesulfonate salt yielded 0.63 g of the desired product as a white solid. m.p. 128°–130° C. $^1$H NMR (CDCl$_3$, 300 MHz) of the free base δ1.4–1.8 (m, 3H), 2.1 (m, 1H), 2.4 (s, 3H), 2.3–3.0 (m, 9H), 3.2 (m, 1H), 3.79 (s, 3H), 6.6 (dd, 1H), 6.8 (t, 1H), 7.16 (dd, 1H), 7.48 (bs, 1H), 7.59 (bs, 1H), 8.02 (s, 1H). Anal calcd for $C_{24}H_{34}FN_3O_7S_2 \cdot H_2O$: C, 49.90; H, 6.28; N, 7.27. Found: C, 49.68; H, 6.00; N, 7.10.

EXAMPLE 36

N-[2,3-Dihydroindol-5-yl)ethyl]-N-[(R)-(+)-5-methoxy-1,2,3,4-tetrahydronaphthalen-1-ylmethyl]-N-methylamine bis-methanesulfonate N-Benzoyl-2,3-dihydroindolyl-5-acetic acid (0.98 g) and the product from Example 15 (0.85 g) were treated by the procedure described in Example 19 to yield the intermediate N-benzyl analog of the title compound as its dihydrochloride salt. Hydrogenation of this intermediate using a palladium catalyst in methanol afforded, after conversion to its methanesulfonate salt, 0.60 g of the desired product as a white solid. m.p. 207°–208° C.. $^1$H NMR (DMSO-d$_6$, 300 MHz) δ1.7–2.0 (m, 4H), 2.3 (s, 6H), 2.4–2.7 (m, 2H), 2.96 (d, 3H), 3.0–3.7 (m, 12H), 3.77 (s, 3H), 6.82 (d, 1H), 6.88 (d, 1H), 7.1–7.4 (m, 4H), 9.2 (bs, 2H). Anal calcd for $C_{25}H_{38}N_2O_7S_2$: C, 55.33; H, 7.06; N, 5.16. Found: C, 55.20; H, 7.06; N, 5.05.

EXAMPLE 37

N-[3-(2-Chlorobenzothiazol-6-yl)ethyl]-N-[(R)-(+)-5-methoxy-1,2,3,4-tetrahydronaphthalen-1-ylmethyl]-N-methylamine methanesulfonate 2-Chlorobenzothiazole-6-acetic acid (0.33 g) and the product from Example 15 (0.31 g) were treated by the procedure described in Example 19. The intermediate borane reduction product, prior to treatment with hydrochloric acid, was evaporated, suspended in ether and treated with TMEDA (tetramethylethylenediamine) (1.2 equiv.) at reflux for 4 hours. After filtration and purification by column chromatography, the product was converted to its methanesulfonate salt to yield 0.23 g of the desired product as a white solid. m.p. 153°–154° C. $^1$H NMR (DMSO-d$_6$, 300 MHz) δ1.7–1.9 (m, 4H), 2.3 (s, 3H), 3.0 (d, 3H), 3.1–3.5 (m, 9H), 3.77 (s, 3H), 6.83 (d, 1H), 6.87 (d, 1H), 7.15 (t, 1H), 7.5 (dd, 1H), 7.97 (d, 1H), 8.04 (d, 1H), 9.3 (bs, 1H). Anal calcd for $C_{23}H_{29}ClN_2O_4S_2$: C, 55.38; H, 5.88; N, 5.63. Found: C, 55.03; H, 5.75; N, 5.49.

EXAMPLE 38

N-[2-(Quinolin-6-yl)ethyl]-N-[(R)-(+)-5-methoxy-1,2,3,4-tetrahydronaphthalen-1-ylmethyl]-N-methylamine methanesulfonate 4-Amino-3-nitrophenylacetic acid (0.97 g) and the product from Example 15 (1.0 g) were treated by the procedure described in Example 19. The intermediate product was hydrogenated over palladium in ethanol to yield the intermediate dianiline. Treatment of this intermediate with 2,3-dihydroxy-1,4-dioxane, followed by conversion to the methanesulfonate addition salt yielded 0.88 g. of the desired product. m.p. 192° C. $^1$H NMR (DMSO-d$_6$, 300 MHz) δ1.7–2.0 (m, 4H), 2.3 (s, 3H), 2.4–3.6 (m, 9H), 3.03 (d, 3H), 3.79 (s, 3H), 6.84 (d, 1H), 6.90 (d, 1H), 7.16 (t, 1H), 7.85 (dd, 1H), 8.1 (m, 2H), 8.96 (m, 2H), 9.1 (bs, 1H). Anal calcd for $C_{24}H_{31}N_3O_4S$: C, 62.99; H, 6.83; N, 9.18. Found: C, 62.79; H, 6.96; N, 9.00.

EXAMPLE 39

N-[2-(Quinolin-6-yl)ethyl]-N-[(R)-(+)-5-methoxy-1,2,3,4-tetrahydronaphthalen-1-ylmethyl]-N-methylamine dihydrochloride dihydrate Quinoline-6-acetic acid (1.0 g) and the product from Example 15 (0.95 g) were treated by the procedure described in Example 19 to yield 0.79 g of the desired product as a white solid. m.p. 137°–139° C. $^1$H NMR (DMSO-d$_6$, 300 MHz) δ1.6–2.7 (m, 7H), 2.95 (d, 3H), 3.2–3.7 (m, 6H), 3.79 (s, 3H), 6.80 (d, 1H), 6.92 (d, 1H), 7.15 (t, 1H), 7.85–8.3 (m, 4H), 8.82 (m, 1H), 9.14 (m, 1H). Anal calcd for $C_{24}H_{30}ClN_2O \cdot 2H_2O$: C, 6.40; H, 7.30; N, 5.96. Found: C, 61.13; H, 7.02; N, 5.89.

EXAMPLE 40

N-[2-(Quinolin-7-yl)ethyl]-N-[(R)-(+)-5-methoxy-1,2,3,4-tetrahydronaphthalen-1-ylmethyl]-N-methylamine methanesulfonate Quinoline-7-acetic acid and the product from Example 15 are treated by the procedure described in Example 19 to yield the title compound.

EXAMPLE 41

N-[2-(Isoquinolin-6-yl)ethyl]-N-[(R)-(+)-5-methoxy-1,2,3,4-tetrahydronaphthalen-1-ylmethyl]-N-methylamine methanesulfonate Isoquinoline-6-acetic acid and the product from Example 15 are treated by the procedure described in Example 19 to yield the title compound.

EXAMPLE 42

N-[2-(Isoquinolin-7-yl)ethyl]-N-[(R)-(+)-5-methoxy-1,2,3,4-tetrahydronaphthalen-1-ylmethyl]-N-methylamine methanesulfonate Isoqunioline-7-acetic acid and the product from Example 15 are treated by the procedure described in Example 19 to yield the title compound.

EXAMPLE 43

N-[(2-(N-Methanesulfonamido-2,3-dihydroindol-6-yl)ethyl]-N-[(R)-(+)-5-methoxy-1,2,3,4-tetrahydronaphthalen-1-ylmethyl]-N-methylamine methanesulfonate N-Methanesulfonamide-2,3-dihydroindole-6-acetic acid and the product from Example 15 are treated by the procedure described in Example 19 to yield the title compound.

EXAMPLE 44

N-[-2-(N-Methyl-2,3-dihydroindol-6-yl)ethyl]-N-[(R)-(+)-5-methoxy-1,2,3,4-tetrahydronaphthalen-1-ylmethyl]-N-methylamine methanesulfonate N-Methyl-2,3-dihydroindole-6-acetic acid and the product from Example 15 are treated by the procedure described in Example 19 to yield the title compound.

EXAMPLE 45

N-[2-(2,3-Dihydroindol-6-yl)ethyl]-N-[(R)-(+)-5-methoxy-1,2,3,4-tetrahydronaphthalen-1-ylmethyl]-N-methylamine methanesulfonate 2,3-Dihydroindole-6-acetic acid and the product from Example 15 are treated by the procedure described in Example 19 to yield the title compound.

EXAMPLE 46

N-[2-(2,3-Dihydroindol-5-yl)ethyl]-N-[(R)-(+)-5-methoxy-1,2,3,4-tetrahydronaphthalen-1-ylmethyl]-N-methylamine methanesulfonate 2,3-Dihydroindole-5-acetic acid and the product from Example 15 are treated by the procedure described in Example 19 to yield the title compound.

EXAMPLE 47

N-[2-(Indol-6-yl)ethyl]-N-[(R)-(+)-5-methoxy-1,2,3,4-tetrahydronaphthalen-1-ylmethyl]-N-methylamine fumarate 3/4 hydrate Indole-6-acetic acid (0.69 g) and the product from Example 15 (0.70 g) were treated by the procedure described in Example 19, substituting lithium aluminum hydride for borane, to yield 0.49 g of the desired product as a white powder. $^1$H NMR (DMSO-$d_6$, 300 MHz) $\delta$1.6–3.0 (m, 13H), 2.99 (d, 3H), 3.73 (s, 3H), 6.60 (s, 1H), 6.72 (d, 1H), 6.76 (d, 1H), 6.86 (d, 1H), 7.05 (t, 1H), 7.22 (m, 2H), 7.41 (d, 1H), 10.95 (bs, 1H). Anal calcd for $C_{27}H_{32}N_2O_5 \cdot 0.75H_2O$: C, 67.83; H, 7.06; N, 5.70. Found: C, 67.97; H, 6.97; N, 5.70.

EXAMPLE 48

N-[2-(N-Methanesulfondamido-1,3-dihydroisoindol-5-yl)ethyl]-N-[(R)-(+)-5-methoxy-1,2,3,4-tetrahydronaphthalen-1-ylmethyl]-N-methylamine methanesulfonate hemihydrate N-Methanesulfonamide-1,3-dihydroisoindole-5-acetic acid (1.0 g) and the product from Example 15 (1.05 g) were treated by the procedure described in Example 19 to yield 0.77 g of the desired product as a white solid. m.p. 209° C. $^1$H NMR (CDCl$_3$, 300 MHz) of the free base $\delta$1.5–2.0 (m, 6H), 2.38 (s, 3H), 2.4–3.0 (m, 7H), 2.88 (s, 3H), 3.81 (s, 3H), 4.68 (s, 4H), 6.67 (d, 1H), 6.80 (d, 1H), 7.1 (m, 4H). Anal calcd for $C_{25}H_{36}N_2O_6S_2 \cdot 0.5H_2O$: C, 56.26; H, 6.99; N, 5.25. Found: C, 55.85; H, 6.78; N, 5.24.

EXAMPLE 49

N-[2-(N-Methyl-1,3-dihydroisoindol-5-yl)ethyl]-N-[(R)-(+)-5-methoxy-1,2,3,4-tetrahydronaphthalen-1-ylmethyl]-N-methylamine methanesulfonate N-Methyl-1,3-dihydroisoindole-5-acetic acid and the product from Example 15 are treated by the procedure described in Example 19 to yield the title compound.

EXAMPLE 50

N-[2-(1,3-Dihydroisoindol-5-yl)ethyl]-N-[(R)-(+)-5-methoxy-1,2,3,4-tetrahydronaphthalen-1-ylmethyl]-N-methylamine methanesulfonate 1,3-Dihydroisoindole-5-acetic acid and the product from Example 15 are treated by the procedure described in Example 19 to yield the title compound.

EXAMPLE 51

N-[2-(Benzothiazol-6-yl)ethyl]-N-[(R)-(+)-5-methoxy-1,2,3,4-tetrahydronaphthalen-1-ylmethyl]-N-methylamine methanesulfonate Benzothiazole-6-acetic acid (0.95 g) and the product from Example 15 (0.90 g) were treated by the procedure described in Example 19, substituting 4 equivalents of TMEDA (N,N,N', N'-tetramethylethylenediamine) for the hydrochloric acid treatment to decompose the intermediate borane complex, to yield 0.67 g of the desired product as a white solid. m.p. 165°–167° C. $^1$H NMR (CDCl$_3$, 300 MHz) of the free base $\delta$1.4–2.0 (m, 6H), 2.47 (s, 3H), 2.4–3.1 (m, 7H), 3.80 (s, 3H), 6.67 (d, 1H), 6.80 (d, 1H), 7.09 (t, 1H), 7.35 (m, 2H), 7.80 (s, 1H), 8.04 (d, 1H), 8.91 (s, 1H). Anal calcd for $C_{23}H_{30}N_2O_4S_2$: C, 59.71; H, 6.54; N, 6.05. Found: C, 59.25; H, 6.48; N, 5.96.

EXAMPLE 52

N-[2-(2-Chlorobenzothiazol-5-yl)ethyl]-N-[(R)-(+)-5-methoxy-1,2,3,4-tetrahydronaphthalen-1-ylmethyl]-N-methylamine methanesulfonate 2-Chlorobenzothiazole-5-acetic acid and the product from Example 15 are treated by the procedure described in Example 37 to yield the title compound.

EXAMPLE 53

N-[2-(2-Benzothiazol-5-yl)ethyl]-N-[(R)-(+)-5-methoxy-1,2,3,4-tetrahydronaphthalen-1-ylmethyl]-N-methylamine methanesulfonate Benzothiazole-5-acetic acid and the product from Example 15 are treated by the procedure described in Example 51 to yield the title compound.

EXAMPLE 54

N-[2-(2,3-Dihydro-benzothiazol-6-yl)ethyl]-N-[(R)-(+)-5-methoxy-1,2,3,4-tetrahydronaphthalen-1-ylmethyl]-N-methylamine methanesulfonate The product from Example 51 is treated with H$_2$ in the presence of Rh/Alumina catalyst to yield the title compound.

EXAMPLE 55

N-[2-(1-Oxo-2,3-dihydrobenzothiphen-5-yl)ethyl]-N-[(R)-(+)-5-methoxy-1,2,3,4-tetrahydronaphthalen-1-ylmethyl]-N-methylamine methanesulfonate The product from Example 26 is treated with one equivalent of m-chloroperbenzoic acid to yield the title compound.

EXAMPLE 56

N-[2-(1,1-Dioxo-2,3-dihydrobenzothiophen-5-yl)ethyl]-N-[(R)-(+)-5-methoxy-1,2,3,4-tetrahydronaphthalen-1-ylmethyl]-N-methylamine methanesulfonate The product from Example 26 is treated with two equivalents of m-chloroperbenzoic acid to yield the title compound.

EXAMPLE 57

N-[2-(1-Oxo-2,3-dihydrobenzothiphen-6-yl)ethyl]-N-[(R)-(+)-5-methoxy-1,2,3,4-tetrahydronaphthalen-1-ylmethyl]-N-methylamine methanesulfonate The product from Example 54 is treated with one equivalent of m-chloroperbenzoic acid to yield the title compound.

EXAMPLE 58

N-[(2-(1,3-Dihydro-isobenzofuran-5-yl)-ethyl]-N-{(R)-(+)-5-methoxy-1,2,3,4-tetrahydronaphthalen-1-ylmethyl]-N-methylamine methanesulfonate 1,3-Dihydroisobenzofuran-5-acetic acid (1.00 g) and the product from Example 15 (0.95 g) were treated by the procedure described in Example 19, substituting lithium aluminum hydride for borane, to yield 0.77 g of the desired product as a white solid. m.p. 162°–164° C. $^1$H NMR (DMSO-d$_6$, 300 MHz) δ1.6–2.0 (m, 4H), 2.99 (d, 3H), 2.5–3.5 (m, 9H), 3.73 (s, 3H), 5.0 (m, 4H), 6.8–7.3 (m, 6H). Anal calcd for $C_{24}H_{33}NO_5S$: C, 64.40; H, 7.43; N, 3.13. Found: C, 64.35; H, 7.43; N, 3.13.

EXAMPLE 59

N-[2-(Benzo[1,3]oxathiol-5-yl)ethyl]-N-[(R)-(+)-5-methoxy-1,2,3,4-tetrahydronaphthalen-1-ylmethyl]-N-methylamine methanesulfonate Benzo[1,3]oxathiol-5-acetic acid and the product from Example 15 are treated by the procedure described in Example 19 to yield the title compound.

EXAMPLE 60

N-[2-(Benzo[1,3]oxathiol-6-yl)ethyl]-N-[(R)-(+)-5-methoxy-1,2,3,4-tetrahydronaphthalen-1-ylmethyl]-N-methylamine methanesulfonate Benzo[1,3]oxathiol-6-acetic acid and the product from Example 15 are treated by the procedure described in Example 19 to yield the title compound.

EXAMPLE 61

N-[2-(2-Amino-benzothiazol-5-yl)-ethyl]-N-{(R)-(+)-5methoxy-1,2,3,4-tetrahydronaphthalen-1-ylmethyl]-N-methylamine bis-methanesulfonate 2-Amino-benzothiazole-5-acetic acid (1.15 g) and the product from Example 15 (1.30 g) were treated by the procedure described in Example 19, substituting 4 equivalents of TMEDA (N,N,N', N'-tetramethylethylenediamine) for the hydrochloric acid treatment to decompose the intermediate borane complex, to yield 0.97 g of the desired product as a white solid. m.p. 200°–202° C. $^1$H NMR (DMSO-d$_6$, 300 MHz) δ1.4–2.0 (m, 6H), 2.47 (s, 3H), 2.4–3.0 (m, 7H), 3.81 (s, 3H), 5.1 (bs, 2H), 6.65 (d, 1H), 6.80 (d, 1H), 7.09 (t, 1H), 7.14 (dd, 1H), 7.44 (bs, 1H), 7.47 (d, 1H). Anal calcd for $C_{24}H_{35}N_3O_7S_3$: C, 50.24; H, 6.15; N, 7.32. Found: C, 50.62; H, 6.07; N, 7.31.

EXAMPLE 62

N-[(2-Benzofuran-5-yl)-ethyl]-N-{(R)-(+)-5-methoxy-1,2,3,4-tetrahydronaphthalen-1-ylmethyl]-N-methylamine methanesulfonate Benzofuran-5-acetic acid (0.53 g) and the product from Example 15 (0.85 g) were treated by the procedure described in Example 19, substituting lithium aluminum hydride for borane, to yield 0.85 g of the desired product as a white solid. m.p. 169°–171° C. $^1$H NMR (CDCl$_3$, 300 MHz) of the free base δ1.6–2.0 (m, 5H), 2.40 (s, 3H), 2.4–3.0 (m, 8H), 3.81 (s, 3H), 6.67 (d, 1H), 6.70 (dd, 1H), 6.80 (d, 1H), 7.09 (t, 1H), 7.12 (dd, 1H), 7.40 (d, 1H), 7.41 (s, 1H), 7.59 (d, 1H). Anal calcd for $C_{24}H_{31}NO_5S$: C, 64.70; H, 7.01; N, 3.14. Found: C, 65.01; H, 7.14; N, 3.19.

EXAMPLE 63

N-[2-(N-Methyl-2,3-dihydro-1H-indol-5-yl)-ethyl]-N-[(R)-(+)-5-methoxy-1,2,3,4-tetrahydronaphthalen-1-ylmethyl]-N-methylamine bis-methanesulfonate 1-Methyl-2,3-dihydroindole-5-acetic acid (0.70 g), and the product from Example 15 (0.95 g) were treated by the procedure described in Example 19 to yield 0.88 g of the desired product as a white solid. m.p. 189°–190° C. $^1$H NMR (DMSO-d$_6$, 300 MHz) δ1.6–1.9 (m, 5H), 2.4–3.7 (m, 12H), 2.75 (s, 3H), 2.95 (d, 3H), 3.77 (s, 3H), 6.6–7.2 (m, 6H), 9.0 (bs, 1H). Anal calcd for $C_{26}H_{40}N_2O_7S_2$: C, 56.09; H, 7.24; N, 5.03. Found: C, 56.22; H, 7.59; N, 4.95.

EXAMPLE 64

5-{2-[((R)-(+)-5-Methoxy-1,2,3,4-tetrahydro-naphthalen-1-ylmethyl)methyl-amino]-ethyl}-1,3-dihydro-indol-2-one methanesulfonate mono-hydrate 5-(2-Chloroethyl)-2,3-dihydroindol-2-one (1.4 g) and the product from Example 15 (1.2 g) were combined in dimethylformamide with sodium carbonate (1.10 g), ethyldiisopropyl amine (1.0 ml), and sodium iodide (5 mg) and heated at 100° C. for 18 hours. After chromatographic purification and conversion to its methanesulfonate salt, the desired product (0.44 g) was obtained as a white solid. m.p. 133°–134° C. $^1$H NMR (DMSO-d$_6$, 300 MHz) δ1.6–2.0 (m, 5H), 2.4–3.5 (m, 8H), 2.31 (s, 3H), 2.97 (d, 3H), 3.48 (s, 2H), 3.78 (s, 3H), 6.7–7.2 (m, 6H), 9.1 (bs, 1H), 9.87 (s, 1H). Anal calcd for $C_{24}H_{32}N_2O_5S \cdot H_2O$: C, 60.23; H, 7.16; N, 5.85. Found: C, 59.95; H, 6.81; N, 5.78.

EXAMPLE 65

6-{2-[((R)-(+)-5-Methoxy-1,2,3,4-tetrahydro-naphthalen-1-ylmethyl)methyl-amino]-ethyl}-3H-benzoxazol-2-one hydrochloride 4-Nitro-3-hydroxyphenylacetic acid (0.91 g) and the product from Example 15 (1.0 g) were treated by the procedure described in Example 19. The intermediate product was treated with H$_2$/Pd in EtOH to yield the intermediate amino-phenol. Treatment of this intermediate with 1,1'-carbonyldiimidazole in THF at reflux for 2 hours, followed by isolation and conversion to the hydrochloride salt yielded 0.49 g of the desired product as a white solid. m.p. 147°–149° C. $^1$H NMR (CDCl$_3$, 300 MHz) of the free base δ1.55–2.0 (m, 4H), 2.39 (s, 3H), 2.4–3.0 (m, 9H), 3.81 (s, 3H), 6.67 (d, 1H), 6.80 (d, 1H), 6.97 (m, 2H), 7.1 (m, 2H), 8.7 (bs, 1H). Anal calcd for $C_{22}H_{27}ClN_2O_3$: C, 65.58; H, 6.75; N, 6.95. Found: C, 65.18; H, 6.86; N, 6.97.

EXAMPLE 66

6-{2-[((R)-(+)-5-Methoxy-1,2,3,4-tetrahydro-naphthalen-1-ylmethyl)methyl-amino]-ethyl}-3H-benzoxazol-2-one hydrochloride hydrate 4-Amino-3-nitrophenylacetic acid (1.34 g) and the product from Example 15 (1.50 g) were treated by the procedure described in Example 19. The intermediate product was treated with H$_2$/Pd in EtOH to yield the intermediate di-aniline. Treatment of this intermediate with 1,1'-carbonyldiimidazole in THF at reflux for 2 hours, followed by isolation and conversion to the hydrochloride salt yielded 0.33 g of the desired product as a white solid. m.p. 192°–196° C. $^1$H NMR (DMSO-d$_6$, 300 MHz) δ1.6–1.9 (m, 4H), 2.4–3.5 (m, 9H), 2.9 (d, 3H), 3.77 (s, 3H), 6.85 (m, 5H), 7.12 (t, 1H), 9.8 (bs, 1H), 10.08 (s, 1H), 10.17 (s, 1H). Anal calcd for $C_{22}H_{28}ClN_3O_2\cdot0.75H_2O$: C, 63.60; H, 7.16; N, 10.11. Found: C, 63.70; H, 6.90; N, 9.94.

EXAMPLE 67

N-[2-(Benzo[b]thien-5-yl)ethyl]-N-[(R)-(+)-5-methoxy-1,2,3,4-tetrahydronaphthalen-1-ylmethyl]-N-methylamine methanesulfonate Benzothiophene-5-acetic acid (0.90 g) and the product from Example 15 (1.03 g) were treated by the procedure described in Example 19. The intermediate amide was treated with lithium aluminum hydride and following isolation and conversion to the methanesulfonate salt yielded 0.95 g of the desired product as a white solid. m.p. 181°–182° C. $^1$H NMR (CDCl$_3$, 300 MHz) δ1.75–2.25 (m, 5H), 2.55 (m, 1H), 2.78 (m, 1H), 2.88 (s, 3H), 3.04 (d, 3H), 3.20–3.65 (m, 6H), 3.81 (s, 3H), 6.70 (m, 2H), 7.13 (t, 1H), 7.30 (m, 2H), 7.47 (d, 1H), 7.73 (d, 1H), 7.82 (d, 1H), 11.0 (bs, 1H). Anal calcd for $C_{24}H_{31}NO_4S_2$: C, 62.44 ; H, 6.77; N, 3.03. Found: C, 62.32; H, 6.71; N, 3.01.

EXAMPLE 68

N-[2-(Benzo[b]thien-6-yl)ethyl]-N-[(R)-(+)-5-methoxy-1,2,3,4-tetrahydronaphthalen-1-ylmethyl]-N-methylamine methanesulfonate Benzothiophene-6-acetic acid (0.84 g) and the product from Example 15 (0.96 g) were treated by the procedure described in Example 19. The intermediate amide was treated with lithium aluminum hydride and following isolation and conversion to the methanesulfonate salt yielded 0.80 g of the desired product as a white solid. m.p. 198°–199° C. $^1$H NMR (CDCl$_3$, 300 MHz) δ1.75–2.25 (m, 5H), 2.55 (m, 1H), 2.78 (m, 1H), 2.88 (s, 3H), 3.04 (d, 3H), 3.20–3.65 (m, 6H), 3.81 (s, 3H), 6.72 (m, 2H), 7.15 (t, 1H), 7.30 (m, 2H), 7.47 (d, 1H), 7.80 (m, 2H), 11.0 (bs, 1H). Anal calcd for $C_{24}H_{31}NO_4S_2$: C, 62.44; H, 6.77; N, 3.03. Found: C, 62.24; H, 6.67; N, 3.09.

EXAMPLE 69

5-{2-[((R)-(+)-5-Methoxy-1,2,3,4-tetrahydro-naphthalen-1-ylmethyl)methyl-amino]-ethyl}-3H-benzoxazol-1-one hydrochloride 3-Nitro-4-hydroxyphenylacetic acid (1.47 g) and the product from Example 15 (1.50 g) were treated by the procedure described in Example 19. The intermediate product was treated with H$_2$/Pd in EtOH to yield the intermediate amino-phenol. Treatment of this intermediate with 1,1,'-carbonyldiimidazole in THF at reflux for 2 hours, followed by isolation and conversion to the hydrochloride salt yielded 0.80 g of the desired product as a white solid. m.p. 115°–119° C. $^1$H NMR (CDCl$_3$, 300 MHz) δ1.7–2.1 (m, 4H), 2.15–2.4 (m, 1H), 2.42–2.59 (m, 1H), 2.67–2.81 (m, 1H), 3.02 (d, 3H), 3.1–3.6 (m, 6H), 3.80 (s, 3H), 6.69 (d, 1H), 6.73–7.0 (m, 3H), 7.13 (t, 1H), 7.22 (d, 1H), 10.49 (s, 1H), 11.4 (bs, 1H). Anal calcd for $C_{22}H_{27}ClN_2O_3$: C, 65.58; H, 6.75; N, 6.95. Found: C, 65.16; H, 6.75; N, 6.77.

EXAMPLE 70

N-[2-(6-Methyl-2,3-dihydro-benzofuran-5-yl)ethyl]-N-[(R)-(+)-5-methoxy-1,2,3,4-tetrahydronaphthalen-1-ylmethyl]-N-methylamine methanesulfonate 6-Methyl-2,3-dihydrobenzofuran-5-acetic acid (0.63 g) and the product from Example 15 (0.72 g) were treated by the procedure described in Example 19 to yield 0.60 g of the desired product as a white solid. m.p. 199°–200° C. $^1$H NMR (CDCl$_3$ 300 MHz) of the free base δ1.6–2.0 (m, 4H), 2.26 (s, 3H), 2.40 (s, 3H), 2.4–3.0 (m, 9H), 3.14 (t, 2H), 3.81 (s, 3H), 4.51 (t, 2H), 6.59 (s, 1H), 6.67 (d, 1H), 6.81 (d, 1H), 6.97 (s, 1H), 7.09 (t, 1H). Anal calcd for $C_{25}H_{35}NO_5S$: C, 65.05; H, 7.64; N, 3.03. Found: C, 65.08; H, 7.62; N, 3.09.

EXAMPLE 71

N-[2-(2-Methyl-benzoxazol-6-yl)ethyl]-N-[(R)-(+)-5-methoxy-1,2,3,4-tetrahydronaphthalen-1-ylmethyl]-N-methylamine methanesulfonate 4-Nitro-3-hydroxyphenylacetic acid (1.70 g) and the product from Example 15 (2.00 g) were treated by the procedure described in Example 19. The intermediate product was treated with hydrogen over a palladium catalyst in EtOH to yield the intermediate aminophenol, which was dissolved in triethyl orthoacetate and heated at reflux for 1 hour. This intermediate was then treated with methanesulfonic acid to yield 1.15 g of the desired product as a white solid. m.p. 159°–161° C. $^1$H NMR (CDCl$_3$, 300 MHz) of the free base δ1.6–2.0 (m, 5H), 2.39 (s, 3H), 2.4–3.0 (m, 8H), 2.61 (s, 3H), 3.80 (s, 3H), 6.66 (d, 1H), 6.80 (d, 1H), 7.08 (d, 1H), 7.12 (dd, 1H), 7.31 (d, 1H), 7.52 (d, 1H). Anal calcd for $C_{24}H_{32}N_2O_5S$: C, 62.59; H, 7.00; N, 6.08. Found: C, 62.59; H, 6.96; N, 6.11.

EXAMPLE 72

N-[2-(2-Methyl-benzoxazol-5-yl)ethyl]-N-[(R)-(+)-5-methoxy-1,2,3,4-tetrahydronaphthalen-1-ylmethyl]-N-methylamine methanesulfonate 3-Nitro-4-hydroxyphenylacetic acid (1.70 g) and the product from Example 15 (2.00 g) were treated by the procedure described in Example 19. The intermediate product was treated with hydrogen over a palladium catalyst in EtOH to yield the intermediate aminophenol, which was dissolved in triethyl orthoacetate and heated at reflux for 1 hour. This intermediate was then treated with methanesulfonic acid to yield 1.36 g of the desired product as a white solid. m.p. 178°–179° C. $^1$H NMR (DMSO-d$_6$, 300 MHz) δ1.7–1.9 (m, 4H), 2.31 (s, 3H), 2.60 (s, 3H), 2.96 (d, 3H), 2.9–3.6 (m, 9H), 3.79 (s, 3H), 6.81 (d, 1H), 6.89 (d, 1H), 7.16 (t, 1H), 7.29 (dd, 1H), 7.65 (m, 2H), 9.2 (bs, 1H). Anal calcd for $C_{24}H_{32}N_2O_5S$: C, 62.59; H, 7.00; N, 6.08. Found: C, 62.64; H, 6.96; N, 6.10.

EXAMPLE 73

N-[2-(2-Propanesulfonyl-2,3-dihydro-1H-isoindol-5-yl)ethyl]-N-[9(R)-(+)-5-methoxy-1,2,3,4-tetrahydronaphthalen-1-ylmethyl]-N-methylamine hydrochloride 2-Propanesulfonyl-2,3-dihydro-1H-isoindole-5-acetic acid (0.75 g) and the product from Example 15 (0.57 g) were treated by the procedure described in Example 19 to yield 0.435 g of the desired product as a white solid. m.p. 197°–198° C. $^1$H NMR (CDCl$_3$, 300 MHz) of the free base δ1.05 (t, 3H), 1.6–2.0 (m, 6H), 2.47 (s, 3H), 2.4–3.0 (m, 9H), 3.00 (m, 2H), 3.80 (s, 3H), 4.69 (s, 4H), 6.66 (d, 1H), 6.80 (d, 1H), 7.1 (m, 4H). Anal calcd for C$_{26}$H$_{37}$ClN$_2$O$_3$S: C, 63.33; H, 7.56; N, 5.68. Found: C, 63.12; H, 7.54; N, 5.63.

EXAMPLE 74

N-[2-(1,1-Dioxo-2,3-dihydrobenzothiophen-6-yl)ethyl]-N-[(R)-(+)-5-methoxy-1,2,3,4-tetrahydronaphthalen-1-ylmethyl]-N-methylamine methanesulfonate The product from Example 54 is treated with two equivalents of m-chloroperbenzoic acid to yield the title compound.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound or pharmaceutically acceptable salt thereof having the structure

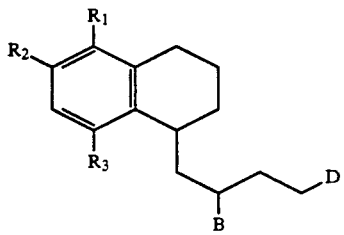

wherein

B is hydrogen or alkyl of from one to three carbon atoms;

R$_1$ is alkoxy of from one to four carbon atoms;

R$_2$ is hydrogen or, taken together with R$_1$ is methylenedioxy or ethylenedioxy;

R$_3$ is hydrogen, fluorine, or chlorine, and

D is selected from the group consisting of

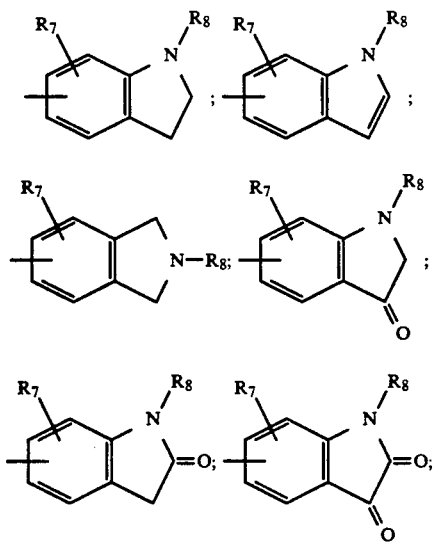

-continued

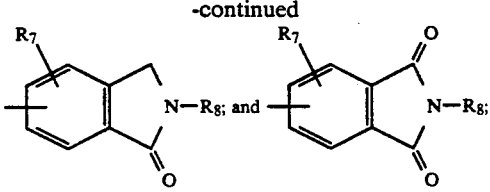

wherein

R$_7$ is one, two or three substituents independently selected from the group consisting of hydrogen, alkyl of from one to four carbon atoms, halogen, hydroxy, alkoxy of from one to four carbon atoms, amino, and thioalkoxy of from one to four carbon atoms; and R$_8$ is selected from hydrogen, lower alkyl and alkylsulfonyl.

2. A compound as defined by claim 1 in which the stereochemistry at the asymmetric center (*),

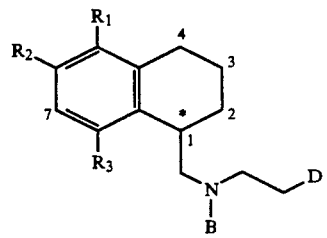

position-1 on the tetrahydronaphthalene, is of the R configuration.

3. A compound as defined by claim 1 wherein R$_1$ is methoxy or ethoxy.

4. A compound as defined by claim 1 wherein R$_1$ taken together with R$_2$ is methylenedioxy or ethylenedioxy.

5. A compound as defined by claim 1 wherein R$_3$ is hydrogen or fluorine.

6. A compound as defined by claim 1 wherein R$_1$ is methoxy, ethoxy, or taken taken with R$_2$ is methylenedioxy and R$_3$ is hydrogen or fluorine.

7. A compound as defined by claim 1 wherein B is hydrogen or methyl.

8. A compound as defined by claim 1 wherein B is methyl, R$_1$ is methoxy, ethoxy, or taken together with R$_2$ is methylenedioxy, R$_3$ is hydrogen or fluorine and the stereochemistry at the asymmetric center (*), position-1 on the tetrahydro-naphthalene, of is the R configuration.

9. A compound as defined by claim 7 selected from the group consisting of

N-(2-(N-Methanesulfonamido-2,3-dihydroindol-5-yl)ethyl)(-N-((R)-(+)-5-methoxy-1,2,3,4-tetrahydronaphthalen-1-ylmethyl)-N-methylamine;

N-(2,3-Dihydroindol-5-yl)ethyl(-N-((R)-(+)-5-methoxy-1,2,3,4-tetrahydronaphthalen-1-ylmethyl)-N-methylamine, N-(2-(N-Methanesulfonamido-2,3-dihydroindol-6-yl)ethyl(-N-((R)-(+)-5-methoxy-1,2,3,4-tetrahydronaphthalen-1-ylmethyl)-N-methylamine;

N-(2-(N-Propanesulfonamido-2,3-dihydroindol-6-yl)ethyl(-N-((R)-(+)-5-methoxy-1,2,3,4-tetrahydronaphthalen-1-ylmethyl)-N-methylamine;

N-(2-(N-Isobutanesulfonamido-2,3-dihydroindol-6-yl)e-
thyl(-N-((R)-(+)-5-methoxy-1,2,3,4-tetrahydronaph-
thalen-1-ylmethyl)-N-methylamine;

N-(2-(N-Methyl-2,3-dihydroindol-5-yl)ethyl(-N-
((R)-(+)-5-methoxy-1,2,3,4-tetrahydronaphthalen-1-
yl)-N-methylamine;

N-(2-(N-Methyl-2,3-dihydroindol-6-yl)ethyl(-N-
((R)-(+)-5-methoxy-1,2,3,4-tetrahydronaphthalen-1-
ylmethyl)-N-methylamine;

N-(2-(2,3-Dihydroindol-6-yl)ethyl-N-((R)-(+)-5-
methoxy-1,2,3,4-tetrahydronaphthalen-1-ylmethyl)-
N-methylamine;

N-(2-(2,3-Dihydroindol-5-yl)ethyl(-N-((R)-(+)-5-
methoxy-1,2,3,4-tetrahydronaphthalen-1-ylmethyl)-
N-methylamine;

N-(2-(Indol-6-yl)ethyl(-N-((R)-(+)-5-methoxy-1,2,3,4-
tetrahydronaphthalen-1-ylmethyl)-N-methylamine;

N-(2-(N-Methanesulfondamido-1,3-dihydroisoindol-5-
yl)ethyl(-N-((R)-(+)-5-methoxy-1,2,3,4-tetrahy-
dronaphthalen-1-ylmethyl)-N-methylamine;

N-(2-(N-Methyl-1,3-dihydroisoindol-5-yl)ethyl(-N-
((R)-(+)-5-methoxy-1,2,3,4-tetrahydronaphthalen-1-
ylmethyl)-N-methylamine;

N-(2-(1,3-Dihydroisoindol-5-yl)ethyl(-N-((R)-(+)-5-
methoxy-1,2,3,4 -tetrahydronaphthalen-1-ylmethyl)-
N-methylamine;

N-(2-(N-Methyl-2,3-dihydro-1H-indol-5-yl)-ethyl(-N-
((R)-(+)-5-methoxy-1,2,3,4-tetrahydronaphthalen-1-
ylmethyl)-N-methylamine; and 5-{2-(((R)-(+)-5-Methoxy-1,2,3,4-tetrahydro-naphthal-
en-1-ylmethyl)methylamino)-ethyl}-1,3-dihydro-
indol-2-one.

10. A compound as defined by claim 1 wherein D is selected from the group consisting of

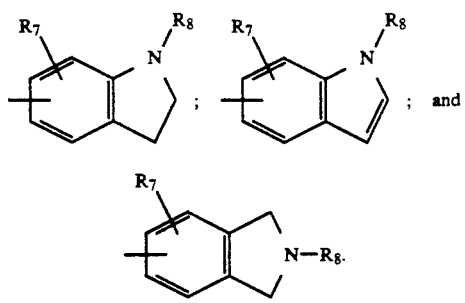

11. A compound as defined by claim 1 wherein D is selected from the group consisting of

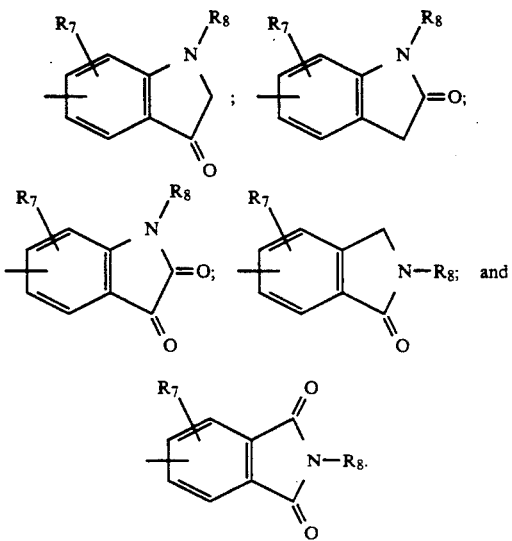

12. A compound having the name 5,6-methylene-dioxy-1-[(N-methyl-N-(2-(N-methylsulfonyl)dihy-droisoindol-4-yl)ethyl)methyl]-1,2,3,4-tetrahydronaph-thalene or a pharmaceutically acceptable salt thereof.

13. A composition for inhibiting serotonin uptake and antagonizing alpha-2 adrenoreceptors comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,288,749

DATED : February 22, 1994

INVENTOR(S) : M. D. Meyer; J. F. DeBernardis; R. Prasad; K. B. Sippy; K. R. Tietje Page 1 of 7

It is certified that error appears in the above-indentified patent and that said Letters Patent is hereby corrected as shown below:

COLUMN 33 & 34: REPLACE

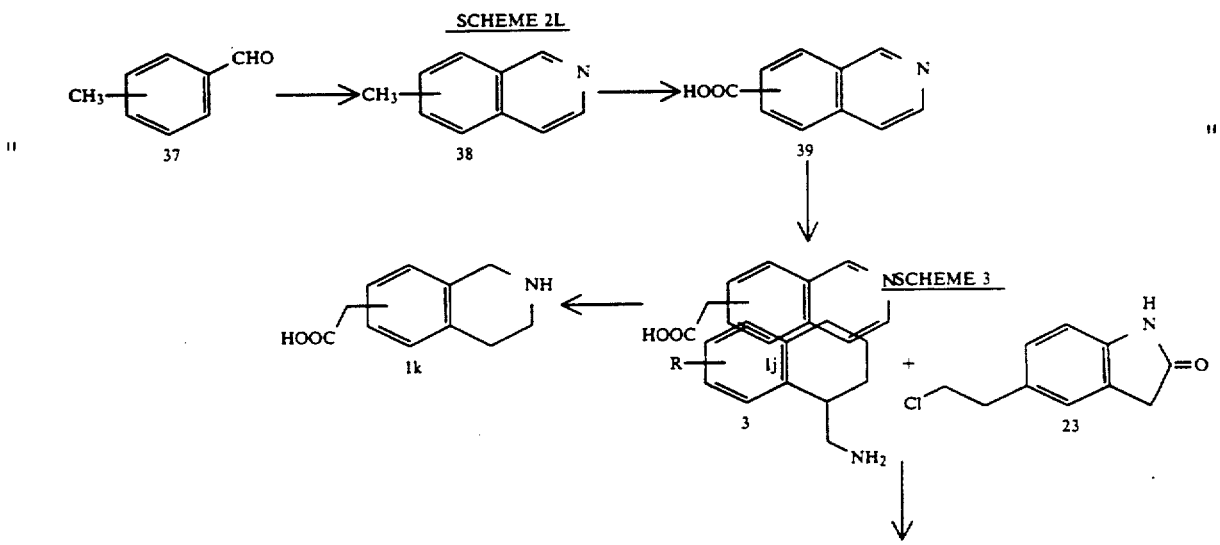

WITH

UNITED STATES PATENT AND TRADEMARK OFFICE
CERTIFICATE OF CORRECTION

PATENT NO. : 5,288,749
DATED : February 22, 1994
INVENTOR(S) : M. D. Meyer; J. F. DeBernardis; R. Prasad; K. B. Sippy; K. R. Tietje It is certified that error appears in the above-indentified patent and that said Letters Patent is hereby corrected as shown below:

SCHEME 2L

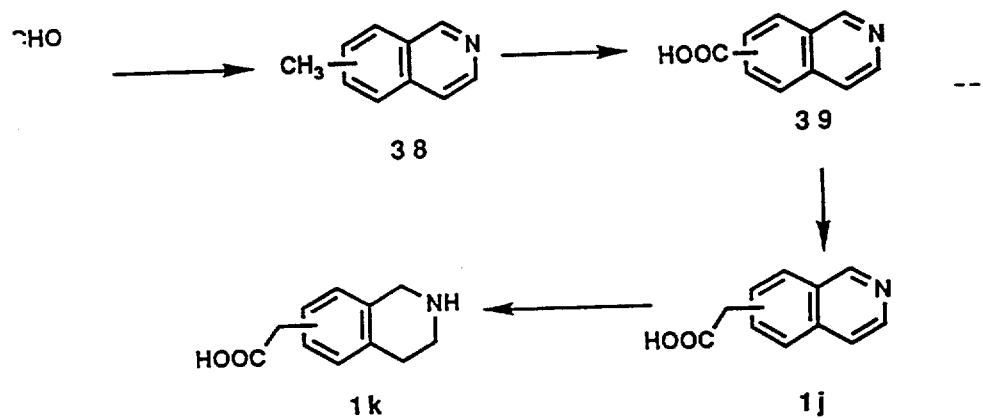

UNITED STATES PATENT AND TRADEMARK OFFICE
CERTIFICATE OF CORRECTION

PATENT NO. : 5,288,749

DATED : February 22, 1994

INVENTOR(S) : M. D. Meyer; J. F. DeBernardis; R. Prasad; K. B. Sippy; K. R. Tietje It is certified that error appears in the above-indentified patent and that said Letters Patent is hereby corrected as shown below:

COLUMN 33 & 34, REPLACE:

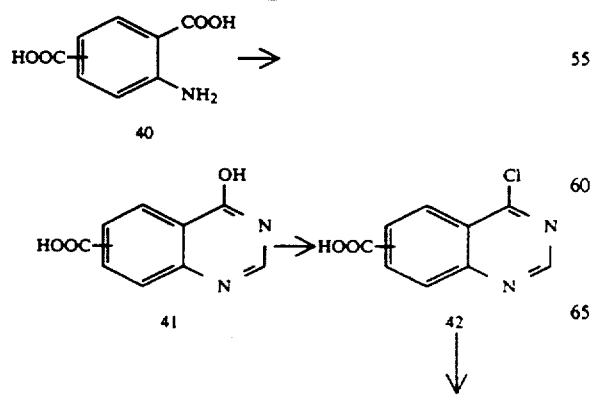

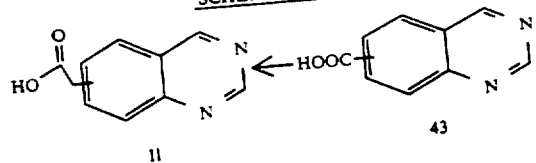

WITH

UNITED STATES PATENT AND TRADEMARK OFFICE
CERTIFICATE OF CORRECTION

PATENT NO. : 5,288,749
DATED : February 22, 1994
INVENTOR(S) : M. D. Meyer; J. F. DeBernardis; R. Prasad; K. B. Sippy; K. R. Tietje It is certified that error appears in the above-indentified patent and that said Letters Patent is hereby corrected as shown below:

SCHEME 2M

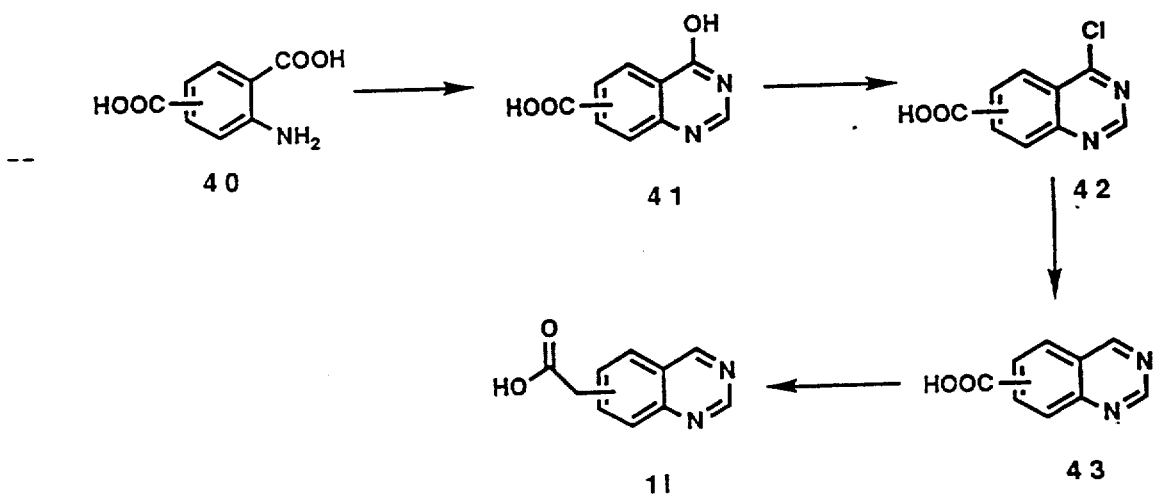

UNITED STATES PATENT AND TRADEMARK OFFICE
CERTIFICATE OF CORRECTION

PATENT NO. : 5,288,749                                Page 5 of 7
DATED      : February 22, 1994
INVENTOR(S): M. D. Meyer; J. F. DeBernardis; R. Prasad; K. B. Sippy;
             K. R. Tietje It is certified that error appears in the above-indentified patent and that said Letters Patent is hereby corrected as shown below:  COLUMN 34 & 35, REPLACE:

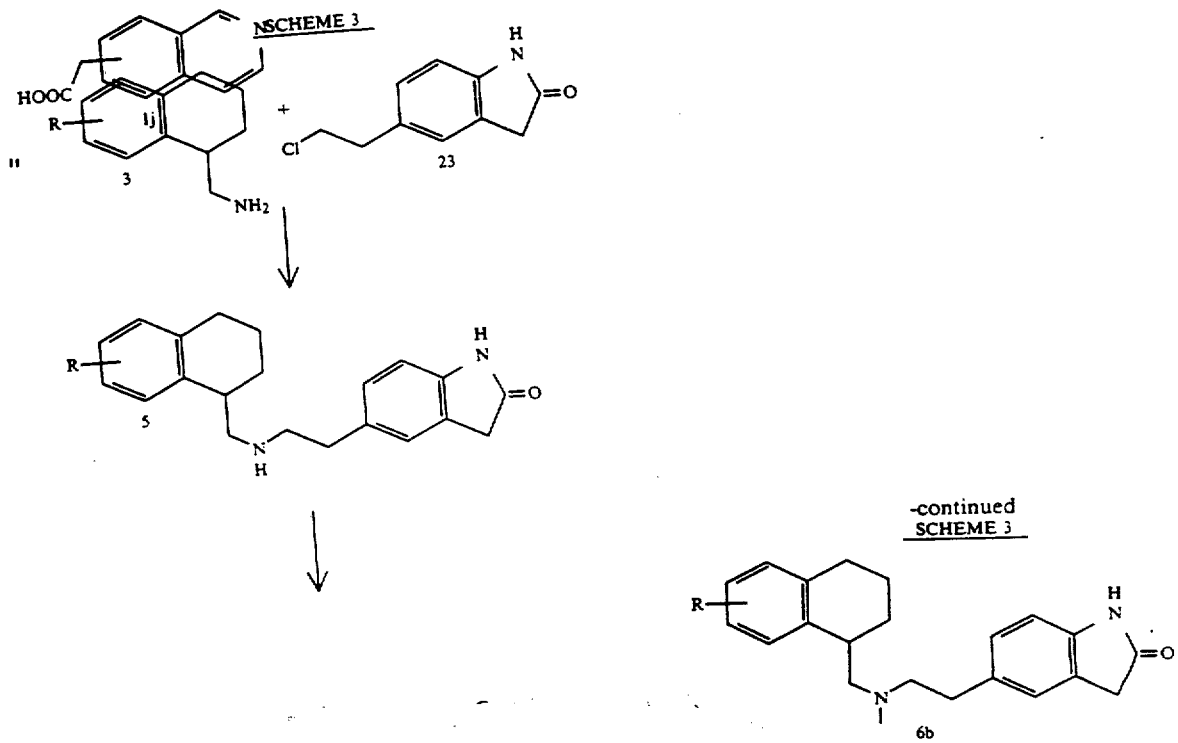

WITH

UNITED STATES PATENT AND TRADEMARK OFFICE
CERTIFICATE OF CORRECTION

PATENT NO. : 5,288,749

DATED : February 22, 1994

INVENTOR(S) : M. D. Meyer; J. F. DeBernardis; R. Prasad; K. B. Sippy; K. R. Tietje It is certified that error appears in the above-indentified patent and that said Letters Patent is hereby corrected as shown below:

-- 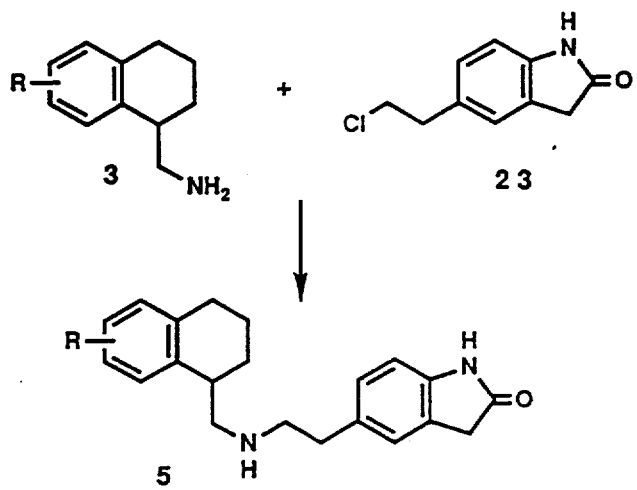 --

UNITED STATES PATENT AND TRADEMARK OFFICE
CERTIFICATE OF CORRECTION

PATENT NO. : 5,288,749
DATED : February 22, 1994
INVENTOR(S) : M.D. Meyer, et al.

It is certified that error appears in the above-indentified patent and that said Letters Patent is hereby corrected as shown below:

SCHEME 3

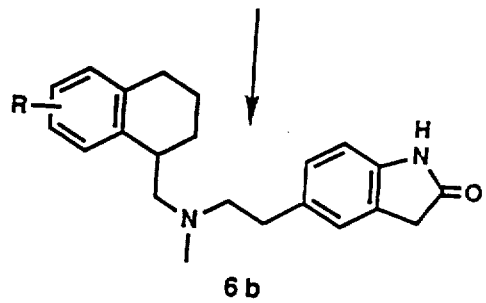

Signed and Sealed this

Twenty-sixth Day of December, 1995

Attest:

BRUCE LEHMAN

Attesting Officer      Commissioner of Patents and Trademarks